US011789011B2

(12) United States Patent
King et al.

(10) Patent No.: US 11,789,011 B2
(45) Date of Patent: Oct. 17, 2023

(54) ENGINEERED THREE-DIMENSIONAL BREAST TISSUE, ADIPOSE TISSUE, AND TUMOR DISEASE MODEL

(71) Applicants: Organovo, Inc., San Diego, CA (US); Oregon Health & Science University, Portland, OR (US)

(72) Inventors: Shelby Marie King, San Diego, CA (US); Deborah Lynn Greene Nguyen, San Diego, CA (US); Vivian A. Gorgen, San Diego, CA (US); Benjamin R. Shepherd, San Diego, CA (US); Sharon C. Presnell, San Diego, CA (US); Rosalie Sears, Portland, OR (US); Brittany Allen-Petersen, Portland, OR (US); Ellen Langer, Portland, OR (US)

(*) Notice: Subject to any disclaimer, the term of this patent is extended or adjusted under 35 U.S.C. 154(b) by 676 days.

(21) Appl. No.: 16/712,645

(22) Filed: Dec. 12, 2019

(65) Prior Publication Data

US 2020/0116702 A1    Apr. 16, 2020

Related U.S. Application Data

(60) Continuation of application No. 15/911,713, filed on Mar. 5, 2018, now abandoned, which is a division of application No. 14/678,392, filed on Apr. 3, 2015, now Pat. No. 9,983,195.

(60) Provisional application No. 61/976,895, filed on Apr. 8, 2014, provisional application No. 61/975,640, filed on Apr. 4, 2014.

(51) Int. Cl.
| | |
|---|---|
| *C12N 5/071* | (2010.01) |
| *G01N 33/50* | (2006.01) |
| *C12N 5/09* | (2010.01) |
| *B33Y 10/00* | (2015.01) |
| *B33Y 80/00* | (2015.01) |
| *C12N 5/077* | (2010.01) |

(52) U.S. Cl.
CPC .......... *G01N 33/5011* (2013.01); *B33Y 10/00* (2014.12); *B33Y 80/00* (2014.12); *C12N 5/0656* (2013.01); *C12N 5/0693* (2013.01); *C12N 5/0697* (2013.01); *G01N 33/5082* (2013.01); *C12N 2502/13* (2013.01); *C12N 2502/1305* (2013.01); *C12N 2502/1323* (2013.01); *C12N 2502/1358* (2013.01); *C12N 2502/28* (2013.01); *C12N 2513/00* (2013.01); *C12N 2533/74* (2013.01)

(58) Field of Classification Search
CPC .......... G01N 33/5011; G01N 33/5082; B33Y 10/00; B33Y 80/00; C12N 5/0656; C12N 5/0693; C12N 5/0697; C12N 2502/13; C12N 2502/1305; C12N 2502/1323; C12N 2502/1358; C12N 2502/28; C12N 2513/00; C12N 2533/74

See application file for complete search history.

(56) References Cited

U.S. PATENT DOCUMENTS

| | | | |
|---|---|---|---|
| 4,759,764 | A | 7/1988 | Fawcett et al. |
| 4,808,435 | A | 2/1989 | Cropp et al. |
| 5,099,090 | A | 3/1992 | Allan et al. |
| 6,315,469 | B1 | 11/2001 | Alvarez et al. |
| 6,401,795 | B1 | 6/2002 | Cesarano, III et al. |
| 6,454,972 | B1 | 9/2002 | Morisette et al. |
| 6,520,997 | B1 | 2/2003 | Pekkarinen et al. |
| 6,537,567 | B1 | 3/2003 | Niklason et al. |
| 6,561,607 | B1 | 5/2003 | Lubinsky et al. |
| 6,568,787 | B1 | 5/2003 | Girones et al. |
| 6,642,243 | B1 | 11/2003 | Imanzahrai |
| 6,713,772 | B2 | 3/2004 | Goodman et al. |
| 6,939,489 | B2 | 9/2005 | Moszner et al. |
| 6,942,830 | B2 | 9/2005 | Muelhaupt et al. |
| 6,979,670 | B1 | 12/2005 | Lyngstadaas et al. |
| 6,986,739 | B2 | 1/2006 | Warren et al. |
| 7,051,654 | B2 | 5/2006 | Boland et al. |
| 7,196,842 | B2 | 3/2007 | Weigl et al. |
| 7,484,837 | B2 | 2/2009 | Koga et al. |
| 7,625,198 | B2 | 12/2009 | Lipson et al. |
| 7,651,665 | B2 | 1/2010 | Gonzalez et al. |
| 7,680,555 | B2 | 3/2010 | Dunn et al. |
| 7,767,446 | B2 | 8/2010 | Robbins et al. |
| 7,887,843 | B2 | 2/2011 | Libera et al. |
| 7,980,645 | B2 | 7/2011 | Ohtsuka et al. |
| 8,143,055 | B2 | 3/2012 | Forgacs et al. |
| 8,241,905 | B2 | 8/2012 | Forgacs et al. |
| 8,343,740 | B2 | 1/2013 | Gonda et al. |
| 8,580,546 | B2 | 11/2013 | Gonda et al. |
| 8,728,807 | B2 | 5/2014 | Forgacs et al. |

(Continued)

FOREIGN PATENT DOCUMENTS

| | | |
|---|---|---|
| CA | 2306346 A1 | 1/1999 |
| EP | 2090584 A1 | 8/2009 |

(Continued)

OTHER PUBLICATIONS

Xu et al. "A three-dimensional in vitro ovarian cancer coculture model using a high-throughput cell patterning platform." Biotechnol J. Feb. 2011;6(2):204-212 (Year: 2011).*

(Continued)

*Primary Examiner* — Titilayo Moloye

(74) *Attorney, Agent, or Firm* — STERNE, KESSLER, GOLDSTEIN & FOX P.L.L.C.

(57) ABSTRACT

Described are three-dimensional, engineered, biological breast tissues, adipose tissues, and tumor models, including breast cancer models.

23 Claims, 33 Drawing Sheets

(56) References Cited

U.S. PATENT DOCUMENTS

| | | | |
|---|---|---|---|
| 8,747,880 B2 | 6/2014 | Forgacs et al. | |
| 8,852,932 B2 | 10/2014 | Forgacs et al. | |
| 8,931,880 B2 | 1/2015 | Murphy et al. | |
| 9,983,195 B2 | 5/2018 | King et al. | |
| 2001/0042942 A1 | 11/2001 | Hizumi et al. | |
| 2002/0171178 A1 | 11/2002 | Dean et al. | |
| 2002/0182633 A1 | 12/2002 | Chen et al. | |
| 2002/0188349 A1 | 12/2002 | McAllister et al. | |
| 2003/0049839 A1 | 3/2003 | Romero-Ortega et al. | |
| 2003/0149505 A1 | 8/2003 | Mogensen | |
| 2003/0153078 A1 | 8/2003 | Libera et al. | |
| 2003/0175410 A1 | 9/2003 | Campbell et al. | |
| 2003/0236588 A1 | 12/2003 | Jang et al. | |
| 2004/0006405 A1 | 1/2004 | Chen et al. | |
| 2004/0096966 A1 | 5/2004 | Ingram | |
| 2004/0132184 A1 | 7/2004 | Dennis et al. | |
| 2004/0197367 A1 | 10/2004 | Rezania et al. | |
| 2004/0219133 A1 | 11/2004 | Lyles | |
| 2004/0253365 A1 | 12/2004 | Warren et al. | |
| 2005/0009178 A1 | 1/2005 | Yost et al. | |
| 2005/0091576 A1 | 4/2005 | Relyea et al. | |
| 2005/0169962 A1 | 8/2005 | Bhatia et al. | |
| 2005/0226856 A1 | 10/2005 | Ahlfors | |
| 2005/0276791 A1 | 12/2005 | Hansford et al. | |
| 2006/0099287 A1 | 5/2006 | Kim et al. | |
| 2006/0198918 A1 | 9/2006 | Koyagi et al. | |
| 2006/0237880 A1 | 10/2006 | Wicker et al. | |
| 2006/0270032 A1 | 11/2006 | Bhatia et al. | |
| 2007/0142916 A1 | 6/2007 | Olson et al. | |
| 2007/0200276 A1 | 8/2007 | Mackey et al. | |
| 2007/0231787 A1 | 10/2007 | Voelker | |
| 2007/0299508 A1 | 12/2007 | Morrison et al. | |
| 2008/0027114 A1 | 1/2008 | Funke et al. | |
| 2008/0070304 A1 | 3/2008 | Forgacs et al. | |
| 2008/0097575 A1 | 4/2008 | Cottone | |
| 2008/0192074 A1 | 8/2008 | Dubois et al. | |
| 2008/0193910 A1 | 8/2008 | Larkin et al. | |
| 2009/0076531 A1 | 3/2009 | Richardson et al. | |
| 2009/0117087 A1 | 5/2009 | Carroll et al. | |
| 2009/0142307 A1 | 6/2009 | Athanasiou et al. | |
| 2009/0206522 A1 | 8/2009 | Hein et al. | |
| 2009/0208466 A1 | 8/2009 | Yoo et al. | |
| 2009/0208577 A1 | 8/2009 | Xu et al. | |
| 2009/0239302 A1 | 9/2009 | Decher et al. | |
| 2009/0248145 A1 | 10/2009 | Chan et al. | |
| 2009/0263849 A1 | 10/2009 | Sun et al. | |
| 2009/0267269 A1 | 10/2009 | Lim et al. | |
| 2010/0041134 A1 | 2/2010 | Forgacs et al. | |
| 2010/0056390 A1* | 3/2010 | Fischbach | C40B 60/08 506/10 |
| 2010/0160183 A1 | 6/2010 | Xu et al. | |
| 2010/0191360 A1 | 7/2010 | Napadensky et al. | |
| 2010/0254900 A1 | 10/2010 | Campbell et al. | |
| 2011/0064784 A1 | 3/2011 | Mullens et al. | |
| 2011/0172611 A1 | 7/2011 | Yoo et al. | |
| 2011/0177590 A1 | 7/2011 | Clyne et al. | |
| 2011/0212501 A1 | 9/2011 | Yoo | |
| 2011/0250688 A1 | 10/2011 | Hasan | |
| 2011/0280914 A1 | 11/2011 | Prestwich et al. | |
| 2012/0045770 A1 | 2/2012 | Pongracz et al. | |
| 2012/0089238 A1 | 4/2012 | Kang et al. | |
| 2012/0116568 A1 | 5/2012 | Murphy et al. | |
| 2013/0108726 A1 | 5/2013 | Uckelmann et al. | |
| 2013/0164339 A1 | 6/2013 | Murphy et al. | |
| 2013/0190210 A1 | 7/2013 | Murphy et al. | |
| 2013/0193619 A1 | 8/2013 | Church et al. | |
| 2013/0236431 A1 | 9/2013 | Gourdie et al. | |
| 2013/0236879 A1 | 9/2013 | Berry et al. | |
| 2013/0345794 A1 | 12/2013 | Khatiwala et al. | |
| 2014/0012225 A1 | 1/2014 | Yoo et al. | |
| 2014/0044822 A1 | 2/2014 | Mulliken | |
| 2014/0093932 A1 | 4/2014 | Murphy et al. | |
| 2014/0099709 A1 | 4/2014 | Presnell et al. | |
| 2014/0131313 A1 | 5/2014 | Wakamatsu et al. | |
| 2014/0220685 A1 | 8/2014 | Forgacs et al. | |
| 2014/0265049 A1 | 9/2014 | Burris et al. | |
| 2014/0274802 A1 | 9/2014 | Shepherd et al. | |
| 2014/0287960 A1 | 9/2014 | Shepherd et al. | |
| 2014/0358273 A1 | 12/2014 | Labossiere et al. | |
| 2015/0004273 A1 | 1/2015 | Forgacs et al. | |
| 2015/0037445 A1 | 2/2015 | Murphy et al. | |
| 2015/0057786 A1 | 2/2015 | Murphy et al. | |
| 2015/0282885 A1 | 10/2015 | King et al. | |

FOREIGN PATENT DOCUMENTS

| | | |
|---|---|---|
| JP | 2001038981 A | 2/2001 |
| JP | 2005031144 A | 2/2005 |
| JP | 2006159117 A | 6/2006 |
| KR | 20090087748 A | 8/2009 |
| RU | 2371758 C2 | 10/2009 |
| WO | WO-9901538 A1 | 1/1999 |
| WO | WO-0168811 A2 | 9/2001 |
| WO | WO-2004108418 A1 | 12/2004 |
| WO | WO-2005025493 A2 | 3/2005 |
| WO | WO-2005081970 A2 | 9/2005 |
| WO | WO-2007076272 A2 | 7/2007 |
| WO | WO-2007115336 A2 | 10/2007 |
| WO | WO-2007115337 A2 | 10/2007 |
| WO | WO-2007124023 A2 | 11/2007 |
| WO | WO-2007125893 A1 | 11/2007 |
| WO | WO-2007126411 A2 | 11/2007 |
| WO | WO-2007136936 A2 | 11/2007 |
| WO | WO-2009102484 A2 | 8/2009 |
| WO | WO-2009154466 A1 | 12/2009 |
| WO | WO-2010008905 A2 | 1/2010 |
| WO | WO-2011038373 A2 | 3/2011 |
| WO | WO-2011088213 | 7/2011 |
| WO | WO-2011097330 A2 | 8/2011 |
| WO | WO-2011107599 A1 | 9/2011 |
| WO | WO-2011119059 A1 | 9/2011 |
| WO | WO-2012003465 A2 | 1/2012 |
| WO | WO-2012054195 A2 | 4/2012 |
| WO | WO 2012/131000 A1 | 10/2012 |
| WO | WO-2013130823 A1 | 9/2013 |
| WO | WO 2013/192290 A1 | 12/2013 |

OTHER PUBLICATIONS

Correa de Sampaio et al. "A heterogeneous in vitro three dimensional model of tumour-stroma interactions regulating sprouting angiogenesis." PLoS One. 2012;7(2):e30753. (Year: 2012).*

Olsen et al. "Human mammary fibroblasts stimulate invasion of breast cancer cells in a three-dimensional culture and increase stroma development in mouse xenografts." BMC Cancer. Aug. 19, 2010;10:444. (Year: 2010).*

Zhang et al. "Stromal progenitor cells from endogenous adipose tissue contribute to pericytes and adipocytes that populate the tumor microenvironment." Cancer Res. Oct. 15, 2012;72(20):5198-208. (Year: 2012).*

Klopp et al. "Omental adipose tissue-derived stromal cells promote vascularization and growth of endometrial tumors." Clin Cancer Res. Feb. 1, 2012;18(3):771-82. (Year: 2012).*

Li et al. "TGF-β/SMAD signaling regulation of mesenchymal stem cells in adipocyte commitment." Stem Cell Res Ther. Jan. 29, 2020;11(1):41. (Year: 2020).*

Baltich et al. Development of a Scaffoldless Three-Dimensional Engineered Nerve Using a Nerve-Fibroblast Co-Culture. In Vitro Cell. Dev. Biol.—Animal, 2010 46:438-444.

Bioscaffolder 2008, www.syseng.de, SYSENG Dipl.-Ing. Hendrik John.

Boland et al. Application of inkjet printing to tissue engineering. Biotech J. 1:910-917 (2006).

Boland et al. Cell and Organ Printing 2: Fusion of Cell Aggregates in Three-Dimensional Gels. The Anatomical Record, Part A. 272A:497-502 (2003).

Chaterji et al. Scaffold-Free In Vitro Arterial Mimetics: The Importance of Smooth Muscle-Endothelium Contact. Tissue Engineering Part A 16(8):1901-1912 (2010).

(56) References Cited

OTHER PUBLICATIONS

Sciperio, Inc. 2003 R&D 100 Award Winner. Sciperio, http://www.sciperio.com/news/20031016.asp, accessed on Feb. 1, 2005, 2 pages.
Constans. Body by Science. The Scientist 17(19):34-37 http://www.the-scientist.com/article/display/141541 (2003).
Dai et al. Fibroblast Aggregation by Suspension with Conjugates of Poly(ethylene glycol) and RGD. Biotechnology and Bioengineering 50(4):349-356 (May 20, 1996).
Dominici et al. Minimal criteria for defining multipotent mesenchymal stromal cells, International Society for Cellular Therapy position statement. Cytotherapy 8(4):315-317 (2006).
Edelman. Vascular Tissue Engineering: Designer Arteries. Giro Res 85(12):1115-1117 (1999).
Eisenberg et al. Bone Marrow Cells Transdifferentiate to Cardiomyocytes When Introduced into the Embryonic Heart. Stem Cells 24:1236-1245 (2006).
Fedorovich et al. Distinct Tissue Formation by Heterogeneous Printing of Osteo- and Endothelial Progenitor Cells. Tissue Engineering: Part A 17(15-16):2113-2123 (2011).
Fedorovich et al. Three-Dimensional Fiber Deposition of Cell-Laden, Viable Patterned Constructs for Bone Tissue Printing, Tissue Engineering: Part A 14(1):127-135 (2008).
Forgacs et al. Viscoelastic Properties of Living Embryonic Tissues: A Quantitative Study, Biophysical Journal 74(5):2227-2234 (May 1998).
Foty et al. Surface Tensions of Embryonic Tissues Predict Their Mutual Envelopment Behavior. Development 122(5):1611-1620 (1996).
Foty et al. The Differential Adhesion Hypothesis: A Direct Evaluation. Developmental Biology 278(1):255-263 (2005).
Frisman et al. Nanostructuring of PEG-fibrinogen polymeric scaffolds. Acta Biomaterialia 6(7):2518-2524 (2009).
Fuellhase et al. 264 Generation Of Organized Bladder Tissue Constructs Using A Novel Hybrid Printing System. European Urology Supplements 8(4):186 (2009).
Furukawa et al. Formation of Human Fibroblast Aggregates (Spheroids) by Rotational Culture. Cell Transplantation 10(4-5):441-445 (2001).
Furukawa et al. Scaffold-free cartilage tissue by mechanical stress loading for tissue engineering. In Tissue Engineering, ed by Daniel Eberli. InTech 2010, p. 409-428.
Furukawa et al. Tissue-engineered Skin Using Aggregates of Normal Human Skin Fibroblasts and Biodegradable Material. J. MK Organs 4:353-356 (2001).
Ghorbanian et al. Microfluidic direct writer with integrated declogging mechanism for fabricating cell-laden hydrogel constructs. Biomed Microdevices (doi: 10.1007/s10544-014-9842-8), Springer Science+Business Media New York 2014 (Mar. 4, 2014).
Glazier et al. Simulation of the Differential Adhesion Driven Rearrangement of Biological Cells. Physical Review E 47(3):2128-2154 (Mar. 1993).
Glicklis et al. Modeling Mass Transfer in Hepatocyte Spheroids Via Cell Viability, Spheroid Size, and Hepatocellular Functions. Biotechnology and Bioengineering 86(6):672-680 (Jun. 20, 2004).
Graner et al. Simulation of Biological Cell Sorting Using a Two-Dimensional Extended Potts Model. Physical Review Letters 69(13):2013-2016 (Sep. 28, 1992).
Gruene et al. Laser Printing of Stem Cells for Biofabrication of Scaffold-Free Autologous Grafts. Tissue Engineering: Part C 17(1):79-89 (2011).
Gruene et al. Laser printing of three-dimensional multicellular arrays for studies of cell-cell and cell-environment interactions. Tissue Eng Part C Methods 17(10):973-82 (Oct. 2011).
Guenard et al. Syngeneic Schwann Cells Derived from Adult Nerves Seeded in Semipermeable Guidance Channels Enhance Peripheral Nerve Regeneration. The Journal of Neuroscience 12(9):3310-3320 (Sep. 1992).
Guillemot et al. High-throughput laser printing of cells and biomaterials for tissue engineering. Acta biomaterialia 6:2494-2500 (2010).
Hadlock et al. A Polymer Foam Conduit Seeded with Schwann Cells Promotes Guided Peripheral Nerve Regeneration. Tissue Engineering 6(2):119-127 (2000).
Halley et al. Growing Organs In the Lab. Longevity. 1-7 (Jun. 2009).
Harvey et al. Schwann cells and fetal tectal tissue cografted to the midbrain of newborn rats: fate of Schwann cells and their influence on host retinal innervation of grafts. Exp Neurol. 134(2):179-91 (1995).
Hockaday et al. Rapid 3D printing of anatomically accurate and mechanically heterogeneous aortic valve hydrogel scaffolds. Biofabrication 4(3):1-12 (2012).
Hubbard et al. Bioengineered, Autologous, Scaffold-free Nerve Conduit for Peripheral Nerve Repair. Abstract. AAHS/ASPN/ASRM 2011, Annual Scientific Meetings Program Book, pp. 140 and 159 (Jan. 12-18, 2011).
Ito et al. Novel Methodology for Fabrication of Tissue-Engineered Tubular Constructs Using Magnetite Nanoparticles and Magnetic Force, Tissue Engineering, Larchmont, NY, US, 11(9-10):1553-1561 (2005).
Iwasaki et al. Bioengineered Three-Layered Robust and Elastic Artery Using Hemodynamically-Equivalent Pulsatile Bioreactor. Circulation 18(14 Suppl):S53-S57 (2008).
Jakab et al. Engineering Biological Structures of Prescribed Shape Using Self-assembling Multicellular Systems. PNAS USA 101:2864-2869 (2004).
Jakab et al. Relating Cell and Tissue Mechanics: Implications and Applications. Developmental Dynamics 237:2438-2449 (2008).
Jakab et al. Tissue Engineering by Self-Assembly and Bio-printing of living cells. Biofabrication 2(2):022001 (14 pp) (Jun. 2, 2010).
Jakab et al. Tissue Engineering by Self-Assembly of Cells Printed into Topologically Defined Structures. Tissue Engineering: Part A. 14:413-421 (Nov. 3, 2008).
Kasko. Degradable Poly(ethylene glycol) Hydrogels for 2D and 3D Cell Culture. Aldrich Materials Science, pp. 67-75 (no date available).
Kelm et al. Design of Custom-Shaped Vascularized Tissues Using Microtissue Spheroids as Minimal Building Units. Tissue Engineering 12(8):2151-2160 (2006).
Kelm et al. Microscale Tissue Engineering Using Gravity-Enforced Cell Assembly. Trends in Biotechnology 22(4):195-202 (Apr. 2004).
King et al. Development of 3D bioprinted human breast cancer for in vitro screening of therapeutics targeted against cancer progression. IEEE The American Society for Cell biology. 2013 ascb annual meeting. New Orleans: IEEE Dec. 14-18, 2013.
Koibuchi et al. Behavior of Cells in Artificially Made Cell Aggregates and Tissue Fragments after Grafting to Developing Hind Limb Buds in Xenopus laevis. The International Journal of Developmental Biology 43(2):141-148 (1999).
Korff et al. Blood Vessel Maturation in a 3-Dimensional Spheroidal Coculture Model: Direct Contact with Smooth Muscle Cells Regulates Endothelial Cell Quiescence and Abrogates VEGF Responsiveness. The FASEB Journal 15:447-457 (Feb. 2001).
Larkin et al. Structure and Functional Evaluation of Tendon-Skeletal Muscle Constructs Engineered in Vitro. Tissue Eng. 12(11):3149-3158 (Nov. 2006).
Lee et al. Multi-layered Culture of Human Skin Fibroblasts and Keratinocytes Through Three-dimensional Freeform Fabrication. Biomaterials 30:1587-1595 (2009).
L'Heureux et al. A completely biological tissue-engineered human blood vessel. The FASEB Journal 12 (1):47-56 (1998).
L'Heureux et al. Human tissue-engineered blood vessels for adult arterial revascularization. Nature Medicine 12 (3):361-365 (2006).
L'Heureux et al. Sheet-Based Tissue Engineering From Bench Top to the First Clinical Use of a Completely Biological Tissue Engineered Vessel. The FASEB Journal 12(1):47-56 (Abstract) (2006).
Luo et al. Three-dimensional microtissue assay for high-throughput cytotoxicity of nanoparticles. Anal Chem. 84(15):6731-6738 (Aug. 7, 2012).
Marga et al. Bioprint Engineered Fully Biological Nerve Graft. Poster Presentation Termis Dec. 5-8, 2010, Orlando, Florida, 1 page.
Marga et al. Construction of a Bioprinted Fully Biological Nerve Graft. Biophysical Journal 96(3 supp 1) :643a Abstract (Feb. 2009).

(56) References Cited

OTHER PUBLICATIONS

Marga et al. Developmental Biology and Tissue Engineering, Birth Defects Research (Part C) 81:320-328 (2007).
Marga et al. Engineered Fully Biological Nerve Graft. Oral Presentation, International Conference on Biofabrication, Oct. 3-6, 2010, Philadelphia, Pennsylvania, 1 page.
Marga et al. Engineered Fully Biological Nerve Graft. Poster Presentation Biophysical Society Meeting, Mar. 4, 2009, 1 page.
Marga et al. Toward Engineering Functional Organ Modules by Additive Manufacturing. Biofabrication 4:022001 (12 pp) (2012).
Martin et al. Computer-Based Technique for Cell Aggregation Analysis and Cell Aggregation in In Vitro Chondrogenesis. Cytometry 28(2):141-146 (1997).
McGuigan et al. Vascularized organoid engineered by modular assembly enables blood perfusion. PNAS, 103(31):11461-11466 (2006).
Mehesz et al. Scalable robotic biofabrication of tissue spheroids. Biofabrication 3:1-8 (2011).
Mironov et al. Bioprinting Living Structures. J. Mat. Chem. 17:2054-2060 (2007).
Mironov et al. Organ Printing: Computer-Aided Jet-Based 3D Tissue Engineering. TRends in Biotechnology 21(4):157-161 (Apr. 2003).
Mironov et al. Organ Printing: Self-Assembling Cell Aggregates as 'Bioink'. Science & Medicine 9(2):69-71 (Apr. 2003).
Mironov et al. Organ Printing: Tissue Spheroids as Building Blocks. Biomaterials 30:2164-2174 (2009).
Mizumoto et al. Formation of Cylindrical Multicellular Aggregate (Cylindroid) and Express of Liver Specific Functions of Primary Rat Hepatocytes. Cytotechnology 31:69-75 (1999).
Mombach et al. Quantitative Comparison Between Differential Adhesion Models and Cell Sorting in the Presence and Absence of Fluctuations. Physical Review Letters 75(11):2244-2247 (Sep. 11, 1995).
Moon et al. Layer by Layer Three-dimensional Tissue Epitaxy by Cell-Laden Hydrogel Droplets. Tissue Engineering Part C: Methods 16(1):157-166 (2010).
Mroue et al. Three-dimensional cultures of mouse mammary epithelial cells. Methods Mol Biol. 945:221-250 (2013).
Nickerson et al. Three-Dimensional Tissue Assemblies: Novel Models for the Study of *Salmonella enterica* Serovar Typhimurium Pathogenesis. Infection and Immunity 69(11):7106-7120 (Nov. 2001).
Niklason et al. Advances in Tissue Engineering of Blood Vessels and Other Tissues. Transpl. Immunol. 5(4):303-306 (1997).
Norotte et al. Scaffold-free vascular tissue engineering using bioprinting. Biomaterials 30:5910-5917 (2009).
Panagiotis et al. A unique aged human retinal pigmental epithelial cell line useful for studying lens differentiation in vitro. International Journal of Developmental Biology 45:753-758 (2001).
Pathology Outlines: Bladder. Normal Histology, pp. 1-4 (2011).
Paul et al. How to improve R&D productivity: the pharmaceutical industry's grand challenge. Nature Reviews Drug Discovery 9(3):203-214 (2010).
PCT/US2005/05735 International Search Report dated Dec. 7, 2007.
PCT/US2005/05735 International Preliminary Report on Patentability dated Mar. 3, 2009.
PCT/US2009/48530 International Preliminary Report on Patentability dated Jan. 13, 2011.
PCT/US2009/48530 International Search Report dated Mar. 15, 2010.
PCT/US2011/023520 International Preliminary Report on Patentability dated Aug. 16, 2012.
PCT/US2011/023520 International Search Report dated Oct. 31, 2011.
PCT/US2011/028713 International Preliminary Report on Patentability dated Sep. 18, 2012.
PCT/US2011/028713 International Search Report dated Nov. 30, 2011.
PCT/US2011/053515 International Preliminary Report on Patentability dated May 3, 2013.
PCT/US2011/053515 International Search Re|2 t and Written Opinion dat41 dated May 1, 2012.
PCT/US2012/054923 International Preliminary Report on Patentability dated Mar. 20, 2014.
PCT/US2012/054923 International Search Report dated Feb. 26, 2013.
PCT/US2012/054935 International Preliminary Report on Patentability dated Mar. 20, 2014.
PCT/US2012/054935 International Search Report dated Feb. 28, 2013.
PCT/US2013/036479 International Preliminary Report on Patentability dated Oct. 21, 2014.
PCT/US2013/036479 International search report dated Jul. 25, 2013.
PCT/US2013/046519 International Preliminary Report on Patentability dated Dec. 23, 2014.
PCT/US2013/046519 International Search Report dated Sep. 5, 2013.
PCT/US2014/026679 International Search Report and Written Opinion dated Jul. 22, 2014.
PCT/US2014/048962 International Search Report and Written Opinion dated Nov. 10, 2014.
PCT/US2014/041419 International Search Report and Written Opinion dated Jan. 2, 2015.
Perez-Pomares et al. Tissue Fusion and Cell Sorting in Embryonic Development and Disease: Biomedical Implications. Bioessays 28:809-821 (2006).
Remuzzi et al. Vascular Smooth Muscle Cells on Hyaluronic Acid: Culture and Mechanical Characterization of an Engineered Vascular Construct. Tissue Engineering 10(516):699-710 (2004).
Riken. Self-healing hydrogels ease into production. Research Highlights: Materials. Downloaded from the Riken website: <http://www.riken.jp/en/research/rikenresearch/highlights/7543/> (Nov. 1, 2013) [accessed Apr. 27, 2015].
Ryan et al. Tissue Spreading on Implantable Substrates is a Competitive Outcome of Cell-Cell vs. Cell-Substratum Adhesivity. PNAS 98(8):4323-4327 (Apr. 10, 2001).
Schuster et al. Why Drugs Fail—A Study on Side Effects in New Chemical Entities. Curr. Pharm. Des. 11:3545 (2005).
Shim et al. Bioprinting of a mechanically enhanced three-dimensional dual cell-laden construct for osteochondral tissue engineering using a multi-head tissue/organ building system. J of Micromechanics and Microengineering. 22(Article No. 085014):1-11 (2012).
Siemionow et al. Current Techniques and Concepts in Peripheral Nerve Repair. Chapter 8, International Review of Neurobiology, 87:141-172 (2009).
Skardal et al. Bioprinting vessel-like constructs using hyaluronan hydrogels crosslinked with tetrahedral polyethylene glycol tetracrylates. Biomaterials 31:6173-6181 (2010).
Smith. A direct-write three-dimensional Bioassembly tool for regenerative medicine. The University of Arizona pp. 1-291 (Nov. 1, 2005).
Smith et al. Characterizing Environment Factors that Impact the Viability of Tissue-Engineered Constructs Fabricated by a Direct-Write Bioassembly Tool. Tissue Engineering, 13(2):373-385 (2007).
Smith et al. Three-Dimensional BioAssembly Tool for Generating Viable Tissue-Engineered Constructs. Tissue Engineering 10(9/10):1566-1576 (2004).
Steinberg. Does Differential Adhesion Govern Self-Assembly Processes in Histogenesis? Equilibrium Configurations and the Emergence of a Hierarchy Among Populations of Embryonic Cells. The Journal of Experimental Zoology 173(4):395-433 (Apr. 1970).
Steinberg et al. Liquid Behavior of Embryonic Tissues. Cell Behaviour pp. 583-697 (1982).
Stiles. UA Wins R & D 100 Award for Machine that Prints Tissue Cell-by-Cell. UANews Dec. 2, 2003, http://uanews.org/cgi-binfflebObjects/UANews.woa/wa/goPrint?ArticleID=8305, accessed on Feb. 1, 2005, 2 pages.

(56) References Cited

OTHER PUBLICATIONS

Tang et al. Molding of Three-Dimensional Microstructures of Gels. Journal of the American Chemical Society 125(43):12988-12989 (Oct. 29, 2003).
Tao et al. Bio-printing of living organized tissues using an inkjet technology. Database Accession No. PREV200700335042. FASEB Journal 23(5):A636 (2007).
Timmins et al. Hanging-Drop Multicellular Spheroids as a Model of Tumour Angiogenesis. Angiogenesis 7(2):97-103 (2004).
Tsang. Three-Dimensional Tissue Fabrication, Advanced drug delivery reviews 56(11):1635-1647 (2004).
U.S. Appl. No. 10/590,446 Office action dated Jan. 6, 2011.
U.S. Appl. No. 10/590,446 Office action dated Sep. 1, 2011.
U.S. Appl. No. 10/666,836 Office action dated Oct. 28, 2004.
U.S. Appl. No. 11/227,489 Office action dated Dec. 10, 2008.
U.S. Appl. No. 11/227,489 Office action dated Jul. 8, 2009.
U.S. Appl. No. 13/020,000 Office action dated Dec. 31, 2012.
U.S. Appl. No. 13/020,000 Office action dated Jul. 3, 2013.
U.S. Appl. No. 13/246,428 Office Action dated Aug. 26, 2014.
U.S. Appl. No. 13/246,428 Office Action dated Jan. 14, 2015.
U.S. Appl. No. 13/402,215 Office Action dated Mar. 19, 2013.
U.S. Appl. No. 13/529,172 Office action dated Sep. 24, 2013.
U.S. Appl. No. 13/612,768 Office Action dated May 30, 2014.
U.S. Appl. No. 13/612,768 Office Action dated Nov. 17, 2014.
U.S. Appl. No. 13/612,768 Office Action dated Oct. 1, 2013.
U.S. Appl. No. 13/612,778 Office Action dated Apr. 28, 2014.
U.S. Appl. No. 13/612,778 Office Action dated Nov. 7, 2014.
U.S. Appl. No. 13/634,863 Office Action dated Jan. 28, 2015.
U.S. Appl. No. 13/794,368 Office Action dated May 8, 2015.
U.S. Appl. No. 13/794,368 Office Action dated Nov. 26, 2014.
U.S. Appl. No. 13/801,780 Office Action dated Nov. 14, 2014.
U.S. Appl. No. 13/968,313 Office Action dated Jun. 26, 2014.
U.S. Appl. No. 14/295,226 Office Action dated May 7, 2015.
U.S. Appl. No. 14/295,226 Office Action dated Oct. 8, 2014.
U.S. Appl. No. 14/447,412 Office Action dated Mar. 3, 2015.
U.S. Appl. No. 14/530,499 Office Action dated May 14, 2015.
Wake Forest Baptist Medical Center (Wake Forest Physician Reports First Human Recipients of Laboratory-Grown Organs. 2006 pp. 1-2).
Wang et al. Bone marrow mesenchymal stem cells promote cell proliferation and neurotrophic function of Schwann cells in vitro and in vivo. Brain Research 1262:7-15 (2009).
Xu et al. A three-dimensional in vitro ovarian cancer coculture model using a high-throughput cell patterning platform. Biotechnology Journal 6(2):204-212 (2011).
Xu et al. In vivo generation of functional tissues using the inkjet printing technology. Tissue Engineering 13(7):1713-1714 (2007).
Yamauchi et al. A Three-Dimensional Cell Culture Model for Bovine Endometrium: Regeneration of a Multicellular Spheroid Using Ascorbate. Placenta 24:258-269 (2003).
Bunnell et al. Adipose-derived Stem Cells: Isolation, Expansion and Differentiation. Methods 45(2):115-120 (2008).
Co-pending U.S. Appl. No. 14/796,910, filed Jul. 10, 2015.
Forgacs et al. Biological Relevance of Tissue Liquidity and Viscoelasticity Eds. A. Deutsch, M. Falcke, J. Howard and W. Zimmermann. Birkhauser, pp. 269-277 (2004).
Izaguirre et al. CompuCell, a multi-model framework for simulation of morphogenesis. Bioinformatics 20(7):1129-1137 (2004).
Jakab et al. Organ printing: fiction or science. Biorheology 43(3-4):371-375 (2004).
Jakab et al. Three-dimensional tissue constructs built by bioprinting. Biorheology 43(3-4):509-513 (2006).
Khatiwala et al. 3D Cell Bioprinting for Regenerative Medicine Research and Therapies. Gene Therapy and Regulation 7(1):1-19 (2012).
Mironov et al. Organ printing: self-assembling cell aggregates as a "bioink". Science and Medicine 9:69-71 (2003).
Neagu et al. Role of physical mechanisms in biological self-organization. Phys RevLett 95(17):178104 (2005).

Newman et al. Before programs: the physical origination of multicellular forms. Int J Dev Biol. 50(2-3):289-299 (2006).
Shafrir et al. Mechanotransduction through the cytoskeleton. American Journal of Physiology 282:479-486 (2002).
Sheehan et al. Recent Patents and Trends in Bioprinting. Recent Patents on Biomedical Engineering 4:26-32 (2011).
U.S. Appl. No. 13/612,768 Office Action dated Jul. 30, 2015.
U.S. Appl. No. 13/801,780 Office Action dated Jun. 5, 2015.
U.S. Appl. No. 14/447,412 Office Action dated Jul. 15, 2015.
Co-pending U.S. Appl. No. 14/827,152, filed Aug. 14, 2015.
Co-pending U.S. Appl. No. 14/876,659, filed Oct. 6, 2015.
PCT/US2014/026679 International Preliminary Report on Patentability dated Sep. 24, 2015.
U.S. Appl. No. 13/634,863 Office Action dated Sep. 8, 2015.
U.S. Appl. No. 14/295,226 Office Action dated Sep. 9, 2015.
U.S. Appl. No. 14/678,392 Office Action dated Oct. 8, 2015.
U.S. Appl. No. 14/678,392 Office Action dated Sep. 24, 2015.
U.S. Appl. No. 14/796,910 Office Action dated Sep. 25, 2015.
Zhang et al. Characterization of printable cellular micro-fluidic channels for tissue engineering. Biofabrication 5:025004 (2013).
Bernstein et al. Flow cytometric analysis of mature adipocytes. Cytometry 110(4):469-474 (1989).
Co-pending U.S. Appl. No. 14/933,822, filed Nov. 5, 2015.
Co-pending U.S. Appl. No. 14/936,580, filed Nov. 9, 2015.
Co-pending U.S. Appl. No. 14/950,567, filed Nov. 24, 2015.
Cui et al. Direct Human Cartilage Repair Using Three-Dimensional Bioprinting Technology. Tissue Engineering Part A 18(11-12):1304-1312 (2012).
Fujita et al. Fabrication of scaffold-free contractile skeletal muscle tissue using magnetite-incorporated myogenic C2C12 cells. J Tissue Eng Regen Med. 4(6):437-443 (2010).
Hierlihy et al. The post-natal heart contains a myocardial stem cell population. FEBS Letters 530:239-243 (2002).
Liu et al. Design and Development of Three-Dimensional Scaffolds For Tissue Engineering. Chemical Engineering Research and Design 85(7):1051-1064 (2007).
Patrick et al. Chapter 10. Epithelial Cell Culture: Breast. Methods of Tissue Engineering. Ed. Anthony Atala and Robert P. Lanza San Diego: Academic Press, pp. 141-149 (2002).
Pearson Education. Human Heart Illustration (2004).
Rizzati et al. Lipid Droplets Characterization in Adipocyte Differentiated 3T3-L1 Cells: Size and Optical Density Distribution. Eur J Histochem 57(3):159-162 (2013).
Tanaka et al. A Valved Hepatic Portoduodenal Instestinal Conduit for Biliary Atresia. Ann. Surg. 213(3):230-235 (1991).
Tsang et al. Fabrication of 3D hepatic tissues by additive photopatterning of cellular hydrogels. The FASEB Journal 21(3):790-801 (2007).
U.S. Appl. No. 13/612,778 Office Action dated Nov. 17, 2015.
U.S. Appl. No. 13/794,368 Office Action dated Sep. 23, 2015.
U.S. Appl. No. 14/244,679 Office Action dated Oct. 23, 2015.
Hemmrich, K., et al., "Optimization of the differentiation of human preadipocytes in vitro," *Differentiation* 73:28-35, International Society of Differentiation, United States (2005).
Co-pending Application, U.S. Appl. No. 15/301,641, inventors King, Shelby Marie, et al., filed Oct. 3, 2016 (Not yet Published).
Benton, G., et al., "Extracellular Matrix Proteins for Triculture of Breast Cancer Spheroids, Endothelial Tubules and Human Mesenchymal Stem Cells," White Paper—ECM Proteins for 3D Triculture, accessed at http://www.amsbio.com/news/whitepaper/Breast_Cancer_Triculture_white_paper.pdf, last accessed on Aug. 21, 2017, 6 pages (Nov. 2014).
Kolesky, D.B., et al., "3D Bioprinting of Vascularized, Heterogeneous Cell-Laden Tissue Constructs," *Advanced Materials* 26(19):3124-3130, Wiley-VCH Verlag GmbH & Co., Germany (May 2014; published online Feb. 2014).
Pampaloni, F. and Stelzer, E.H.K., "Three-Dimensional Cell Cultures in Toxicology," *Biotechnology and Genetic Engineering Reviews* 26:117-138, Taylor & Francis, England (2009).
Extended European Search Report for EP Application No. 14887943.0, Munich, Germany, dated Aug. 17, 2017, 11 pages.
Benton, G.J., et al., "A comprehensive 3D triple coculture model for evaluating breast cancer progression," *Cancer Research* 74(19

(56) References Cited

OTHER PUBLICATIONS

Suppl): Abstract No. 2033, in Proceedings of the 105th Annual Meeting of the American Association for Cancer Research, Apr. 5-9, 2014, American Association for Cancer Research. United States (Oct. 2014).
Office Action dated Apr. 19, 2016, in U.S. Appl. No. 14/678,392, King et al., filed Apr. 3, 2015, 24 pages.
Office Action dated Sep. 24, 2015, in U.S. Appl. No. 14/678,392, King et al., filed Apr. 3, 2015, 26 pages.
Office Action dated Oct. 8, 2015, in U.S. Appl. No. 14/678,392, King et al., filed Apr. 3, 2015, 25 pages.
Office Action dated Mar. 17, 2017, in U.S. Appl. No. 14/678,392, King et al., filed Apr. 3, 2015, 10 pages.
Kuri-Harcuch, W., et al., "Adipose conversion of 3T3 cells depends on a serum factor," Proc. Natl. Acad. Sci 75:6107-6109, United States National Academy of Sciences, United States (1978).
Yao, R., et al., "In Vitro Angiogenesis of 3D Tissue Engineered Adipose Tissue," Journal of Bioactive and Compatible Polymers, 24:5-24, Sage Publications, United States (2009).
Primary Subcutaneous Pre-adipocytes; Normal, Human (ATCC® PCS-210-010™), Sep. 19, 2015, 1 page.
Egeblad, M., et al., "Tumors as Organs: Complex Tissues that Interface with the Entire Organism," Developmental Cell 18:884-901, Elsevier, Netherlands (2010).
MCF7 (ATCC® HTB-22™), Sep. 19, 2015, 1 page.
Grange, C., et al., "Isolation and characterization of human breast tumor-derived endothelial cells," Oncology Reports 15:381-386, Demetrios Spandidos, Greece (2006).
Dirat, B., et al., "Cancer-Associated Adipocytes Exhibit an Activated Phenotype and Contribute to Breast Cancer Invasion," Cancer Res. 71(7):2455-2465, American Association for Cancer Research, United States (2011).
King S. M et al., "Development of 3D bioprinted human breast cancer for in vitro screening of therapeutics targeted against cancer progression," Mol. Biol. Cell 24(24):3775 (Abstract No. 921), American Society of Cell Biology, United States (Dec. 2013).
Correa De Sampaia, P., et al., "A Heterogeneous In Vitro Three Dimensional Model of Tumour-Stroma Interactions Regulating Sprouting Angiogenesis," PLoS One 7(2):e30753, The Public Library of Science, United States (2012).
Klopp, A.H., et al., "Omental adipose tissue-derived stromal cells promote vascularization and growth of endometrial tumors," Clin Cancer Res. 18(3):771-782, American Association for Cancer Research, United States (2012).
Ingthorsson, S., et al., "Endothelial cells stimulate growth of normal and cancerous breast epithelial cells in 3D culture," BMC Res Notes 3:184, BioMed Central, United Kingdom (2010).
Olsen, C., et al., "Human mammary fibroblasts stimulate invasion of breast cancer cells in a three-dimensional culture and increase stroma development in mouse xenografts," BMC Cancer 10:444, BioMed Central, United Kingdom (2010).
Xu, T., et al., "Complex heterogeneous tissue constructs containing multiple cell types prepared by inkjet printing technology," Biomaterials 34(1): 130-139, Elsevier, Netherlands (2013).
Zhang, Y., et al., "Stromal Progenitor Cells From Endogenous Adipose Tissue Contribute to Pericytes and Adipocytes That Populate the Tumor Microenvironment," Cancer Res. 72(20):5198-208, American Association for Cancer Research, United States (2012).
King S. M et al., "Development of 3D bioprinted human breast cancer for in vitro screening of therapeutics targeted against cancer progression," Organovo Presentation No. 1805, San Diego, CA(2013).
Munir, H., e al., "Adipogenic Differentiation of Mesenchymal Stem Cells Alters Their Immunomodulatory Properties in a Tissue-Specific Manner: Tissue-Specific Effects of Adipogenesis onMSC Function," Stem Cells 35(6), Wiley Periodicals, United States (Jun. 2017).
Office Action mailed Dec. 10, 2019, in United States U.S. Appl. No. 15/911,713, King, S.M., et al., filed Mar. 5, 2018, 14 pages.
Office Action mailed Jul. 12, 2019, in United States U.S. Appl. No. 15/911,713, King, S.M., et al., filed Mar. 5, 2018, 19 pages.

\* cited by examiner

|  | Tamoxifen | | Paclitaxel | | Doxorubicin | |
|---|---|---|---|---|---|---|
|  | IC50 (µM) | % Efficacy | IC50 (µM) | % Efficacy | IC50 (µM) | % Efficacy |
| NHMF | 11.12 | 100 | 0.03691 | 35 | 0.1663 | 88 |
| HUVEC | 0.4255 | 100 | 0.001 | 88 | 0.0128 | 100 |
| SPA | 1.478 | 100 | >10 | 0 | 0.1188 | 98 |
| MCF7 | 1.443 | 100 | 0.0217 | 55 | 0.03458 | 82 |
| 3D tissues | 3.252 | 100 | >10 | 0 | 0.6608 | 82 |

D

Vehicle

A 100 uM Tamoxifen

B

ENGINEERED THREE-DIMENSIONAL BREAST TISSUE, ADIPOSE TISSUE, AND TUMOR DISEASE MODEL

CROSS-REFERENCE TO RELATED APPLICATIONS

This application claims the benefit of U.S. Application Ser. No. 61/975,640, filed Apr. 4, 2014, U.S. Application Ser. No. 61/976,895, filed Apr. 8, 2014, and International Application Serial No. PCT/US2014/041419, filed Jun. 6, 2014, each of which is incorporated by reference in its entirety.

BACKGROUND OF THE INVENTION

Cancer is the second most common cause of death in the U.S., exceeded only by heart disease, accounting for nearly 1 of every 4 deaths. During their lifetime, 1 in 8 American women will develop breast cancer. The American Cancer Society estimates that 232,670 new cases of invasive breast cancer will be diagnosed among women in the U.S. during 2014; about 2,360 new cases are expected in men. An urgent need exists for targeted, safe breast cancer therapeutics, particularly for refractive disease.

SUMMARY OF THE INVENTION

The interaction between cancer cells and the surrounding stromal cells, comprised of fibroblasts, endothelial cells, adipocytes, and immune cells, plays a critical role in cancer initiation, progression, and metastasis. The stromal cells modulate cell signaling, play a structural support role for cancer cells, and influence angiogenesis and metastasis to distant target tissues. As such, stromal cells influence the efficacy of cancer therapeutics. For example, to more accurately model initiation and progression of breast cancer and to more efficiently define targeted therapeutics, the three-dimensional tissue microenvironment must be addressed. Breast stroma, composed of fibroblasts, endothelial cells, and adipocytes, plays a key role in the process of carcinogenesis and metastasis. These cell types secrete extracellular matrix, growth factors, and hormones that affect how therapeutic agents access and target cancer cells.

Two-dimensional cancer cell line cultures suffer from several inadequacies as models for testing anti-cancer agents. First, current two-dimensional cancer models fail to accurately model disease initiation and progression. Second, current two-dimensional cancer models fail to provide a physiologically-relevant stromal milieu. As a result, current two-dimensional cancer models do not adequately demonstrate a native-like response to anti-cancer therapeutic agents. For example, two-dimensional cell culture models typically demonstrate an exaggerated response to therapeutic agents compared to clinical observations.

Moreover, native stroma of many relevant tissues includes adipocytes. In many cases, a native-like tumor disease model with physiologically-relevant stromal milieu includes viable adipocytes. Existing tissue fabrication methodologies lack adequate ability to produce engineered tissues that include viable adipocytes. Differentiated adipocytes are fragile and no previous technology is capable of depositing these important stromal cells without damaging or destroying them.

There is an unmet need for improved preclinical oncology models to overcome hurdles to efficient drug development, including bridging the gap between the use of two-dimensional cell lines and three-dimensional animal models. Specifically, there is an unmet need for development of a model system that incorporates multiple cell types that are physiologically relevant to progression of cancer, including breast cancer, that enables more accurate and efficient screening of targeted therapeutic agents and development of new imaging modalities for earlier detection. The purposes of this disclosure include: 1) to present inventions in which human cancer cells are surrounded by stromal cells, including fibroblasts, adipocytes, and endothelial cells for the purpose of screening targeted cancer therapeutics and developing new imaging agents; and 2) to present inventions in which human breast cancer cells arising from normal epithelia are surrounded by stromal cells, including fibroblasts, adipocytes, and endothelial cells for the purpose of screening targeted cancer therapeutics and developing new imaging agents.

The tumor disease models disclosed herein have several advantages over current screening tools, including the ability to simultaneously measure the effects of small molecules on cancer cells as well as different cell types in the tissue microenvironment. Histomorphological analyses of bioprinted neotissues disclosed herein demonstrated that they were stable and viable for at least 14 days in culture and characterized by clear compartmentalization of adipose, stromal, and epithelial components. During the bioprinting process, robust microvascular networks were created using endothelial cells as a component of the three-dimensional tissue design.

In one aspect, disclosed herein are three-dimensional, engineered, biological breast cancer models comprising: breast stromal tissue, the stromal tissue comprising human mammary fibroblasts, human endothelial cells, and human adipocytes; and breast cancer tumor tissue; the tumor tissue comprising breast cancer cells and human endothelial cells, the tumor tissue surrounded on all sides by the stromal tissue to form the three-dimensional, engineered, biological breast cancer model; provided that the stromal tissue was bioprinted from a stromal bio-ink, the tumor tissue was bioprinted from a tumor bio-ink, or both the stromal tissue and the tumor tissue were bioprinted from their respective bio-inks. In some embodiments, the model is substantially free of pre-formed scaffold. In some embodiments, the breast cancer cells are derived from a breast cancer cell line. In other embodiments, the breast cancer cells are primary cancer cells from a patient tumor. In some embodiments, the breast cancer tumor tissue is completely surrounded on all sides by the breast stromal tissue to form the three-dimensional, engineered, biological breast cancer model.

In another aspect, disclosed herein are methods of fabricating a three-dimensional, engineered, biological breast cancer model, the method comprising: preparing a stromal bio-ink, the stromal bio-ink comprising a plurality of stromal cell types, the stromal cell types comprising: an extrusion compound, human mammary fibroblasts, human endothelial cells, and human adipocytes; preparing a tumor bio-ink, the tumor bio-ink comprising: an extrusion compound and a breast cancer cell type; depositing the stromal bio-ink and the tumor bio-ink such that the tumor bio-ink is embedded in the stromal bio-ink and in contact with the stromal bio-ink on all sides; and maturing the deposited bio-ink in a cell culture media to remove the extrusion compound allow the cells to cohere to form a three-dimensional, engineered, biological breast cancer model. In some embodiments, the bio-ink is deposited by bioprinting. In some embodiments, the breast cancer cell type comprises a breast cancer cell line. In other embodiments, the cancer cell type comprises primary breast cancer cells from a patient tumor. In some embodiments, the cell culture media comprises soluble components that support the growth or maintenance of human fibroblasts, human endothelial cells, adipocytes, and cancer cells. In some embodiments, depositing the stromal bio-ink and the tumor bio-ink further comprises: depositing a first sheet of stromal bio-ink on a surface; depositing a continuous border of stromal bio-ink on the first sheet of stromal bio-ink to define a compartment, the compartment open on one side; depositing a node of tumor bio-ink in the compartment; and depositing a second sheet of stromal bio-ink to close the open side of the compartment.

In another aspect, disclosed herein are methods of identifying a therapeutic agent for cancer in an individual, the method comprising: preparing a stromal bio-ink, the stromal bio-ink comprising a plurality of stromal cell types; preparing a tumor bio-ink, the tumor bio-ink comprising primary cancer cells from the individual; depositing the stromal bio-ink and the tumor bio-ink such that the tumor bio-ink is embedded in the stromal bio-ink and in contact with the stromal bio-ink on all sides; maturing the deposited bio-ink in a cell culture media to allow the cells to cohere to form a three-dimensional, engineered, biological construct; applying a candidate therapeutic agent to the construct; measuring viability of the cancer cells; and selecting a therapeutic agent for the individual based on the measured viability of the cancer cells; provided that at least one component of the construct was deposited by bioprinting. In some embodiments, the stromal bio-ink and the tumor bio-ink are deposited by bioprinting. In some embodiments, the stromal cell types comprise endothelial cells, fibroblasts, and adipocytes. In some embodiments, the cell culture media comprises soluble components that support the growth or maintenance of human fibroblasts, human endothelial cells, adipocytes, and cancer cells. In some embodiments, depositing the stromal bio-ink and the tumor bio-ink further comprises: depositing a first sheet of stromal bio-ink on a surface; depositing a continuous border of stromal bio-ink on the first sheet of stromal bio-ink to define a compartment, the compartment open on one side; depositing a node of tumor bio-ink in the compartment; and depositing a second sheet of stromal bio-ink to close the open side of the compartment.

In another aspect, disclosed herein are methods of identifying a therapeutic agent for breast cancer in an individual, the method comprising: preparing a breast stromal bio-ink, the stromal bio-ink comprising a plurality of breast stromal cell types; preparing a breast tumor bio-ink, the tumor bio-ink comprising primary breast cancer cells from the individual; depositing the stromal bio-ink and the tumor bio-ink such that the tumor bio-ink is embedded in the stromal bio-ink and in contact with the stromal bio-ink on all sides; maturing the deposited bio-ink in a cell culture media to allow the cells to cohere to form a three-dimensional, engineered, breast cancer tumor model; applying a candidate therapeutic agent to the breast cancer tumor model; measuring viability of the breast cancer cells; and selecting a therapeutic agent for the individual based on the measured viability of the breast cancer cells; provided that the stromal bio-ink and the tumor bio-ink were deposited by bioprinting. In some embodiments, the stromal cell types comprise endothelial cells, fibroblasts, and adipocytes. In some embodiments, the cell culture media comprises soluble components that support the growth or maintenance of human fibroblasts, human endothelial cells, adipocytes, and cancer cells. In some embodiments, depositing the stromal bio-ink and the tumor bio-ink further comprises: depositing a first sheet of stromal bio-ink on a surface; depositing a continuous border of stromal bio-ink on the first sheet of stromal bio-ink to define a compartment, the compartment open on one side; depositing a node of tumor bio-ink in the compartment; and depositing a second sheet of stromal bio-ink to close the open side of the compartment.

In another aspect, disclosed herein are arrays of three-dimensional, engineered, biological breast cancer models, each breast cancer model comprising: stromal tissue, the stromal tissue comprising human mammary fibroblasts, human endothelial cells, and human adipocytes; and tumor tissue; the tumor tissue comprising breast cancer cells and human endothelial cells, the tumor tissue surrounded on all sides by the stromal tissue to form each three-dimensional, engineered, biological breast cancer model; provided that the stromal tissue, the tumor tissue, or both the stromal tissue and the tumor tissue were bioprinted; provided that the array is adapted for use in a high throughput assay. In some embodiments, each breast cancer model is substantially free of pre-formed scaffold. In some embodiments, each breast cancer model is in a well of a multi-well plate. In some embodiments, the breast cancer cells are primary cancer cells from a patient tumor. In some embodiments, the tumor tissue is completely surrounded on all sides by the stromal tissue to form each three-dimensional, engineered, biological breast cancer model.

In another aspect, disclosed herein are three-dimensional, engineered, biological tumor models comprising: stromal tissue; and tumor tissue; the tumor tissue comprising cancer cells, the tumor tissue in contact with the stromal tissue to form the three-dimensional, engineered, biological tumor model; provided that the stromal tissue was bioprinted from a stromal bio-ink comprising human preadipocytes exposed to a differentiation signal and the tumor tissue was bioprinted from a tumor bio-ink. In some embodiments, the tumor tissue is surrounded on all sides by the stromal tissue to form the three-dimensional, engineered, biological tumor model. In further embodiments, the tumor tissue is completely surrounded on all sides by the stromal tissue to form the three-dimensional, engineered, biological tumor model. In some embodiments, the model is substantially free of pre-formed scaffold. In some embodiments, the stromal tissue comprises: endothelial cells, fibroblasts, and adipocytes, preadipocytes, or both adipocytes and preadipocytes. In some embodiments, the tumor tissue comprises endothelial cells. In further embodiments, the tumor tissue further comprises fibroblasts and adipocytes, preadipocytes, or both adipocytes and preadipocytes. In some embodiments, the tumor model is a human breast cancer model, the stromal tissue is human breast stroma comprising human mammary fibroblasts, human endothelial cells, and human adipocytes, and the tumor tissue is human breast tumor.

In another aspect, disclosed herein are three-dimensional, engineered, biological tumor models comprising: stromal tissue; and tumor tissue; the tumor tissue comprising cancer cells, the tumor tissue in contact with the stromal tissue to form the three-dimensional, engineered, biological tumor model; provided that the stromal tissue was bioprinted from a stromal bio-ink and the tumor tissue was bioprinted from a tumor bio-ink; provided that the stromal bio-ink and the tumor bio-ink each comprise a reversibly cross-linkable extrusion compound utilized to physically stabilize the tumor model architecture prior to cohesion of the cells. In some embodiments, the tumor tissue is surrounded on all sides by the stromal tissue to form the three-dimensional, engineered, biological tumor model. In further embodiments, the tumor tissue is completely surrounded on all sides by the stromal tissue to form the three-dimensional, engineered, biological tumor model. In some embodiments, the model is substantially free of pre-formed scaffold. In some embodiments, the stromal tissue comprises: endothelial cells, fibroblasts, and adipocytes, preadipocytes, or both adipocytes and preadipocytes. In some embodiments, the tumor tissue comprises endothelial cells. In further embodiments, the tumor tissue further comprises fibroblasts and adipocytes, preadipocytes, or both adipocytes and preadipocytes. In some embodiments, the tumor model is a human breast cancer model, the stromal tissue is human breast stroma comprising human mammary fibroblasts, human endothelial cells, and human adipocytes, and the tumor tissue is human breast tumor.

In another aspect, disclosed herein are methods of fabricating a three-dimensional, engineered, biological tumor model, the method comprising: providing an adipocyte differentiation signal to human preadipocytes; preparing a stromal bio-ink, the stromal bio-ink comprising a plurality of stromal cell types, the stromal cell types comprising the human preadipocytes; preparing a tumor bio-ink, the tumor bio-ink comprising a cancer cell type; depositing the stromal bio-ink and the tumor bio-ink such that the tumor bio-ink is in contact with the stromal bio-ink; and maturing the deposited bio-ink in a cell culture media to allow the cells to cohere to form a three-dimensional, engineered, biological tumor model. In some embodiments, tumor tissue is surrounded on all sides by the stromal tissue. In further embodiments, the tumor tissue is completely surrounded on all sides by the stromal tissue. In some embodiments, the bio-ink is deposited by bioprinting. In some embodiments, the stromal cell types further comprise endothelial cells, fibroblasts, and adipocytes. In some embodiments, the tumor bio-ink further comprises endothelial cells. In further embodiments, the tumor bio-ink further comprises fibroblasts and the preadipocytes. In some embodiments, the stromal bio-ink comprises 50 million cells per mL to 300 million cells per mL. In some embodiments, the tumor bio-ink comprises 50 million cells per mL to 300 million cells per mL. In some embodiments, the cell culture media comprises soluble components that support the growth, maintenance, or differentiation of human fibroblasts, human endothelial cells, adipocytes, and cancer cells. In some embodiments, the tumor model is a human breast cancer model, the stromal bio-ink is human breast stroma bio-ink comprising human mammary fibroblasts, human endothelial cells, and human adipocytes, and the tumor bio-ink is human breast tumor bio-ink.

In another aspect, disclosed herein are methods of fabricating a three-dimensional, engineered, biological tumor model, the method comprising: preparing a stromal bio-ink, the stromal bio-ink comprising a reversibly cross-linkable extrusion compound and a plurality of stromal cell types; preparing a tumor bio-ink, the tumor bio-ink comprising a reversibly cross-linkable extrusion compound and a cancer cell type; depositing the stromal bio-ink and the tumor bio-ink such that the tumor bio-ink is in contact with the stromal bio-ink; crosslinking the extrusion compound to physically stabilize the tumor model architecture prior to cohesion of the cells; and maturing the deposited bio-ink in a cell culture media to remove the extrusion compound and allow the cells to cohere to form a three-dimensional, engineered, biological tumor model. In some embodiments, the tumor tissue is surrounded on all sides by the stromal tissue. In further embodiments, the tumor tissue is completely surrounded on all sides by the stromal tissue. In some embodiments, the bio-ink is deposited by bioprinting. In some embodiments, the extrusion compound comprises alginate. In some embodiments, the extrusion compound is removable by enzymatic digestion. In further embodiments, the method further comprises removing the crosslinked extrusion compound by enzymatic degradation subsequent to cell cohesion. In some embodiments, the stromal cell types comprise endothelial cells, fibroblasts and adipocytes or preadipocytes. In some embodiments, the tumor bio-ink further comprises endothelial cells. In further embodiments, the tumor bio-ink further comprises fibroblasts and adipocytes or preadipocytes. In some embodiments, the stromal bio-ink comprises 50 million cells per mL to 300 million cells per mL. In some embodiments, the tumor bio-ink comprises 50 million cells per mL to 300 million cells per mL. In some embodiments, the cell culture media comprises soluble components that support the growth, maintenance, or differentiation of human fibroblasts, human endothelial cells, adipocytes, and cancer cells. In some embodiments, the tumor model is a human breast cancer model, the stromal bio-ink is human breast stroma bio-ink comprising human mammary fibroblasts, human endothelial cells, and human adipocytes, and the tumor bio-ink is human breast tumor bio-ink.

In another aspect, disclosed herein are arrays of three-dimensional, engineered, biological tumor models, each tumor model comprising: stromal tissue and tumor tissue; the tumor tissue comprising cancer cells, the tumor tissue in contact with the stromal tissue to form each three-dimensional, engineered, biological tumor model; provided that the stromal tissue was bioprinted from a stromal bio-ink comprising human preadipocytes exposed to a differentiation signal; provided that the array is adapted for use in a high throughput assay. In some embodiments, the tumor tissue is surrounded on all sides by the stromal tissue to form each three-dimensional, engineered, biological tumor model. In further embodiments, the tumor tissue is completely surrounded on all sides by the stromal tissue to form each three-dimensional, engineered, biological tumor model. In some embodiments, each tumor model is substantially free of pre-formed scaffold. In some embodiments, each tumor model is in a well of a multi-well plate. In some embodiments, the stromal tissue comprises: endothelial cells, fibroblasts, and adipocytes, preadipocytes, or both adipocytes and preadipocytes. In some embodiments, the tumor tissue comprises endothelial cells. In further embodiments, the tumor tissue further comprises: fibroblasts and adipocytes, preadipocytes, or both adipocytes and preadipocytes. In some embodiments, each tumor model is a human breast cancer model, the stromal tissue is human breast stroma comprising human mammary fibroblasts, human endothelial cells, and human adipocytes, and the tumor tissue is human breast tumor.

In another aspect, disclosed herein are arrays of three-dimensional, engineered, biological tumor models, each tumor model comprising: stromal tissue and tumor tissue; the tumor tissue comprising cancer cells, the tumor tissue in contact with the stromal tissue to form each three-dimensional, engineered, biological tumor model; provided that the stromal tissue was bioprinted from a stromal bio-ink comprising a reversibly crosslinkable extrusion compound and the tumor tissue was bioprinted from a tumor bio-ink comprising a reversibly crosslinkable extrusion compound; provided that the array is adapted for use in a high throughput assay. In some embodiments, the tumor tissue is surrounded on all sides by the stromal tissue to form each three-dimensional, engineered, biological tumor model. In further embodiments, the tumor tissue is completely surrounded on all sides by the stromal tissue to form each three-dimensional, engineered, biological tumor model. In some embodiments, each tumor model is substantially free of pre-formed scaffold. In some embodiments, each tumor model is in a well of a multi-well plate. In some embodiments, the stromal tissue comprises: endothelial cells, fibroblasts, and adipocytes, preadipocytes, or both adipocytes and preadipocytes. In some embodiments, the tumor tissue comprises endothelial cells. In further embodiments, the tumor tissue further comprises: fibroblasts and adipocytes, preadipocytes, or both adipocytes and preadipocytes. In some embodiments, each tumor model is a human breast cancer model, the stromal tissue is human breast stroma comprising human mammary fibroblasts, human endothelial cells, and human adipocytes, and the tumor tissue is human breast tumor.

DETAILED DESCRIPTION OF THE INVENTION

Figure 1:
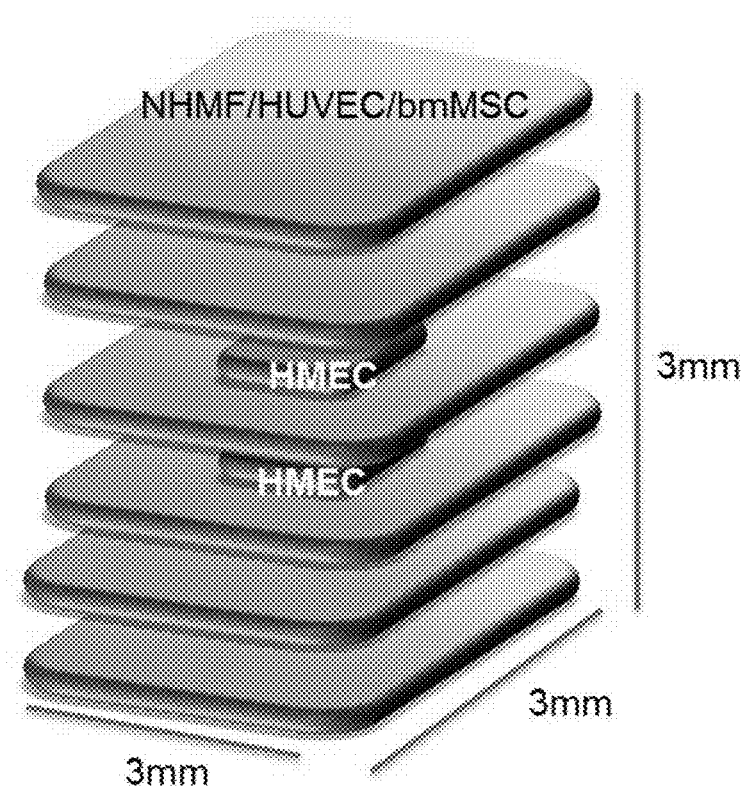
FIG. 1 shows a non-limiting example of a schematic diagram depicting the construction of a bioprinted breast tissue construct; in this case, a construct that is substantially a six-layered cube with an inner region of epithelial cells surrounded by an outer region of fibroblasts, endothelial cells, and bone marrow derived mesenchymal stem cells.

In some embodiments, the tumor disease models disclosed herein are breast cancer tumor models composed of two major parts 1) a stromal compartment comprising human mammary fibroblasts, endothelial cells, and bone marrow-derived mesenchymal cells or preadipocytes; and 2) an epithelial compartment comprising human mammary epithelium and/or breast adenocarcinoma cells. In further embodiments, the cells are deposited using a Novogen Bioprinter® (Organovo; San Diego, Calif.) in such a way that the epithelial/adenocarcinoma compartment is surrounded on all sides by the stromal compartment. In still further embodiments, structures are created either by spatially-controlled deposition of bio-ink or cells mixed with support biomaterials such as hydrogels, which are later degraded or removed.

Described herein, in certain embodiments, are three-dimensional, engineered, biological breast cancer models comprising: breast stromal tissue, the stromal tissue comprising human mammary fibroblasts, human endothelial cells, and human adipocytes; and breast cancer tumor tissue; the tumor tissue comprising breast cancer cells and human endothelial cells, the tumor tissue surrounded on all sides by the stromal tissue to form the three-dimensional, engineered, biological breast cancer model; provided that the stromal tissue was bioprinted from a stromal bio-ink, the tumor tissue was bioprinted from a tumor bio-ink, or both the stromal tissue and the tumor tissue were bioprinted from their respective bio-inks.

Also described herein, in certain embodiments, are methods of fabricating a three-dimensional, engineered, biological breast cancer model, the method comprising: preparing a stromal bio-ink, the stromal bio-ink comprising a plurality of stromal cell types, the stromal cell types comprising: an extrusion compound, human mammary fibroblasts, human endothelial cells, and human adipocytes; preparing a tumor bio-ink, the tumor bio-ink comprising: an extrusion compound and a breast cancer cell type; depositing the stromal bio-ink and the tumor bio-ink such that the tumor bio-ink is embedded in the stromal bio-ink and in contact with the stromal bio-ink on all sides; and maturing the deposited bio-ink in a cell culture media to remove the extrusion compound allow the cells to cohere to form a three-dimensional, engineered, biological breast cancer model.

Also described herein, in certain embodiments, are methods of identifying a therapeutic agent for cancer in an individual, the method comprising: preparing a stromal bio-ink, the stromal bio-ink comprising a plurality of stromal cell types; preparing a tumor bio-ink, the tumor bio-ink comprising primary cancer cells from the individual; depositing the stromal bio-ink and the tumor bio-ink such that the tumor bio-ink is embedded in the stromal bio-ink and in contact with the stromal bio-ink on all sides; maturing the deposited bio-ink in a cell culture media to allow the cells to cohere to form a three-dimensional, engineered, biological construct; applying a candidate therapeutic agent to the construct; measuring viability of the cancer cells; and selecting a therapeutic agent for the individual based on the measured viability of the cancer cells; provided that at least one component of the construct was deposited by bioprinting.

Also described herein, in certain embodiments, are methods of identifying a therapeutic agent for breast cancer in an individual, the method comprising: preparing a breast stromal bio-ink, the stromal bio-ink comprising a plurality of breast stromal cell types; preparing a breast tumor bio-ink, the tumor bio-ink comprising primary breast cancer cells from the individual; depositing the stromal bio-ink and the tumor bio-ink such that the tumor bio-ink is embedded in the stromal bio-ink and in contact with the stromal bio-ink on all sides; maturing the deposited bio-ink in a cell culture media to allow the cells to cohere to form a three-dimensional, engineered, breast cancer tumor model; applying a candidate therapeutic agent to the breast cancer tumor model; measuring viability of the breast cancer cells; and selecting a therapeutic agent for the individual based on the measured viability of the breast cancer cells; provided that the stromal bio-ink and the tumor bio-ink were deposited by bioprinting.

Also described herein, in certain embodiments, are arrays of three-dimensional, engineered, biological breast cancer models, each breast cancer model comprising: stromal tissue, the stromal tissue comprising human mammary fibroblasts, human endothelial cells, and human adipocytes; and tumor tissue; the tumor tissue comprising breast cancer cells and human endothelial cells, the tumor tissue surrounded on all sides by the stromal tissue to form each three-dimensional, engineered, biological breast cancer model; provided that the stromal tissue, the tumor tissue, or both the stromal tissue and the tumor tissue were bioprinted; provided that the array is adapted for use in a high throughput assay.

Also described herein, in certain embodiments, are three-dimensional, engineered, biological tumor models comprising: stromal tissue; and tumor tissue; the tumor tissue comprising cancer cells, the tumor tissue in contact with the stromal tissue to form the three-dimensional, engineered, biological tumor model; provided that the stromal tissue was bioprinted from a stromal bio-ink comprising human pre-adipocytes exposed to a differentiation signal and the tumor tissue was bioprinted from a tumor bio-ink.

Also described herein, in certain embodiments, are three-dimensional, engineered, biological tumor models comprising: stromal tissue; and tumor tissue; the tumor tissue comprising cancer cells, the tumor tissue in contact with the stromal tissue to form the three-dimensional, engineered, biological tumor model; provided that the stromal tissue was bioprinted from a stromal bio-ink and the tumor tissue was bioprinted from a tumor bio-ink; provided that the stromal bio-ink and the tumor bio-ink each comprise a reversibly cross-linkable extrusion compound utilized to physically stabilize the tumor model architecture prior to cohesion of the cells.

Also described herein, in certain embodiments, are methods of fabricating a three-dimensional, engineered, biological tumor model, the method comprising: providing an adipocyte differentiation signal to human preadipocytes; preparing a stromal bio-ink, the stromal bio-ink comprising a plurality of stromal cell types, the stromal cell types comprising the human preadipocytes; preparing a tumor bio-ink, the tumor bio-ink comprising a cancer cell type; depositing the stromal bio-ink and the tumor bio-ink such that the tumor bio-ink is in contact with the stromal bio-ink; and maturing the deposited bio-ink in a cell culture media to allow the cells to cohere to form a three-dimensional, engineered, biological tumor model.

Also described herein, in certain embodiments, are methods of fabricating a three-dimensional, engineered, biological tumor model, the method comprising: preparing a stromal bio-ink, the stromal bio-ink comprising a reversibly cross-linkable extrusion compound and a plurality of stromal cell types; preparing a tumor bio-ink, the tumor bio-ink comprising a reversibly cross-linkable extrusion compound and a cancer cell type; depositing the stromal bio-ink and the tumor bio-ink such that the tumor bio-ink is in contact with the stromal bio-ink; crosslinking the extrusion compound to physically stabilize the tumor model architecture prior to cohesion of the cells; and maturing the deposited bio-ink in a cell culture media to remove the extrusion compound and allow the cells to cohere to form a three-dimensional, engineered, biological tumor model.

Also described herein, in certain embodiments, are arrays of three-dimensional, engineered, biological tumor models, each tumor model comprising: stromal tissue and tumor tissue; the tumor tissue comprising cancer cells, the tumor tissue in contact with the stromal tissue to form each three-dimensional, engineered, biological tumor model; provided that the stromal tissue was bioprinted from a stromal bio-ink comprising human preadipocytes exposed to a differentiation signal; provided that the array is adapted for use in a high throughput assay.

Also described herein, in certain embodiments, are arrays of three-dimensional, engineered, biological tumor models, each tumor model comprising: stromal tissue and tumor tissue; the tumor tissue comprising cancer cells, the tumor tissue in contact with the stromal tissue to form each three-dimensional, engineered, biological tumor model; provided that the stromal tissue was bioprinted from a stromal bio-ink comprising a reversibly crosslinkable extrusion compound and the tumor tissue was bioprinted from a tumor bio-ink comprising a reversibly crosslinkable extrusion compound; provided that the array is adapted for use in a high throughput assay.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As used herein, "adipocyte" (also known as a "lipocyte" or "fat cell") refers to the cells that primarily compose adipose tissue, which is specialized in storing energy as fat.

As used herein, "preadipocyte" refers to any cell that can be stimulated to form adipocytes.

As used herein, "stroma" refers to the connective, supportive framework of a biological cell, tissue, or organ.

As used herein, "tissue" means an aggregate of cells.

As used herein, "bio-ink" means a liquid, semi-solid, or solid composition for use in bioprinting. In some embodiments, bio-ink comprises cell solutions, cell aggregates, cell-comprising gels, multicellular bodies, or tissues. In some embodiments, the bio-ink additionally comprises non-cellular materials that provide specific biomechanical properties that enable bioprinting. In some embodiments the bio-ink comprises an extrusion compound.

As used herein, "bioprinting" means utilizing three-dimensional, precise deposition of cells (e.g., cell solutions, cell-containing gels, cell suspensions, cell concentrations, multicellular aggregates, multicellular bodies, etc.) via methodology that is compatible with an automated or semi-automated, computer-aided, three-dimensional prototyping device (e.g., a bioprinter).

As used herein, "scaffold" refers to synthetic scaffolds such as polymer scaffolds and porous hydrogels, non-synthetic scaffolds such as pre-formed extracellular matrix layers, dead cell layers, and decellularized tissues, and any other type of pre-formed scaffold that is integral to the physical structure of the engineered tissue and not able to be removed from the tissue without damage/destruction of said tissue. In further embodiments, decellularized tissue scaffolds include decellularized native tissues or decellularized cellular material generated by cultured cells in any manner; for example, cell layers that are allowed to die or are decellularized, leaving behind the ECM they produced while living. The term "scaffoldless," therefore, is intended to imply that scaffold is not an integral part of the engineered tissue at the time of use, either having been removed or remaining as an inert component of the engineered tissue. "Scaffoldless" is used interchangeably with "scaffold-free" and "free of pre-formed scaffold."

As used herein, "assay" means a procedure for testing or measuring the presence or activity of a substance (e.g., a chemical, molecule, biochemical, protein, hormone, or drug, etc.) in an organic or biologic sample (e.g., cell aggregate, tissue, organ, organism, etc.).

Bioprinting

In some embodiments, at least one component of the engineered tissues, constructs, or an array thereof, is bioprinted. In further embodiments, bioprinted constructs are made with a method that utilizes a rapid prototyping technology based on three-dimensional, automated, computer-aided deposition of cells, including cell solutions, cell suspensions, cell-comprising gels or pastes, cell concentrations, multicellular bodies (e.g., cylinders, spheroids, ribbons, etc.), and, optionally, confinement material onto a biocompatible support surface (e.g., composed of hydrogel and/or a porous membrane) by a three-dimensional delivery device (e.g., a bioprinter). As used herein, in some embodiments, the term "engineered," when used to refer to tissues or constructs means that cells, cell solutions, cell suspensions, cell-comprising gels or pastes, cell concentrates, multicellular aggregates, and layers thereof are positioned to form three-dimensional structures by a computer-aided device (e.g., a bioprinter) according to a computer script. In further embodiments, the computer script is, for example, one or more computer programs, computer applications, or computer modules including executable instructions. In still further embodiments, three-dimensional tissue structures form through the post-printing fusion of cells or multicellular bodies which, in some cases, is similar to self-assembly phenomena in early morphogenesis.

While a number of methods are available to arrange cells, cell aggregates, and cell-containing materials on a biocompatible surface to produce a three-dimensional structure, including manual placement, positioning by an automated, computer-aided machine such as a bioprinter is advantageous. Advantages of delivery of cells, cell aggregates, and cell-containing materials with this technology include rapid, accurate, and reproducible placement of cells or multicellular bodies to produce constructs exhibiting planned or pre-determined orientations or patterns of cells, cell aggregates and/or layers thereof with various compositions. Advantages also include assured high cell density, while minimizing cell damage. Adipocytes are particularly susceptible to damage by shear force and other biomechanical stress; thus the bioprinting process described herein provides a distinct advantage over alternative technologies as highlighted by the favorable viability of the adipose cells in bioprinted tissues as highlighted in Examples 2-4.

In some embodiments, the method of bioprinting is continuous and/or substantially continuous. A non-limiting example of a continuous bioprinting method is to dispense bio-ink (i.e., cells, cells combined with an excipient or extrusion compound, or aggregates of cells) from a bioprinter via a dispense tip (e.g., a syringe, needle, capillary tube, etc.) connected to a reservoir of bio-ink. In further non-limiting embodiments, a continuous bioprinting method is to dispense bio-ink in a repeating pattern of functional units. In various embodiments, a repeating functional unit has any suitable geometry, including, for example, circles, squares, rectangles, triangles, polygons, and irregular geometries, thereby resulting in one or more tissue layers with planar geometry achieved via spatial patterning of distinct bio-inks and/or void spaces. In further embodiments, a repeating pattern of bioprinted function units comprises a layer and a plurality of layers are bioprinted adjacently (e.g., stacked) to form an engineered tissue with laminar geometry. In various embodiments, 2, 3, 4, 5, 6, 7, 8, 9, 10, 11, 12, 13, 14, 15, or more layers are bioprinted adjacently (e.g., stacked) to form an engineered tissue. In further embodiments, one or more layers of a tissue with laminar geometry also has planar geometry.

In some embodiments, continuous bioprinting facilitates printing larger tissues from a large reservoir of bio-ink, optionally using a syringe mechanism. Continuous bioprinting is also a convenient way to co-print spatially-defined boundaries, using an extrusion compound, a hydrogel, a polymer, bio-ink, or any printable material that is capable of retaining its shape post-printing; wherein the boundaries that are created are optionally filled in via the bioprinting of one or more bio-inks, thereby creating a mosaic tissue with spatially-defined planar geometry.

In some embodiments, methods in continuous bioprinting involve optimizing and/or balancing parameters such as print height, pump speed, robot speed, or combinations thereof independently or relative to each other. In certain cases, the bioprinter head speed for deposition was 3 mm/s, with a dispense height of 0.5 mm for the first layer and dispense height was increased 0.4 mm for each subsequent layer. In some embodiments, the dispense height is approximately equal to the diameter of the bioprinter dispense tip. Without limitation a suitable and/or optimal dispense distance does not result in material flattening or adhering to the dispensing needle. In various embodiments, the bioprinter dispense tip has an inner diameter of about, 20, 50, 100, 150, 200, 250, 300, 350, 400, 450, 500, 550, 600, 650, 700, 750, 800, 850, 900, 950, 1000 µm, or more, including increments therein. In various embodiments, the bio-ink reservoir of the bioprinter has a volume of about 0.05, 0.1, 0.5, 1, 2, 3, 4, 5, 6, 7, 8, 9, 10, 15, 20, 25, 30, 35, 40, 45, 50, 55, 60, 65, 70, 75, 80, 85, 90, 95, 100 cubic centimeters, or more, including increments therein. The pump speed is, in some cases, suitable and/or optimal when the residual pressure build-up in the system is low. Favorable pump speeds, in some cases, depend on the ratio between the cross-sectional areas of the reservoir and dispense needle with larger ratios requiring lower pump speeds. In some embodiments, a suitable and/or optimal print speed enables the deposition of a uniform line without affecting the mechanical integrity of the material.

The inventions disclosed herein include business methods. In some embodiments, the speed and scalability of the techniques and methods disclosed herein are utilized to design, build, and operate industrial and/or commercial facilities for production of engineered breast tissues and/or tumor disease models for use in generation of cell-based tools for research and development, such as in vitro assays. In further embodiments, the engineered tissues and/or models and arrays thereof are produced, stored, distributed, marketed, advertised, and sold as, for example, cellular arrays (e.g., microarrays or chips), tissue arrays (e.g., microarrays or chips), and kits for biological assays and high-throughput drug screening. In other embodiments, the engineered tissues and/or models and arrays thereof are produced and utilized to conduct biological assays and/or drug screening as a service.

Bio-Ink

Disclosed herein, in certain embodiments, are three-dimensional, living tissues, including adipose tissues, breast tissues, tumor models, arrays thereof, and methods that comprise bioprinting cells. In some embodiments, cells are bioprinted by depositing or extruding bio-ink from a bioprinter. In some embodiments, "bio-ink" includes liquid, semi-solid, or solid compositions comprising a plurality of cells. In some embodiments, bio-ink comprises liquid or semi-solid cell solutions, cell suspensions, or cell concentrations. In further embodiments, a cell solution, suspension, or concentration comprises a liquid or semi-solid (e.g., viscous) carrier and a plurality of cells. In still further embodiments, the carrier is a suitable cell nutrient media, such as those described herein. In some embodiments, bio-ink comprises a plurality of cells that optionally cohere into multicellular aggregates prior to bioprinting. In further embodiments, bio-ink comprises a plurality of cells and is bioprinted to produce a specific planar and/or laminar geometry; wherein cohesion of the individual cells within the bio-ink takes place before, during and/or after bioprinting.

In some embodiments, the bio-ink is produced by collecting a plurality of cells in a fixed volume; wherein the cellular component(s) represent at least about 30% and at most about 100% of the total volume. In some embodiments, bio-ink comprises semi-solid or solid multicellular aggregates or multicellular bodies. In further embodiments, the bio-ink is produced by 1) mixing a plurality of cells or cell aggregates and a biocompatible liquid or gel in a predetermined ratio to result in bio-ink, and 2) compacting the bio-ink to produce the bio-ink with a desired cell density and viscosity. In some embodiments, the compacting of the bio-ink is achieved by centrifugation, tangential flow filtration ("TFF"), or a combination thereof.

In some embodiments, the bio-inks disclosed herein are characterized by high cellularity by volume, e.g., a high concentration of living cells. In further embodiments, the bio-ink comprise at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400 or more million cells per milliliter of solution. In a particular embodiment, the bio-inks comprise about 50 to about 300 million cells/mL. In some embodiments, bio-inks that have high cellularity by volume are used to bioprint engineered tissues and constructs with high cell density. In further embodiments, the engineered tissues and constructs are at least about 30, 35, 40, 45, 50, 55, 60, 65, 70, 75, 80 or more percent cells.

In some embodiments, the compacting of the bio-ink results in a composition that is extrudable, allowing formation of multicellular aggregates or multicellular bodies. In some embodiments, "extrudable" means able to be shaped by forcing (e.g., under pressure) through a nozzle or orifice (e.g., one or more holes or tubes). In some embodiments, the compacting of the bio-ink results from growing the cells to a suitable density. The cell density necessary for the bio-ink will vary with the cells being used and the tissue or organ being produced.

In some embodiments, the cells of the bio-ink are cohered and/or adhered. In some embodiments, "cohere," "cohered," and "cohesion" refer to cell-cell adhesion properties that bind cells, multicellular aggregates, multicellular bodies, and/or layers thereof. In further embodiments, the terms are used interchangeably with "fuse," "fused," and "fusion." In some embodiments, the bio-ink additionally comprises support material, cell culture medium (or supplements thereof), extracellular matrix (or components thereof), cell adhesion agents, cell death inhibitors, anti-apoptotic agents, antioxidants, extrusion compounds, and combinations thereof.

In some embodiments, the bio-ink comprises cancer cells (e.g., tumor cells). In further embodiments, the cancer cells are cells of one or more cell lines. In other embodiments, the cancer cells are primary cancer cells derived from the tumor of a patient. In some embodiments, the bio-ink comprises stromal cells such as endothelial cells, fibroblasts, and adipocytes and/or preadipocytes.

In some embodiments, the bio-ink is a bio-gel suitable for non-bioprinting fabrication methodologies. In some embodiments, the bio-gel comprises cancer cells (e.g., tumor cells). In further embodiments, the cancer cells are cells of one or more cell lines. In other embodiments, the cancer cells are primary cancer cells derived from the tumor of a patient. In some embodiments, the bio-gel comprises stromal cells such as endothelial cells, fibroblasts, and adipocytes and/or preadipocytes.

Extrusion Compounds

In some embodiments, the bio-ink comprises an extrusion compound (i.e., a compound that modifies the extrusion properties of the bio-ink). Examples of extrusion compounds include, but are not limited to gels, hydrogels, peptide hydrogels, amino acid-based gels, surfactant polyols (e.g., Pluronic F-127 or PF-127), thermo-responsive polymers, hyaluronates, alginates, extracellular matrix components (and derivatives thereof), collagens, gelatin, other biocompatible natural or synthetic polymers, nanofibers, and self-assembling nanofibers. In some embodiments, extrusion compounds are removed by physical, chemical, or enzymatic means subsequent to bioprinting, subsequent to cohesion of the bioprinted cells, or subsequent to maturation of the bioprinted construct.

Suitable hydrogels include those derived from collagen, hyaluronate, hyaluronan, fibrin, alginate, agarose, chitosan, and combinations thereof. In other embodiments, suitable hydrogels are synthetic polymers. In further embodiments, suitable hydrogels include those derived from poly(acrylic acid) and derivatives thereof, poly(ethylene oxide) and copolymers thereof, poly(vinyl alcohol), polyphosphazene, and combinations thereof. In various specific embodiments, the confinement material is selected from: hydrogel, Novo-Gel® (Organovo, Inc.; San Diego, Calif.), agarose, alginate, gelatin, Matrigel™, hyaluronan, poloxamer, peptide hydrogel, poly(isopropyl n-polyacrylamide), polyethylene glycol diacrylate (PEG-DA), hydroxyethyl methacrylate, polydimethylsiloxane, polyacrylamide, poly(lactic acid), silicon, silk, or combinations thereof.

In some embodiments, hydrogel-based extrusion compounds are crosslinkable gels. In further embodiments, crosslinkable gels include those crosslinkable by chemical means. For example, in some embodiments, suitable hydrogels include alginate-containing crosslinkable hydrogels. In various embodiments, suitable hydrogels comprise about 0.1, 0.5, 1, 2, 3, 4, 5, 6, 7, 8, 9, 10, or more percent alginate. In some embodiments, following bioprinting, constructs are optionally incubated with an agent to chemically crosslink the hydrogel, such as a solution of $CaCl_2$, in order preserve a bioprinted architecture prior to cohesion of the cells. Further, in some embodiments, the bioprinted constructs are optionally incubated with alginate lyase to enzymatically degrade the hydrogel. In further embodiments, the bioprinted constructs are optionally incubated with alginate lyase at a concentration of about 0.2-0.5 mg/ml to enzymatically degrade the hydrogel.

In some embodiments, suitable hydrogels include gelatin. In various embodiments, suitable hydrogels comprise about 1, 2, 3, 4, 5, 6, 7, 8, 9, 10, 11, 12, 13, 14, 15, 16, 17, 18, 19, 20 or more percent gelatin.

In some embodiments, the concentration of gelatin is about 5-15% and the concentration of alginate is about 0.5-5% in the extrusion compound or hydrogel. In a particular embodiment, the concentration of gelatin is 10% and the concentration of alginate is 1% in the extrusion compound or hydrogel.

In some embodiments, hydrogel-based extrusion compounds are thermoreversible gels (also known as thermo-responsive gels or thermogels). In some embodiments, a suitable thermoreversible hydrogel is not a liquid at room temperature. In specific embodiments, the gelation temperature (Tgel) of a suitable hydrogel is about 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., including increments therein. In certain embodiments, the Tgel of a suitable hydrogel is about 10° C. to about 40° C. In further embodiments, the Tgel of a suitable hydrogel is about 20° C. to about 30° C. In some embodiments, the bio-ink (e.g., comprising hydrogel, one or more cell types, and other additives, etc.) described herein is not a liquid at room temperature. In some embodiments, a suitable thermoreversible hydrogel is not a liquid at mammalian body temperature. In specific embodiments, the gelation temperature (Tgel) of a suitable hydrogel is about 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 41° C., 43° C., 44° C., 45° C., 46° C., 47° C., 48° C., 49° C., 50° C., 51° C., 52° C., including increments therein. In certain embodiments, the Tgel of a suitable hydrogel is about 22° C. to about 52° C. In further embodiments, the Tgel of a suitable hydrogel is about 32° C. to about 42° C. In some embodiments, the bio-ink (e.g., comprising hydrogel, one or more cell types, and other additives, etc.) described herein is not a liquid at mammalian body temperature. In specific embodiments, the gelation temperature (Tgel) of a bio-ink described herein is about 10° C., about 15° C., about 20° C., about 25° C., about 30° C., about 35° C., about 40° C., about 45° C., about 50° C., about 55° C., including increments therein.

Polymers composed of polyoxypropylene and polyoxyethylene form thermoreversible gels when incorporated into aqueous solutions. These polymers have the ability to change from the liquid state to the gel state at temperatures maintainable in a bioprinter apparatus. The liquid state-to-gel state phase transition is dependent on the polymer concentration and the ingredients in the solution.

In some embodiments, the viscosity of the hydrogels and bio-inks presented herein is measured by any means described. For example, in some embodiments, an LVDV-II+CP Cone Plate Viscometer and a Cone Spindle CPE-40 are used to calculate the viscosity of the hydrogels and bio-inks. In other embodiments, a Brookfield (spindle and cup) viscometer is used to calculate the viscosity of the hydrogels and bio-inks. In some embodiments, the viscosity ranges referred to herein are measured at room temperature. In other embodiments, the viscosity ranges referred to herein are measured at body temperature (e.g., at the average body temperature of a healthy human).

In further embodiments, the hydrogels and/or bio-inks are characterized by having a viscosity of between about 500 and 1,000,000 centipoise, between about 750 and 1,000,000 centipoise; between about 1000 and 1,000,000 centipoise; between about 1000 and 400,000 centipoise; between about 2000 and 100,000 centipoise; between about 3000 and 50,000 centipoise; between about 4000 and 25,000 centipoise; between about 5000 and 20,000 centipoise; or between about 6000 and 15,000 centipoise.

In some embodiments, the non-cellular components of the bio-ink (e.g., extrusion compounds, etc.) are removed prior to use. In further embodiments, the non-cellular components are, for example, hydrogels, peptide hydrogels, amino acid-based gels, surfactant polyols, thermo-responsive polymers, hyaluronates, alginates, collagens, or other biocompatible natural or synthetic polymers. In still further embodiments, the non-cellular components are removed by physical, chemical, or enzymatic means. In some embodiments, a proportion of the non-cellular components remain associated with the cellular components at the time of use.

Pre-Formed Scaffold

In some embodiments, disclosed herein are engineered tissues and tumor models that are free or substantially free of any pre-formed scaffold. In further embodiments, "scaffold" refers to synthetic scaffolds such as polymer scaffolds and porous hydrogels, non-synthetic scaffolds such as pre-formed extracellular matrix layers, dead cell layers, and decellularized tissues, and any other type of pre-formed scaffold that is integral to the physical structure of the engineered tissue and/or organ and not removed from the tissue and/or organ. In still further embodiments, decellularized tissue scaffolds include decellularized native tissues or decellularized cellular material generated by cultured cells in any manner; for example, cell layers that are allowed to die or are decellularized, leaving behind the ECM they produced while living.

In some embodiments, the engineered tissues and tumor models (including arrays of the same) do not utilize any pre-formed scaffold, e.g., for the formation of the tissue, any layer of the tissue, or formation of the tissue's shape. As a non-limiting example, the engineered breast and adipose tissues of the present disclosure do not utilize any pre-formed, synthetic scaffolds such as polymer scaffolds, pre-formed extracellular matrix layers, or any other type of pre-formed scaffold at the time of manufacture or at the time of use. In some embodiments, the engineered breast and adipose tissues are substantially free of any pre-formed scaffolds. In further embodiments, the cellular components of the tissues contain a detectable, but trace or trivial amount of scaffold, e.g., less than 2.0%, less than 1.0%, less than 0.5%, or less than 0.1% of the total composition. In still further embodiments, trace or trivial amounts of scaffold are insufficient to affect long-term behavior of the tissue, or array thereof, or interfere with its primary biological function. In additional embodiments, scaffold components are removed post-printing, by physical, chemical, or enzymatic methods, yielding an engineered tissue that is free or substantially-free of scaffold components.

Arrays

In some embodiments, disclosed herein are arrays of engineered breast tissues and arrays of engineered tumor models (including breast cancer tumor models). In some embodiments, an "array" is a scientific tool including an association of multiple elements spatially arranged to allow a plurality of tests to be performed on a sample, one or more tests to be performed on a plurality of samples, or both. In some embodiments, the arrays are adapted for, or compatible with, screening methods and devices, including those associated with medium- or high-throughput screening. In further embodiments, an array allows a plurality of tests to be performed simultaneously. In further embodiments, an array allows a plurality of samples to be tested simultaneously. In some embodiments, the arrays are cellular microarrays. In further embodiments, a cellular microarray is a laboratory tool that allows for the multiplex interrogation of living cells on the surface of a solid support. In other embodiments, the arrays are tissue microarrays. In further embodiments, tissue microarrays include a plurality of separate tissues or tissue samples assembled in an array to allow the performance of multiple biochemical, metabolic, molecular, or histological analyses.

In some embodiments, the engineered tissues and/or tumor models each exist in a well of a biocompatible multi-well container. In some embodiments, each tissue is placed into a well. In other embodiments, each tissue is bioprinted into a well. In further embodiments, the wells are coated. In various further embodiments, the wells are coated with one or more of: a biocompatible hydrogel, one or more proteins, one or more chemicals, one or more peptides, one or more antibodies, and one or more growth factors, including combinations thereof. In some embodiments, the wells are coated with NovoGel®. In other embodiments, the wells are coated with agarose. In some embodiments, each tissue exists on a porous, biocompatible membrane within a well of a biocompatible multi-well container. In some embodiments, each well of a multi-well container contains two or more tissues.

In some embodiments, the engineered tissues and/or tumor models are secured to a biocompatible surface on one or more sides. Many methods are suitable to secure a tissue to a biocompatible surface. In various embodiments, a tissue is suitably secured to a biocompatible surface, for example, along one or more entire sides, only at the edges of one or more sides, or only at the center of one or more sides. In various further embodiments, a tissue is suitably secured to a biocompatible surface with a holder or carrier integrated into the surface or associated with the surface. In various further embodiments, a tissue is suitably secured to a biocompatible surface with one or more pinch-clamps or plastic nubs integrated into the surface or associated with the surface. In some embodiments, a tissue is suitably secured to a biocompatible surface by cell-attachment to a porous membrane. In some embodiments, the engineered tissues and/or tumor models are held in an array configuration by affixation to a biocompatible surface on one or more sides. In further embodiments, the tissue is affixed to a biocompatible surface on 1, 2, 3, 4, or more sides. In some embodiments, the biocompatible surface any surface that does not pose a significant risk of injury or toxicity to the tissue or an organism contacting the tissue. In further embodiments, the biocompatible surface is any surface suitable for traditional tissue culture methods. Suitable biocompatible surfaces include, by way of non-limiting examples, treated plastics, membranes, porous membranes, coated membranes, coated plastics, metals, coated metals, glass, treated glass, and coated glass, wherein suitable coatings include hydrogels, ECM components, chemicals, proteins, etc., and coatings or treatments provide a means to stimulate or prevent cell and tissue adhesion to the biocompatible surface.

In some embodiments, the arrays of engineered tissues and/or tumor models comprise an association of two or more elements. In various embodiments, the arrays comprise an association of 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, or 500 elements, including increments therein. In further embodiments, each element comprises one or more cells, multicellular aggregates, tissues, tumor models, or combinations thereof.

In some embodiments, the arrays of engineered tissues and/or tumor models comprise multiple elements spatially arranged in a pre-determined pattern. In further embodiments, the pattern is any suitable spatial arrangement of elements. In various embodiments, patterns of arrangement include, by way of non-limiting examples, a two-dimensional grid, a three-dimensional grid, one or more lines, arcs, or circles, a series of rows or columns, and the like. In further embodiments, the pattern is chosen for compatibility with medium- or high-throughput biological assay or screening methods or devices.

In various embodiments, the cell types and/or source of the cells used to fabricate one or more tissues or tumor models in an array are selected based on a specific research goal or objective. In further various embodiments, the specific tissues or tumor models in an array are selected based on a specific research goal or objective. In some embodiments, one or more specific engineered tissues are included in an array to facilitate investigation of a particular disease or condition. In some embodiments, one or more specific engineered tissues are included in an array to facilitate investigation of a disease or a condition of a particular subject. In further embodiments, one or more specific engineered tissues within the array are generated with one or more cell types derived from two or more distinct human donors. In some embodiments, each tissue within the array is substantially similar with regard to cell types, sources of cells, layers of cells, ratios of cells, and methods of construction, size, shape, and the like. In other embodiments, one or more of the tissues within the array is unique with regard to cell types, sources of cells, layers of cells, ratios of cells, methods of construction, size, shape, and the like.

In some embodiments, each tissue and/or tumor model within the array is maintained independently in culture. In further embodiments, the culture conditions of each tissue within the array are such that they are isolated from the other tissues and cannot exchange media or factors soluble in the media. In other embodiments, two or more individual tissues within the array exchange soluble factors. In further embodiments, the culture conditions of two or more individual tissues within the array are such that they exchange media and factors soluble in the media with other tissues. In various embodiments, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, 300, or more of the tissues within the array, including increments therein, exchange media and/or soluble factors. In other various embodiments, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of the tissues within the array, including increments therein, exchange media and/or soluble factors.

Engineered Breast Tissues

Described herein, in some embodiments are three-dimensional, engineered, biological breast tissues comprising breast cells. Many breast cells are suitable for inclusion in the engineered breast tissues. For example, in various embodiments, the engineered breast tissues suitably include one or more of: fibroblasts, endothelial cells, epithelial cells, and adipocytes. In various embodiments, the cells are vertebrate cells, mammalian cells, human cells, or combinations thereof. In further embodiments, the engineered breast tissues suitably include one or more of: human mammary fibroblasts, human endothelial cells, human mammary epithelial cells, and human adipocytes. In still further embodiments, the engineered breast tissues suitably include each of: human mammary fibroblasts, human endothelial cells, human mammary epithelial cells, and human adipocytes.

In some embodiments, the human endothelial cells are human umbilical vein endothelial cells. In some embodiments, the adipocytes are derived from precursor cells such as mesenchymal stem cells including bone marrow derived mesenchymal stem cells. In further embodiments, the adipocytes are derived from precursor cells such as preadipocytes. In such cases, the adipocyte precursor cells are exposed to a differentiation signal prior to use in the preparation of a bio-ink or use in bioprinting. In further embodiments, the adipocyte precursor cells are exposed to a differentiation signal to partially pre-differentiate the cells prior to use in the preparation of a bio-ink or use in bioprinting. In still further embodiments, the adipocyte precursor cells or preadipocytes complete differentiation post-bioprinting. In some embodiments, the human adipocytes are human subcutaneous adipocytes.

The inventors have surprisingly discovered that viable, differentiated adipocytes are a key to native-like engineered breast tissues. In some cases, without these cells present in the stroma of the tissues, the tissues do not thrive, collapse, and the resulting microarchitectures do not recapitulate native tissues. The present inventors have also recognized that existing tissue fabrication methodologies are not suitable for deposition of differentiated adipocytes because these cells are too fragile to withstand the compression and shear forces involved. The subject matter described herein provides a solution to both of these problems.

In some embodiments, the cells are bioprinted. In further embodiments, the bioprinted cells are cohered to form the engineered breast tissue. In still further embodiments, the engineered breast tissues are free or substantially free of pre-formed scaffold at the time of fabrication or the time of use. In some embodiments, the engineered breast tissues are non-innervated. In further embodiments, the engineered breast tissues lack an intact neural system and/or mature neural tissues. In some embodiments, the engineered breast tissues lack an intact vascular system and/or a mature vasculature. In further embodiments, the engineered breast tissues are free of red blood cells.

Many cell compositions and ratios are suitable for the engineered breast tissues. In some embodiments, the engineered breast tissues comprise 55%-75% fibroblasts, 15%-35% endothelial cells, and 1%-20% adipocytes. In a particular embodiment, the engineered breast tissues comprise 65% fibroblasts, 25% endothelial cells, and 10% adipocytes. In another particular embodiment, the engineered breast tissues comprise 65% fibroblasts, 25% endothelial cells, and 10% adipocytes.

Many shapes and sizes are suitable for the engineered breast tissues. By way of example, in one embodiment, the engineered breast tissues are bioprinted in form of a sheet. By way of further example, in other embodiments, the engineered breast tissues are bioprinted in form of a cube or block. By way of further example, in another embodiment, the engineered breast tissues are bioprinted in form of a sphere. Finally, in other embodiments, the engineered breast tissues are bioprinted in form of cylinder or ribbon. In some embodiments, the engineered breast tissues are about 250 µm to about 5 mm in their smallest dimension. In some embodiments, the engineered breast tissues are about 250 µm to about 5 mm in their largest dimension. In a particular embodiment, the engineered breast tissues are bioprinted in the form of cubes that are 2 or 3 mm on each side. In such embodiments, the tissues form spheres after a period of maturation in cell culture conditions.

Also described herein, in some embodiments are arrays of three-dimensional, engineered, biological breast tissues that are adapted for use in medium- or high-throughput assays such as drug screening assays, drug discovery assays, drug safety and toxicity assays, drug efficacy assays, and the like. In some embodiments, the arrays are created by depositing an engineered breast tissue into each well of a multi-well plate to form a grid of tissues.

The methods of fabricating the engineered breast tissues disclosed herein comprise bioprinting. In some embodiments, the methods include providing an adipocyte differentiation signal to adipocyte precursor cells (such as mesenchymal stem cells, preadipocytes, and the like) such that they can be deposited without substantial damage and later fully differentiate into adipocytes.

Subsequently, in some embodiments, the methods include preparing a bio-ink, the bio-ink comprising an extrusion composition (such as a hydrogel) and breast cell types such as human mammary fibroblasts, human endothelial cells, human mammary epithelial cells, and the human preadipocytes, which have been exposed to the adipocyte differentiation signal. In a particular embodiment, the bio-ink comprises, for example, 55%-75% human mammary fibroblasts, 15%-35% human endothelial cells, and 1%-20% human preadipocytes. In further embodiments, the bio-ink comprises about 50 million cells per mL to about 400 million cells per mL.

Further, in some embodiments, the methods include depositing the bio-ink onto a biocompatible surface via an automated or semi-automated deposition device such as a bioprinter. In some embodiments, one or more components of the engineered breast tissue is bioprinted. In other embodiments, each component of the engineered breast tissue is bioprinted. In a particular embodiment, the engineered breast tissues are built up, layer by layer, by bioprinting to form a three-dimensional structure.

Still further, in some embodiments, the methods include maturing the deposited bio-ink in a cell culture media to allow the cells to cohere to form the three-dimensional, engineered, biological breast tissue. In some embodiments, the cell culture media removes the hydrogel of the bio-ink leaving a substantially cellular construct. In some embodiments, the cell culture media comprises a mixture of media suited to the cell types included in the bio-ink. For example, in a particular embodiment, the cell culture media comprises human fibroblast media, human endothelial cell media, and human adipocyte differentiation media.

The engineered breast tissues described herein have many advantageous uses. For example, cancer cells are optionally introduced into the engineered breast tissues to form a breast cancer tumor model. By way of further example, an oncogenic agent is optionally applied to the engineered breast tissues to provide an initiation event in order to generate breast cancer model. By way of still further example, a diseased breast tissue is fabricated in order to generate a diseased breast cancer model. Further in this example, the diseased breast tissue is optionally exposed to a pathogen such as one or more viruses (to become viral-loaded) or one or more bacteria (to become bacteria-loaded). Such constructs are useful for research in the field of oncology and for investigation of therapies for the treatment of cancer.

Engineered Tumor Models

Described herein, in some embodiments are three-dimensional, engineered, biological tumor models comprising stromal tissue and tumor tissue. In some embodiments, the stromal tissue comprises stromal cells. In some embodiments, the tumor tissue comprises cancer cells. The engineered tumor models described herein have a compartmentalized architecture. For example, in some embodiments, the stromal tissue of the tumor model surrounds the tumor tissue. In further embodiments, the stromal tissue of the tumor model surrounds the tumor tissue on, for example, three or more, four or more, five or more, or six or more sides. In still further embodiments, the stromal tissue of the tumor model completely surrounds the tumor tissue such that the tumor tissue is embedded in the stromal tissue to form the engineered tumor model.

Many stromal cells are suitable for inclusion in the engineered tumor models. For example, in various embodiments, the engineered tumor models suitably include one or more of: fibroblasts, endothelial cells, epithelial cells, adipocytes (or preadipocytes), and immune cells such as macrophages. In further embodiments, the immune cells comprise one or more of: primary monocytes, monocyte cell lines, blood monocytes or monocyte cell lines differentiated in situ to macrophages in the tissue, monocyte cell lines derived or blood monocyte-derived macrophages differentiated in tissue culture, iPS or ES-derived macrophage type cells, and primary macrophages isolated directly from human tissue (including, but not limited to, placental, adipose, or primary tumor). In various embodiments, the cells are vertebrate cells, mammalian cells, human cells, or combinations thereof.

Many cancer cells are suitable for inclusion in the engineered tumor models. For example, in various embodiments, the engineered tumor models suitably include one or more of: cancer cell lines and primary cancer cells excised from a patient tumor. In some embodiments, the tumor tissue further comprises endothelial cells In some embodiments, the tumor tissue further comprises immune cells such as macrophages. In some embodiments, the tumor tissue further comprises fibroblasts. In some embodiments, the tumor tissue further comprises adipocytes (or preadipocytes).

In a particular non-limiting embodiment, the engineered tumor models comprise a stromal compartment with about 65% normal human mammary fibroblasts, about 25% human umbilical vein endothelial cells, and about 10% normal human pre-adipocytes and a tumor compartment with about 75% breast cancer cell line cells and about 25% human umbilical vein endothelial cells.

In some embodiments, the cells are bioprinted. In further embodiments, bioprinted stromal cells are cohered to form the engineered stromal tissue. In further embodiments, bioprinted cancer cells are cohered to form the engineered tumor tissue. In still further embodiments, the stromal tissue and the tumor tissue are cohered to form the engineered tumor model. In some embodiments, the engineered tumor models are free or substantially free of pre-formed scaffold at the time of fabrication or the time of use. In some embodiments, the engineered tumor models are non-innervated. In further embodiments, the engineered tumor models lack an intact neural system and/or mature neural tissues. In some embodiments, the engineered tumor models lack an intact vascular system and/or a mature vasculature. In further embodiments, the engineered breast tissues are free of red blood cells.

Also described herein, in some embodiments are arrays of three-dimensional, engineered, biological tumor models that are adapted for use in medium- or high-throughput assays such as drug screening assays, drug discovery assays, drug safety and toxicity assays, drug efficacy assays, and the like. In some embodiments, the arrays are created by depositing an engineered tumor model into each well of a multi-well plate to form a grid of tumor models.

In some embodiments, the tumor models are breast cancer tumor models. For example, in such embodiments, the stromal tissue comprises human mammary fibroblasts, human endothelial cells, and human adipocytes. In some embodiments, the stromal tissue further comprises human mammary epithelial cells. In some embodiments, the stromal tissue further comprises immune cells such as macrophages. In further embodiments, the immune cells comprise one or more of: primary monocytes, monocyte cell lines, blood monocytes or monocyte cell lines differentiated in situ to macrophages in the tissue, monocyte cell lines derived or blood monocyte-derived macrophages differentiated in tissue culture, iPS or ES-derived macrophage type cells, and primary macrophages isolated directly from human tissue (including, but not limited to, placental, adipose, or primary tumor). In some embodiments, the human endothelial cells are human umbilical vein endothelial cells. In some embodiments, the human endothelial cells are human mammary endothelial cells. In some embodiments, the adipocytes are subcutaneous adipocytes or adipocytes derived from adipocyte precursors such as mesenchymal stem cells and/or preadipocytes. Further, in such embodiments, the tumor tissue comprises breast cancer cells. In some embodiments, the breast cancer cells are cells of a breast cancer cell line. In other embodiments, the breast cancer cells are cells derived from an excised patient tumor. In some embodiments, the tumor tissue further comprises endothelial cells and/or immune cells such as macrophages.

Multiple tissues in the body have characteristic "glandular" or "secretory" architecture and function, where specialized epithelial cells within the tissue produce a hormone, protein, enzyme, or substance that is exerts local and/or systemic actions on other cells and tissues. Secretory tissues can be exocrine, where substances that are produced are typically carried out of the body or from one location to another through interconnected duct systems. Examples here would include production of digestive enzymes by the exocrine pancreas, sweat by the eccrine glands, and oil by the sebaceous glands. Secretory tissues can also be endocrine—the hormone-producing tissues of the body, including the endocrine pancreas, the ovaries, testes, thyroid, pituitary, and adrenal glands.

There is a common architectural "theme" in secretory tissues, in that the following attributes are present. Specialized epithelial cells are co-localized into aggregates or hollow structures with a lumen; these cells secrete regulatory or excreted substances by one or more mechanisms—the co-association of epithelial cells form 'compartments' in which the relative proportion of epithelial cells is greater than the relative proportions of other cell types. The compartments of epithelial cells are surrounded by a supporting stroma. Depending on the tissue type, the composition of the stroma can vary. Minimally, a tissue stroma typically contains some vascular cells and fibroblasts. In some tissues, the supporting stroma can also comprise smooth muscle cells, highly specialized mesenchymal cells, nerve cells, immune cells, lymph cells, and/or adipose cells. Specific cellular components of the stroma may also be compartmentalized, in that there may be distinct areas of fibrous stroma, muscular stroma, fibrovascular stroma, or adipose tissue. Epithelial cell-containing tumors often exhibit spatial organization patterns analogous with those described above; adenocarcinomas, ductal carcinomas, teratomas, and hepatoblastomas are all examples of tumor types that can possess characteristic compartmentalized patterns of stroma and epithelium. Likewise, tumors that form in compartmentalized, secretory tissues typically have compartmentalized patterns of organization wherein the stromal and epithelial patterns inherent to the normal tissue are disrupted in some manner, causing a shift in the overall tissue pattern due to a general disturbance in the overall ratio of epithelium:stroma, compared to normal tissue. Accordingly, in some embodiments, the tumor models are "glandular" or "secretory" tissue cancer tumor models.

The methods of fabricating the engineered tumor models disclosed herein comprise bioprinting. In some embodiments, the methods include preparing a stromal bio-ink comprising an extrusion compound such as a hydrogel and a plurality of stromal cell types. In further embodiments, the stromal cell types include, for example, endothelial cells, fibroblasts, epithelial cells, and/or adipocytes, preadipocytes, or a combination of adipocytes and preadipocytes. In the case of preadipocytes, the cells are pre-exposed to a differentiation signal. In some embodiments, the methods also include preparing a tumor bio-ink comprising a hydrogel and a cancer cell type. In some embodiments, the cancer cell type is a cancer cell line. In other embodiments, the cancer cells are primary cancer cells derived from an excised patient tumor, or a biopsy of a patient tumor. In some embodiments, tumor bio-ink further comprises endothelial cells and/or immune cells such as macrophages.

Subsequently, in some embodiments, the methods include depositing the stromal bio-ink and the tumor bio-ink such that the tumor bio-ink is surrounded by the stromal bio-ink and in contact with the stromal bio-ink. In further embodiments, the stromal tissue of the tumor model surrounds the tumor tissue on, for example, three or more, four or more, five or more, or six or more sides. In still further embodiments, the tumor bio-ink is completely surrounded by the stromal bio-ink and in contact with the stromal bio-ink on all sides. In some embodiments, the deposition of the bio-ink is achieved by an automated or semi-automated deposition device such as a bioprinter.

In some embodiments, the engineered tumor model is built up, layer by layer, by bioprinting to form a three-dimensional structure. In further embodiments, depositing the stromal bio-ink and the tumor bio-ink further comprises: depositing a one or more layers of stromal bio-ink on a surface to form a first sheet of stromal bio-ink; depositing one or more layers of continuous border of stromal bio-ink on the first sheet of stromal bio-ink to define a compartment, open on one side; depositing one or more layers of tumor bio-ink in the compartment to form a node of tumor bio-ink; and depositing one or more layers of stromal bio-ink to form a second sheet of stromal bio-ink to close the open side of the compartment.

Further, in some embodiments, the methods include maturing the deposited bio-ink in a cell culture media to allow the cells to cohere to form a three-dimensional, engineered, biological tumor model. In some embodiments, maturation in the cell culture media removes the hydrogel leaving a substantially cellular construct.

In some embodiments, the hydrogel is crosslinkable or reversibly crosslinkable and the methods include crosslinking the deposited bio-ink to facilitate maintenance of the tumor model architecture prior to cohesion of the cells. In further embodiments, the methods include removing the crosslinked hydrogel by enzymatic degradation subsequent to cell cohesion. The present inventors have discovered that the tumor model architectures described herein are best achieved using such a crosslinkable extrusion compound (e.g., hydrogel), without which the compartmentalized architecture is often lost prior to fusion of the tumor model.

The engineered tumor models, including breast cancer tumor models, described herein have many advantageous uses. For example, primary cancer cells excised from a tumor of a patient could be utilized to form the tumor tissue in order to create an in vitro tumor model customized to investigate that patient's disease. Such a personalized tumor model is optionally used to evaluate potential therapies and identify therapies, such as chemotherapeutic compounds and biologics, which are effective in treating the patient's disease. Such constructs are useful for research in the field of oncology and for investigation of therapies for the treatment of cancer.

Mammary tumor models were fabricated directly into multi-well plates and used to establish biological response profiles to signal mediators including estradiol, progestin, prolactin, and HGF as well as the standard chemotherapeutic agents cisplatin, paclitaxel, methotrexate, and tamoxifen. The effects of chemotherapeutic drugs on specific cell types within the neotissues was assessed by staining with cell-type specific markers in addition to fluorescent live/dead and cytotoxicity assays. The response of the three-dimensional breast cancer tumor models to growth factors, hormones, and chemotherapeutic agents was compared to the response of two-dimensional breast cancer cell lines. The models described herein are superior to existing models used to screen new anti-cancer targets with better efficiency and accuracy for targeting of cancer cells in the context of the in vivo microenvironment.

Advantages of the engineered tumor models described herein include, but are not limited to:

The tumor models retain compartmentalized structures with interaction between stromal and cancer cells.

Following bioprinting of the stromal compartment, formation of endothelial networks and differentiation of adipocytes are observed.

Uniform, tumor-like structures are generated and ready for treatment with compounds, such as chemotherapeutic agents, at Day 6 post-printing (see, e.g., Examples 3, 9, and 10).

The tumor models demonstrate native-like drug penetration and response to chemotherapeutic compounds. Isolated two-dimensional cancer cells were more susceptible to tamoxifen-induced toxicity than cells incorporated into three-dimensional bioprinted constructs when treated with the same dose of tamoxifen for the same duration.

Assays

In some embodiments, the engineered tissues, including breast tissues, and tumor models, including breast cancer tumor models, described herein are for use in in vitro assays. In some embodiments, an "assay" is a procedure for testing or measuring the presence or activity of a substance (e.g., a chemical, molecule, biochemical, drug, etc.) in an organic or biologic sample (e.g., cell aggregate, tissue, organ, organism, etc.). In further embodiments, assays include qualitative assays and quantitative assays. In still further embodiments, a quantitative assay measures the amount of a substance in a sample.

In various embodiments, the engineered tissues, including breast tissues, and tumor models, including breast cancer tumor models, described herein are for use in, by way of non-limiting examples, image-based assays, measurement of secreted proteins, expression of markers, and production of proteins. In various further embodiments, the engineered tissues, including breast tissues, and tumor models, including breast cancer tumor models, described herein are for use in assays to detect or measure one or more of: molecular binding (including radioligand binding), molecular uptake, activity (e.g., enzymatic activity and receptor activity, etc.), gene expression, protein expression, receptor agonism, receptor antagonism, cell signaling, apoptosis, chemosensitivity, transfection, cell migration, chemotaxis, cell viability, cell proliferation, safety, efficacy, metabolism, toxicity, and abuse liability.

In some embodiments, the engineered tissues, including breast tissues, and tumor models, including breast cancer tumor models, described herein are for use in immunoassays. In further embodiments, immunoassays are competitive immunoassays or noncompetitive immunoassays. In a competitive immunoassay, for example, the antigen in a sample competes with labeled antigen to bind with antibodies and the amount of labeled antigen bound to the antibody site is then measured. In a noncompetitive immunoassay (also referred to as a "sandwich assay"), for example, antigen in a sample is bound to an antibody site; subsequently, labeled antibody is bound to the antigen and the amount of labeled antibody on the site is then measured.

In some embodiments, the engineered tissues, including breast tissues, and tumor models, including breast cancer tumor models, described herein are for use in enzyme-linked immunosorbent assays (ELISA). In further embodiments, an ELISA is a biochemical technique used to detect the presence of an antibody or an antigen in a sample. In ELISA, for example, at least one antibody with specificity for a particular antigen is utilized. By way of further example, a sample with an unknown amount of antigen is immobilized on a solid support (e.g., a polystyrene microtiter plate) either non-specifically (via adsorption to the surface) or specifically (via capture by another antibody specific to the same antigen, in a "sandwich" ELISA). By way of still further example, after the antigen is immobilized, the detection antibody is added, forming a complex with the antigen. The detection antibody is, for example, covalently linked to an enzyme, or is itself detected by a secondary antibody that is linked to an enzyme through bioconjugation.

For example, in some embodiments, an array, microarray, or chip of cells, multicellular aggregates, or tissues is used for drug screening or drug discovery. In further embodiments, an array, microarray, or chip of tissues is used as part of a kit for drug screening or drug discovery. In some embodiments, each vascular wall segment exists within a well of a biocompatible multi-well container, wherein the container is compatible with one or more automated drug screening procedures and/or devices. In further embodiments, automated drug screening procedures and/or devices include any suitable procedure or device that is computer or robot-assisted.

In some embodiments, arrays for drug screening assays or drug discovery assays are used to research or develop drugs potentially useful in any therapeutic area. In still further embodiments, suitable therapeutic areas include, by way of non-limiting examples, infectious disease, hematology, oncology, pediatrics, cardiology, central nervous system disease, neurology, gastroenterology, hepatology, urology, infertility, ophthalmology, nephrology, orthopedics, pain control, psychiatry, pulmonology, vaccines, wound healing, physiology, pharmacology, dermatology, gene therapy, toxicology, and immunology.

In some embodiments, arrays for therapy screening assays or therapy discovery assays are used to identify therapies potentially useful in the disease or condition of a particular individual or group of individuals. For example, in some embodiments, the methods described herein include utilizing cells of a particular individual to engineer tissues, disease models, or tumor models. In further embodiments, the methods include applying a candidate therapeutic agent to the tissue or model; measuring viability of the cells; and selecting a therapeutic agent for the individual based on the measured viability of the cells. In still further embodiments, the candidate therapeutic agent is a one or more chemotherapeutic compounds, one or more radiopharmaceutical compounds, radiation therapy, or a combination thereof. Accordingly, disclosed herein are methods of personalizing medicine to an individual or group of individuals.

Engineered Adipocyte-Containing Tissues

As described herein, previous tissue fabrication technologies have failed to adequately provide engineered tissues containing sufficiently viable, differentiated adipocytes due primarily to the fragility of adipocytes and their susceptibility to damage. Described herein, in some embodiments are three-dimensional, engineered, biological tumor models comprising viable, differentiated adipocytes. Viable adipocytes are an important factor in formation of native-like microarchitecture in some tissues.

In some embodiments, the tissue is an adipose rich or adipose-dependent tissue. In further embodiments, the tissue is adipose tissue. In some embodiments, the tissue comprises, for example, at least about 5%, 10%, 15%, 20%, 25%, 30%, 35%, 40%, 45%, 50%, 55%, 60%, 65%, 70%, 75%, 80%, 85% or more viable, differentiated adipocytes. In a particular, non-limiting embodiment, the tissue comprises at least about 5% or at least about 10% viable, differentiated adipocytes.

In some embodiments, for example, at least about 5%, 10%, 15%, 20%, 25%, 30%, 35%, 40%, 45%, 50%, 55%, 60%, 65%, 70%, 75%, 80%, 85% or more of the adipocytes are viable post-fabrication. In a particular, non-limiting embodiment, at least about 50% or at least about 75% of the adipocytes are viable post-fabrication. In various embodiments, the adipocyte viability extends to about 1, 2, 3, 4, 5, 6, 7, 8 or more days post-fabrication. In further embodiments, the adipocytes secrete detectable amounts of leptin post-fabrication. In various embodiments, the leptin secretion extends to about 1, 2, 3, 4, 5, 6, 7, 8 or more days post-fabrication.

In some embodiments, the adipocytes are bioprinted. In further embodiments, bioprinted adipocytes are cohered to form the engineered tissue. In some embodiments, the engineered adipocyte-containing tissues are free or substantially free of pre-formed scaffold at the time of fabrication or the time of use. In some embodiments, the engineered adipocyte-containing tissues are non-innervated.

In some embodiments, the adipocytes are subcutaneous adipocytes. In some embodiments, the adipocytes are derived from adipocyte precursor cells such as mesenchymal stem cells (including bone marrow derived mesenchymal stem cells) or preadipocytes.

The methods described herein allow for bioprinting of tissues containing viable, differentiated adipocytes, which are key stromal components in many tissues and tumor models.

The methods of fabricating the engineered adipose tissues disclosed herein comprise bioprinting. In some embodiments, the methods include providing an adipocyte differentiation signal to adipocyte precursors such as stem cells or preadipocytes. In further embodiments, adipocyte precursors such as stem cells or preadipocytes are at least partially pre-differentiated at the time of bioprinting.

Subsequently, in some embodiments, the methods include preparing a bio-ink comprising an extrusion compound such as a hydrogel, the preadipocytes, and at least one other cell type such as endothelial cells.

Further, in some embodiments, the methods include depositing the bio-ink on a surface via an automated or semi-automated deposition device such as a bioprinter. In a particular embodiment, the engineered tissues are built up, layer by layer, by bioprinting to form a three-dimensional structure.

Further, in some embodiments, the methods include maturing the bio-ink in a cell culture media to allow the cells to cohere to form a three-dimensional, engineered, biological construct, the construct comprising viable, differentiated adipocytes. In further embodiments, the maturation in the cell culture media also removes the hydrogel leaving a substantially cellular construct.

Figure 23:
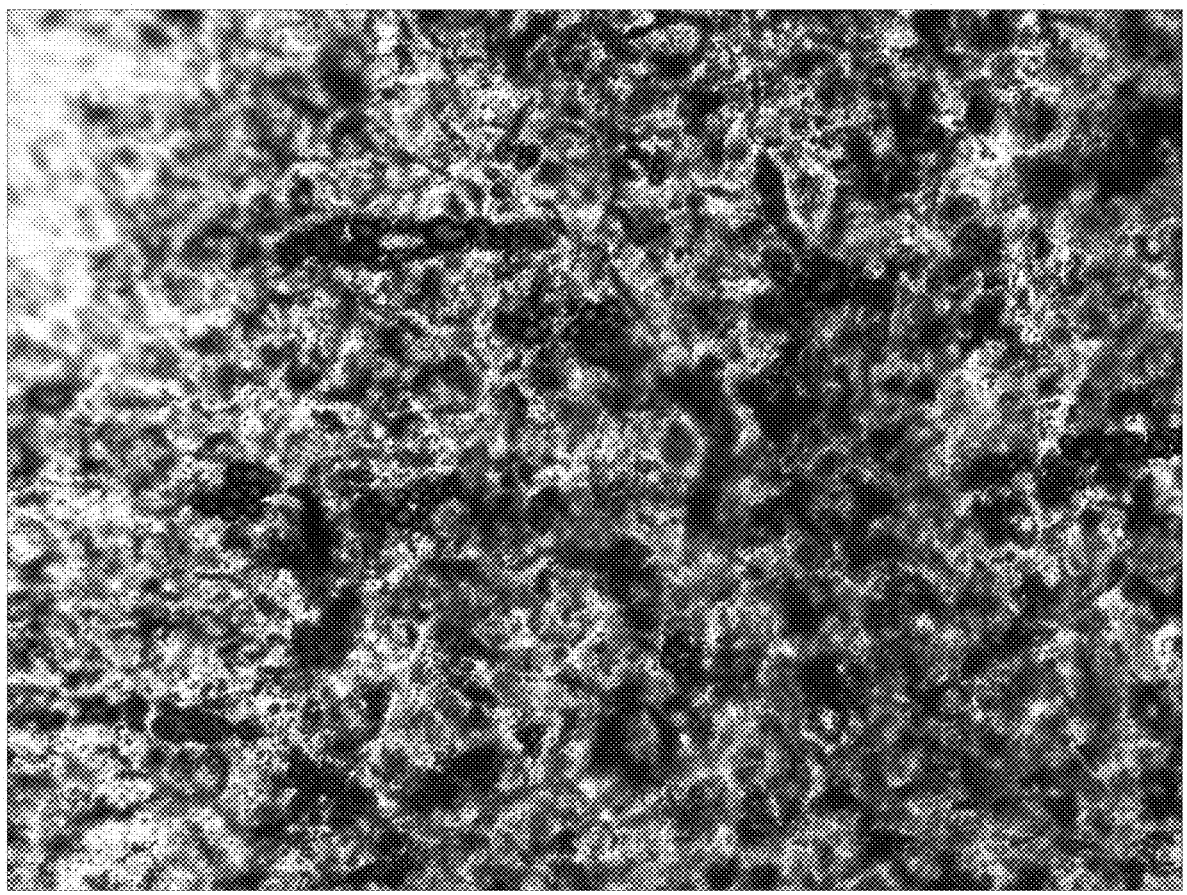
FIG. 23 shows a non-limiting exemplary photomicrograph of bioprinted adipose tissue, in this case, a photomicrograph depicting Oil Red O staining for lipids.

Referring to FIG. 23, adipose tissue was bioprinted via the methods described herein. In this embodiment the adipocytes were differentiated, viable, and produced characteristic lipid deposits as revealed by staining with Oil Red O.

Additional Non-Limiting Embodiments

Further disclosed herein are three-dimensional, engineered, biological tumor models comprising: stromal tissue; and tumor tissue; the tumor tissue comprising cancer cells, the tumor tissue surrounded on all sides by the stromal tissue to form the three-dimensional, engineered, biological tumor model; provided that the stromal tissue was bioprinted from a stromal bio-ink, the tumor tissue was bioprinted from a tumor bio-ink, or both the stromal tissue and the tumor tissue were bioprinted from their respective bio-inks. In some embodiments, the model is substantially free of pre-formed scaffold. In some embodiments, the stromal tissue comprises: endothelial cells, fibroblasts, and adipocytes, preadipocytes, or both adipocytes and preadipocytes. In further embodiments, the stromal tissue comprises 55%-75% fibroblasts, 15%-35% endothelial cells, and 1%-20% adipocytes. In some embodiments, the tumor tissue comprises cells of a cancer cell line. In other embodiments, the tumor tissue comprises primary cancer cells from a patient tumor. In some embodiments, the tumor tissue comprises endothelial cells. In further embodiments, the tumor tissue comprises 65-85% cancer cells and 15%-35% endothelial cells. In some embodiments, the tumor model is about 250 μm to about 5 mm in its smallest dimension. In some embodiments, the stromal tissue is human breast stroma and the tumor tissue is human breast tumor. In some embodiments, the tumor tissue is completely surrounded on all sides by the stromal tissue to form the three-dimensional, engineered, biological tumor model.

Further disclosed herein are methods of fabricating a three-dimensional, engineered, biological tumor model, the method comprising: preparing a stromal bio-ink, the stromal bio-ink comprising an extrusion compound and a plurality of stromal cell types; preparing a tumor bio-ink, the tumor bio-ink comprising an extrusion compound and a cancer cell type; depositing the stromal bio-ink and the tumor bio-ink such that the tumor bio-ink is embedded in the stromal bio-ink and in contact with the stromal bio-ink on all sides; and maturing the deposited bio-ink in a cell culture media to remove the extrusion compound and allow the cells to cohere to form a three-dimensional, engineered, biological tumor model. In some embodiments, the bio-ink is deposited by bioprinting. In some embodiments, the extrusion compound comprises alginate. In some embodiments, the extrusion compound is removable by enzymatic digestion. In further embodiments, the method further comprises cross-linking the deposited bio-ink to physically stabilize the tumor model architecture prior to cohesion of the cells. In still further embodiments, the method further comprises removing the crosslinked bio-ink by enzymatic degradation subsequent to cell cohesion. In some embodiments, the stromal cell types comprise endothelial cells, fibroblasts and adipocytes or preadipocytes. In further embodiments, the stromal bio-ink comprises 55%-75% fibroblasts, 15%-35% endothelial cells, and 1%-20% adipocytes. In some embodiments, the cancer cell type comprises a cancer cell line. In other embodiments, the cancer cell type comprises primary cancer cells from a patient tumor. In some embodiments, the tumor bio-ink further comprises endothelial cells. In some embodiments, the stromal bio-ink comprises about 50 million cells per mL to about 300 million cells per mL. In some embodiments, the tumor bio-ink comprises about 50 million cells per mL to about 300 million cells per mL. In some embodiments, the cell culture media comprises soluble components that support the grown, maintenance, or differentiation of human fibroblasts, human endothelial cells, adipocytes, and cancer cells. In some embodiments, depositing the stromal bio-ink and the tumor bio-ink further comprises: depositing a first sheet of stromal bio-ink on a surface; depositing a continuous border of stromal bio-ink on the first sheet of stromal bio-ink to define a compartment, the compartment open on one side; depositing a node of tumor bio-ink in the compartment; and depositing a second sheet of stromal bio-ink to close the open side of the compartment. In some embodiments, the tumor model is a breast cancer model.

Further disclosed herein are three-dimensional, engineered, biological breast cancer models comprising: breast stromal tissue, the stromal tissue comprising human mammary fibroblasts, human endothelial cells, and human adipocytes; and breast cancer tumor tissue; the tumor tissue comprising breast cancer cells and human endothelial cells, the tumor tissue surrounded on all sides by the stromal tissue to form the three-dimensional, engineered, biological breast cancer model; provided that the stromal tissue was bioprinted from a stromal bio-ink, the tumor tissue was bioprinted from a tumor bio-ink, or both the stromal tissue and the tumor tissue were bioprinted from their respective bio-inks. In some embodiments, the model is substantially free of pre-formed scaffold. In some embodiments, the breast stromal tissue comprises 55%-75% fibroblasts, 15%-35% endothelial cells, and 1%-20% adipocytes. In some embodiments, the breast cancer cells are derived from a breast cancer cell line. In other embodiments, the breast cancer cells are primary cancer cells from a patient tumor. In some embodiments, the breast cancer tumor tissue comprises 65-85% cancer cells and 15%-35% endothelial cells. In some embodiments, the breast cancer model is 250 µm to 5 mm in its smallest dimension. In some embodiments, the breast cancer tumor tissue is completely surrounded on all sides by the breast stromal tissue to form the three-dimensional, engineered, biological breast cancer model.

Further disclosed herein are methods of fabricating a three-dimensional, engineered, biological breast cancer model, the method comprising: preparing a stromal bio-ink, the stromal bio-ink comprising a plurality of stromal cell types, the stromal cell types comprising: an extrusion compound, human mammary fibroblasts, human endothelial cells, and human adipocytes; preparing a tumor bio-ink, the tumor bio-ink comprising: an extrusion compound, a breast cancer cell type and human endothelial cells; depositing the stromal bio-ink and the tumor bio-ink such that the tumor bio-ink is embedded in the stromal bio-ink and in contact with the stromal bio-ink on all sides; and maturing the deposited bio-ink in a cell culture media to remove the extrusion compound allow the cells to cohere to form a three-dimensional, engineered, biological breast cancer model. In some embodiments, the bio-ink is deposited by bioprinting. In some embodiments, the extrusion compound comprises alginate. In some embodiments, the extrusion compound is removable by enzymatic digestion. In further embodiments, the method further comprises crosslinking the deposited bio-ink to facilitate maintenance of the breast cancer model architecture prior to cohesion of the cells. In still further embodiments, the method further comprises removing the crosslinked bio-ink by enzymatic degradation subsequent to cell cohesion. In some embodiments, the stromal bio-ink comprises 55%-75% human mammary fibroblasts, 15%-35% human endothelial cells, and 1%-20% human adipocytes. In some embodiments, the breast cancer cell type comprises a breast cancer cell line. In other embodiments, the cancer cell type comprises primary breast cancer cells from a patient tumor. In some embodiments, the stromal bio-ink comprises about 50 million cells per mL to about 300 million cells per mL. In some embodiments, the tumor bio-ink comprises about 50 million cells per mL to about 300 million cells per mL. In some embodiments, the cell culture media comprises soluble components that support the grown, maintenance, or differentiation of human fibroblasts, human endothelial cells, adipocytes, and cancer cells. In some embodiments, depositing the stromal bio-ink and the tumor bio-ink further comprises: depositing a first sheet of stromal bio-ink on a surface; depositing a continuous border of stromal bio-ink on the first sheet of stromal bio-ink to define a compartment, the compartment open on one side; depositing a node of tumor bio-ink in the compartment; and depositing a second sheet of stromal bio-ink to close the open side of the compartment. In some embodiments, the adipocytes are preadipocytes and the method further comprises providing an adipocyte differentiation signal to the preadipocytes.

Further disclosed herein are methods of identifying a therapeutic agent for cancer in an individual, the method comprising: preparing a stromal bio-ink, the stromal bio-ink comprising a plurality of stromal cell types; preparing a tumor bio-ink, the tumor bio-ink comprising primary cancer cells from the individual; depositing the stromal bio-ink and the tumor bio-ink such that the tumor bio-ink is embedded in the stromal bio-ink and in contact with the stromal bio-ink on all sides; maturing the deposited bio-ink in a cell culture media to allow the cells to cohere to form a three-dimensional, engineered, biological construct; applying a candidate therapeutic agent to the construct; measuring viability of the cancer cells; and selecting a therapeutic agent for the individual based on the measured viability of the cancer cells; provided that at least one component of the construct was deposited by bioprinting. In some embodiments, the stromal bio-ink and the tumor bio-ink are deposited by bioprinting. In some embodiments, the bio-ink further comprises an extrusion compound. In further embodiments, the extrusion compound is removable by enzymatic digestion. In still further embodiments, the method further comprises crosslinking the deposited bio-ink to physically stabilize the tumor model architecture prior to cohesion of the cells. In yet further embodiments, the method further comprises removing the crosslinked bio-ink by enzymatic degradation subsequent to cell cohesion. In some embodiments, the stromal cell types comprise endothelial cells, fibroblasts and adipocytes or preadipocytes. In further embodiments, the stromal bio-ink comprises 55%-75% fibroblasts, 15%-35% endothelial cells, and 1%-20% adipocytes. In some embodiments, the tumor bio-ink further comprises endothelial cells. In some embodiments, the stromal bio-ink comprises about 50 million cells per mL to about 300 million cells per mL. In some embodiments, the tumor bio-ink comprises about 50 million cells per mL to about 300 million cells per mL. In some embodiments, the cell culture media comprises soluble components that support the growth, maintenance, or differentiation of human fibroblasts, human endothelial cells, adipocytes, and cancer cells. In some embodiments, depositing the stromal bio-ink and the tumor bio-ink further comprises: depositing a first sheet of stromal bio-ink on a surface; depositing a continuous border of stromal bio-ink on the first sheet of stromal bio-ink to define a compartment, the compartment open on one side; depositing a node of tumor bio-ink in the compartment; and depositing a second sheet of stromal bio-ink to close the open side of the compartment. In some embodiments, the three-dimensional, engineered, biological construct is a breast cancer construct.

Further disclosed herein are three-dimensional, engineered, biological tissues comprising viable, differentiated adipocytes. In some embodiments, the tissue was bioprinted. In some embodiments, the tissue is substantially free of pre-formed scaffold. In some embodiments, the tissue comprises at least 5% viable, differentiated adipocytes. In further embodiments, the tissue comprises at least 10% viable, differentiated adipocytes. In some embodiments, at least 50% of the adipocytes are viable 24 hours post-fabrication. In further embodiments, at least 75% of the adipocytes are viable 24 hours post-fabrication. In some embodiments, the adipocytes secrete leptin for at least 1 week post-fabrication. In some embodiments, the tissue is adipose tissue. In some embodiments, the adipocytes are subcutaneous adipocytes. In other embodiments, the adipocytes are derived from preadipocytes or mesenchymal stem cells.

Further disclosed herein are methods of fabricating a three-dimensional, engineered, adipose tissue-containing, biological construct, the method comprising: providing an adipocyte differentiation signal to preadipocytes; preparing a preadipocyte bio-ink, the bio-ink comprising the preadipocytes and at least one other cell type; depositing the bio-ink on a surface; and maturing the bio-ink in a cell culture media to allow the cells to cohere to form a three-dimensional, engineered, biological construct, the construct comprising viable, differentiated adipocytes. In some embodiments, the bio-ink is deposited by bioprinting. In some embodiments, the construct comprises at least 5% viable, differentiated adipocytes. In further embodiments, the construct comprises at least 10% viable, differentiated adipocytes. In some embodiments, at least 50% of the adipocytes are viable 24 hours post-fabrication. In further embodiments, at least 75% of the adipocytes are viable 24 hours post-fabrication. In some embodiments, the adipocytes secrete leptin for at least 1, 2, 3, 4, 5, 6, or 7 days post-fabrication. In some embodiments, the adipocytes secrete leptin for at least 1, 2, or 3 weeks post-fabrication. In some embodiments, the construct is adipose tissue. In some embodiments, the preadipocytes are subcutaneous preadipocytes.

Further disclosed herein are three-dimensional, engineered, biological breast tissues comprising: human mammary fibroblasts, human endothelial cells, human mammary epithelial cells, and human adipocytes; provided that the cells were bioprinted from a bio-ink and cohered to form the three-dimensional, engineered, biological breast tissue; provided that the tissue is substantially free of pre-formed scaffold. In some embodiments, the tissue comprises 55%-75% fibroblasts, 15%-35% endothelial cells, and 1%-20% adipocytes. In some embodiments, the tissue is about 250 μm to about 5 mm in its smallest dimension. In some embodiments, the tissue is exposed to a disease-causing agent to create a breast tissue disease model. In further embodiments, the disease-causing agent comprises a virus, a bacterium, a chemical compound, or a combination thereof.

Further disclosed herein are methods of fabricating a three-dimensional, engineered, biological breast tissue, the method comprising: providing an adipocyte differentiation signal to human preadipocytes; preparing a bio-ink, the bio-ink comprising a plurality of breast cell types, the breast cell types comprising human mammary fibroblasts, human endothelial cells, human mammary epithelial cells, and the human preadipocytes; depositing the bio-ink on a biocompatible surface; and maturing the deposited bio-ink in a cell culture media to allow the cells to cohere to form a three-dimensional, engineered, biological breast tissue. In some embodiments, the bio-ink is deposited by bioprinting. In some embodiments, the bio-ink comprises 55%-75% human mammary fibroblasts, 15%-35% human endothelial cells, and 1%-20% human preadipocytes. In some embodiments, the bio-ink comprises about 50 million cells per mL to about 300 million cells per mL. In some embodiments, the cell culture media comprises soluble components that support the growth, maintenance, or differentiation of human fibroblasts, human endothelial cells, and adipocytes. In some embodiments, the method further comprises exposing the three-dimensional, engineered, biological breast tissue to a disease-causing agent to create a breast tissue disease model. In further embodiments, the disease-causing agent comprises a virus, a bacterium, a chemical compound, or a combination thereof.

Further disclosed herein are arrays of three-dimensional, engineered, biological tumor models, each tumor model comprising: stromal tissue and tumor tissue; the tumor tissue comprising cancer cells, the tumor tissue surrounded on all sides by the stromal tissue to form each three-dimensional, engineered, biological tumor model; provided that the stromal tissue, the tumor tissue, or both the stromal tissue and the tumor tissue were bioprinted; provided that the array is adapted for use in a high throughput assay. In some embodiments, each tumor model is substantially free of pre-formed scaffold. In some embodiments, each tumor model is in a well of a multi-well plate. In some embodiments, the stromal tissue comprises: endothelial cells, fibroblasts, and adipocytes, preadipocytes, or both adipocytes and preadipocytes. In some embodiments, the stromal tissue comprises 55%-75% fibroblasts, 15%-35% endothelial cells, and 1%-20% adipocytes. In some embodiments, the tumor tissue comprises primary cancer cells from a patient tumor. In some embodiments, the tumor tissue comprises endothelial cells. In further embodiments, the tumor tissue comprises 65%-85% cancer cells and 15%-35% endothelial cells. In some embodiments, each tumor model is about 250 μm to about 5 mm in its smallest dimension. In some embodiments, the stromal tissue is human breast stroma and the tumor tissue is human breast tumor. In some embodiments, the tumor tissue is completely surrounded on all sides by the stromal tissue to form each three-dimensional, engineered, biological tumor model.

Further disclosed herein are arrays of three-dimensional, engineered, biological breast cancer models, each breast cancer model comprising: stromal tissue, the stromal tissue comprising human mammary fibroblasts, human endothelial cells, and human adipocytes; and tumor tissue; the tumor tissue comprising breast cancer cells and human endothelial cells, the tumor tissue surrounded on all sides by the stromal tissue to form each three-dimensional, engineered, biological breast cancer model; provided that the stromal tissue, the tumor tissue, or both the stromal tissue and the tumor tissue were bioprinted; provided that the array is adapted for use in a high throughput assay. In some embodiments, each breast cancer model is substantially free of pre-formed scaffold. In some embodiments, each breast cancer model is in a well of a multi-well plate. In some embodiments, the stromal tissue comprises 55%-75% fibroblasts, 15%-35% endothelial cells, and 1%-20% adipocytes. In some embodiments, the breast cancer cells are primary cancer cells from a patient tumor. In some embodiments, the tumor tissue comprises 65-85% cancer cells and 15%-35% endothelial cells. In some embodiments, each breast cancer model is about 250 μm to about 5 mm in its smallest dimension. In some embodiments, the tumor tissue is completely surrounded on all sides by the stromal tissue to form each three-dimensional, engineered, biological breast cancer model.

Further disclosed herein are three-dimensional, engineered, biological tumor tissues comprising human cancer cells; provided that the cells are cohered to form the three-dimensional, engineered, biological tumor tissue; provided that the tumor tissue is substantially free of pre-formed scaffold. In some embodiments, the tumor tissue was bioprinted from a cancer cell bio-ink. In some embodiments, the tumor tissue further comprises one or more of fibroblasts, endothelial cells, epithelial cells, adipocytes, and immune cells. In some embodiments, the tumor tissue is about 250 μm to about 5 mm in its smallest dimension. In some embodiments, the tumor tissue was exposed to a carcinogen to transform the cells. In further embodiments, the disease-causing agent comprises a virus, a bacterium, a chemical compound, or a combination thereof. In some embodiments, a crosslinkable extrusion compound is used to physically stabilize the tumor tissue subsequent to fabrication and prior to cohesion of the cells to form the tumor tissue.

EXAMPLES

The following illustrative examples are representative of embodiments of the software applications, systems, and methods described herein and are not meant to be limiting in any way.

Example 1—Engineered Human Breast Tissue Model

Fabrication

A 6-layer cube with dimensions 3 mm×3 mm×3 mm was bioprinted onto a Transwell membrane in a 6-well tissue culture plate according to the schematic diagram shown in FIG. 1 (Structure 1). The bottom two and top two layers were composed of 75% normal human mammary fibroblasts (NHMF) and 25% human umbilical vein endothelial cells (HUVEC). The middle two layers were comprised of a bioprinted square of 75% NHMF/25% HUVEC surrounding a core of human mammary epithelial cells (HMEC) resuspended in an alginate and gelatin-containing hydrogel (Novogel® 2.0 System; Organovo, Calif.) to produce a bio-ink comprising 50-300 million cells/mL. Immediately following bioprinting, structures were incubated with 50 mM $CaCl_2$ for 2 minutes, and cultured for 6 days. On day 6 of culture, the constructs were incubated with alginate lyase to degrade the hydrogel and incubated for a further 24 hours.

Results

Figure 2:
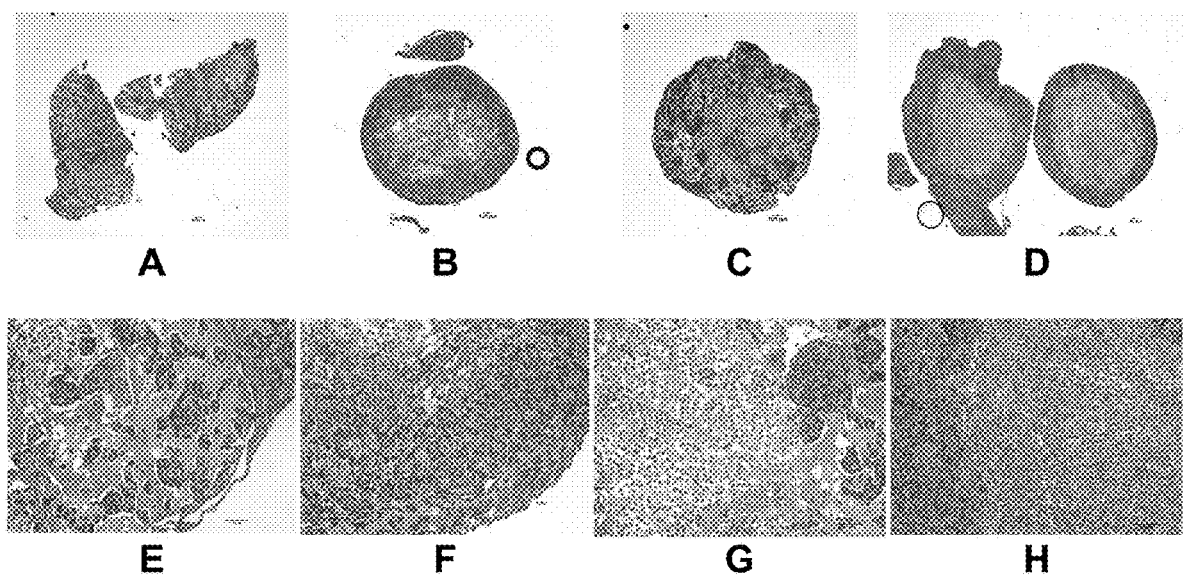
FIG. 2 shows a non-limiting series of representative photomicrographs of the construct of FIG. 1; in this case, photomicrographs depicting Hematoxylin & Eosin (H&E) stained specimens shown at 2× (A-D) and 20× (E-H) magnification. Samples from left to right: the first column (A and E) includes hydrogel, the second column (B and F) includes hydrogel and was treated with lyase, the third column (C and G) includes ECM, and the last column (D and H) includes ECM and was treated with lyase.

Assessment of Structure 1 was performed by histological staining for cell-type specific markers. A representative H&E stain for Structure 1 is shown in FIG. 2. Referring to FIG. 2, the H&E stained specimens were prepared at day 7 post-fabrication; the top row (A-D) shows 2× magnification and the bottom row (E-H) shows 20× magnification; from left to right the first column (A and E) includes hydrogel, the second column (B and F) includes hydrogel and was treated with lyase, the third column (C and G) includes ECM, and the last column (D and H) includes ECM and was treated with lyase.

Figure 3A:
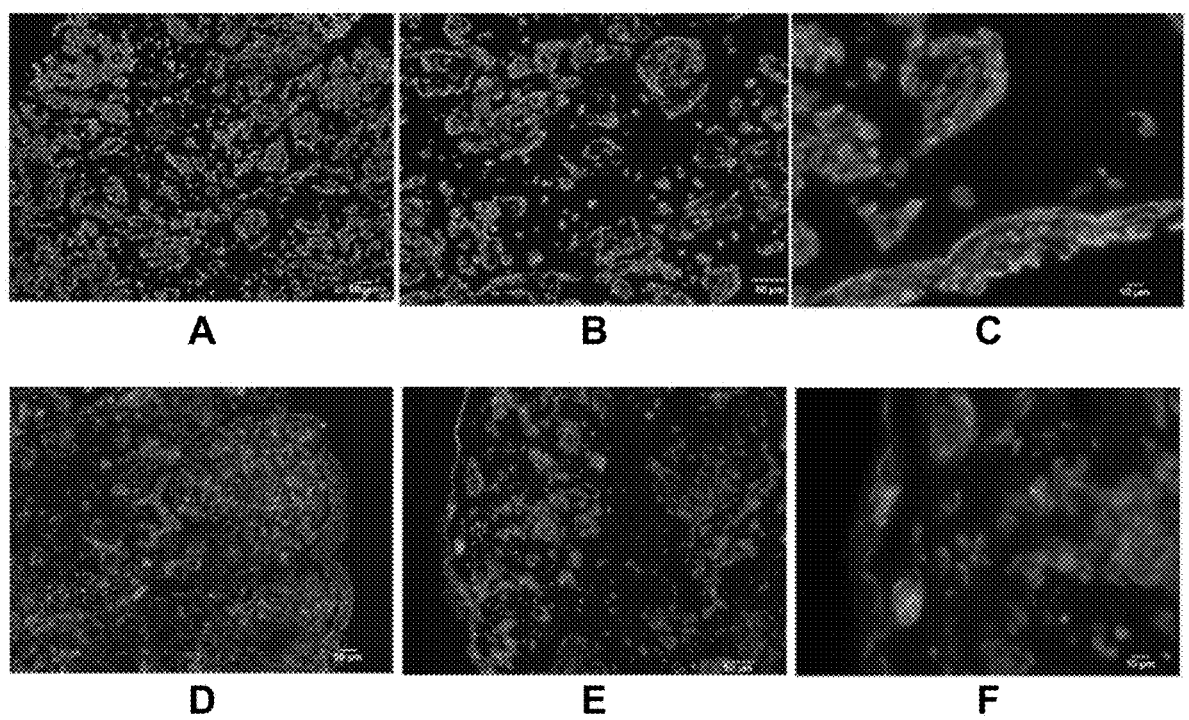
FIGS. 3A-3D show non-limiting series of representative photomicrographs of the construct of FIG. 1 (day 7 post-fabrication); in this case, photomicrographs depicting constructs stained to visualize human mammary fibroblasts by antibodies against vimentin (green) and TE7. The constructs of FIG. 3A include ECM, the constructs of FIG. 3B include hydrogel, the constructs of FIG. 3C include ECM and were treated with lyase, and the constructs of FIG. 3D include hydrogel and were treated with lyase. For each of FIGS. 3A-3D, the top row (A-C) shows vimentin (green) and the bottom row (D-F) shows TE7 (green); the first column (A and D) shows 10× magnification, the second column (B and E) shows 20× magnification, and the last column (C and F) shows 60× magnification.
Figure 3B:
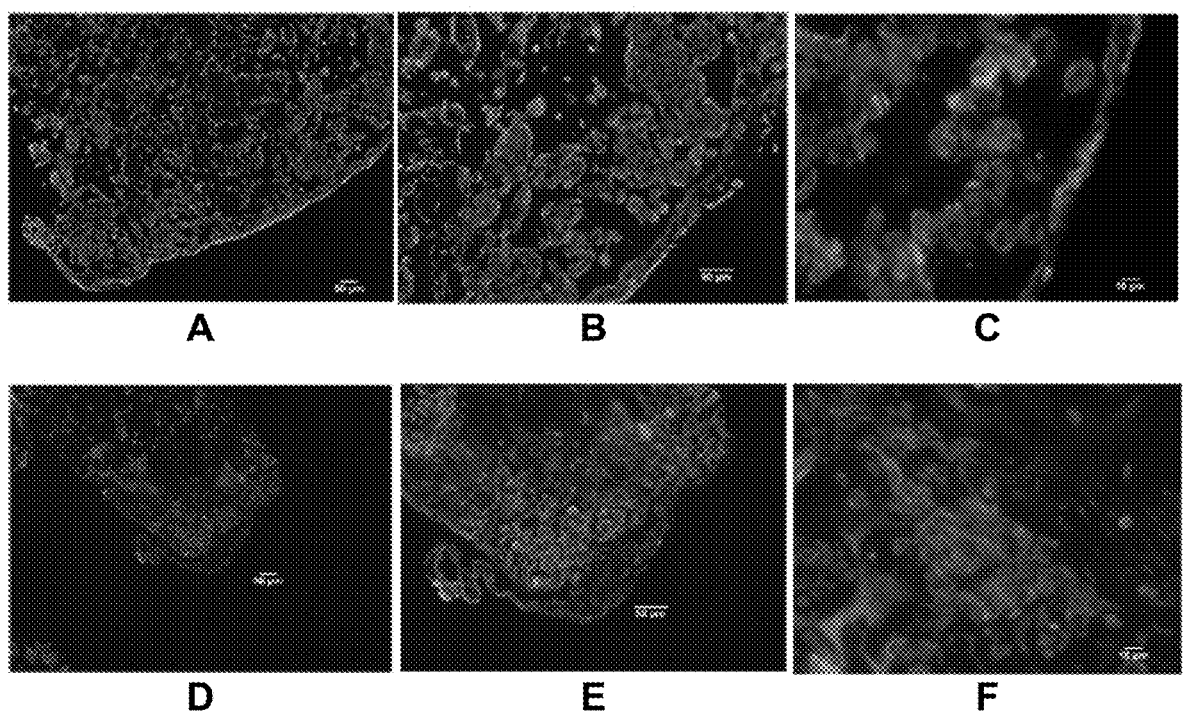
Figure 3C:
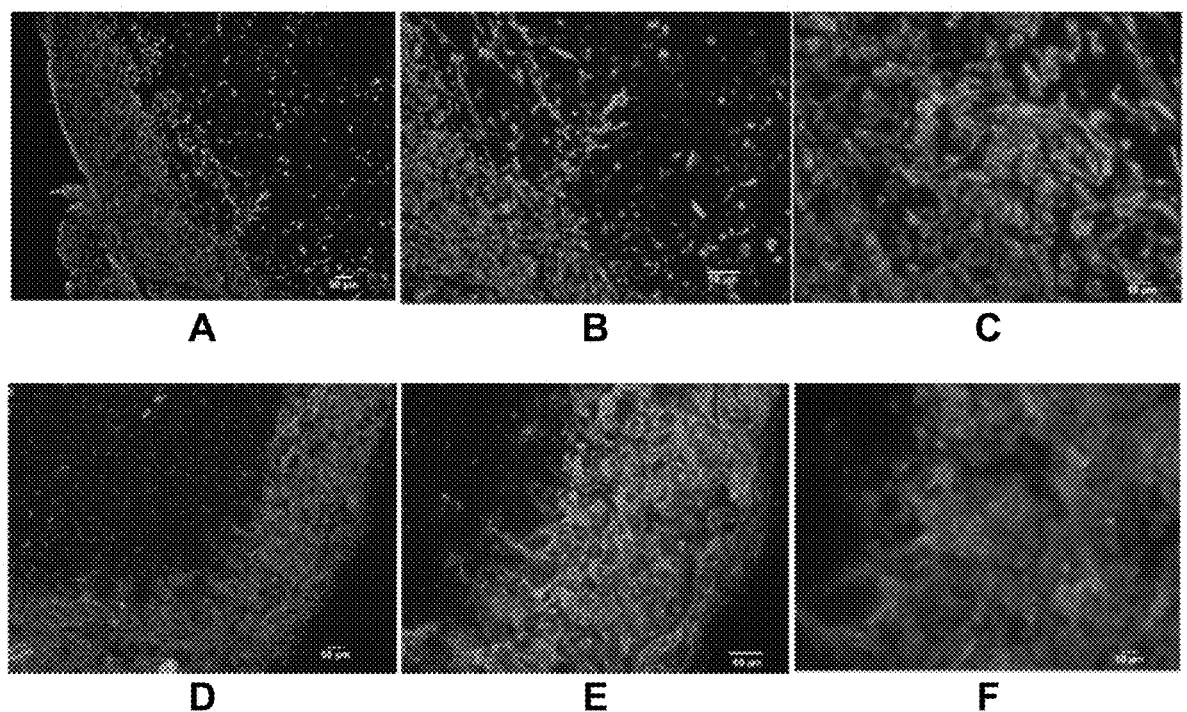
Figure 3D:
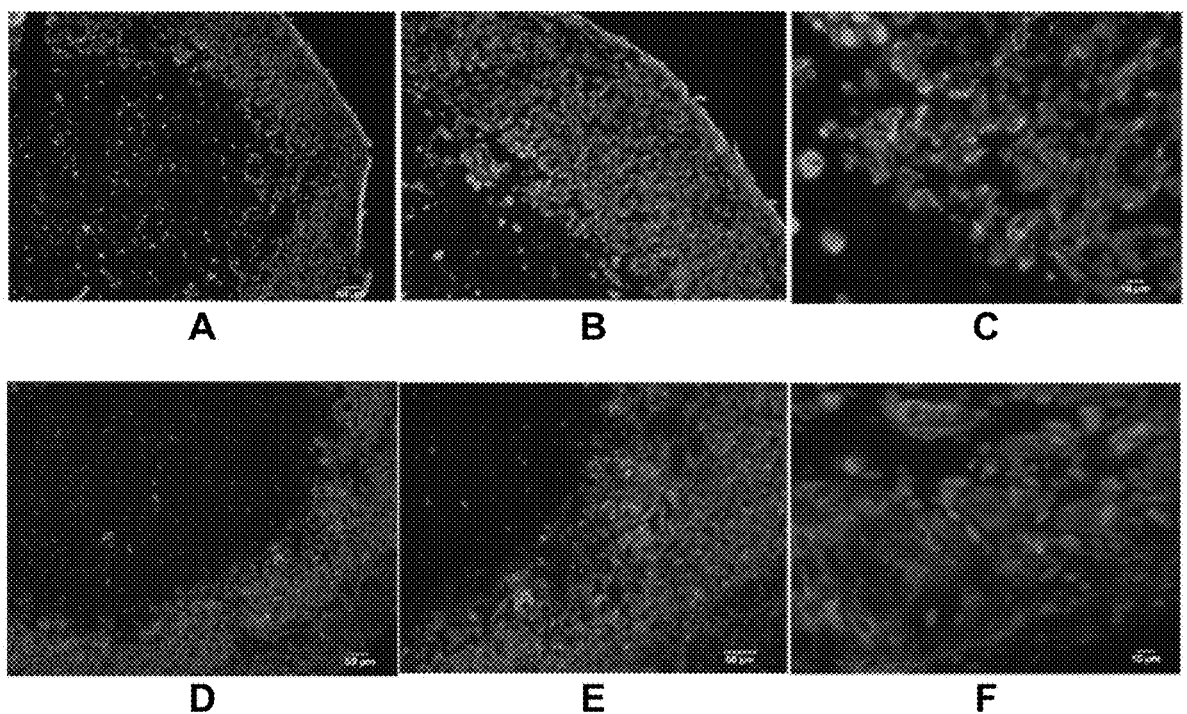

Constructs were stained for vimentin and TE7 (day 7 post-fabrication), markers of human mammary fibroblasts, which localized to the outer part of the construct and were excluded from the interior, where HMEC cells were bioprinted. See FIGS. 3A-3D. In each of FIGS. 3A-3D, the top row (A-C) shows vimentin (green) and the bottom row (D-F) shows TE7 (green); the first column (A and D) shows 10× magnification, the second column (B and E) shows 20× magnification, and the last column (C and F) shows 60× magnification. The constructs of FIG. 3A include ECM, the constructs of FIG. 3B include hydrogel, the constructs of FIG. 3C include ECM and were treated with lyase, and the constructs of FIG. 3D include hydrogel and were treated with lyase.

Figure 4:
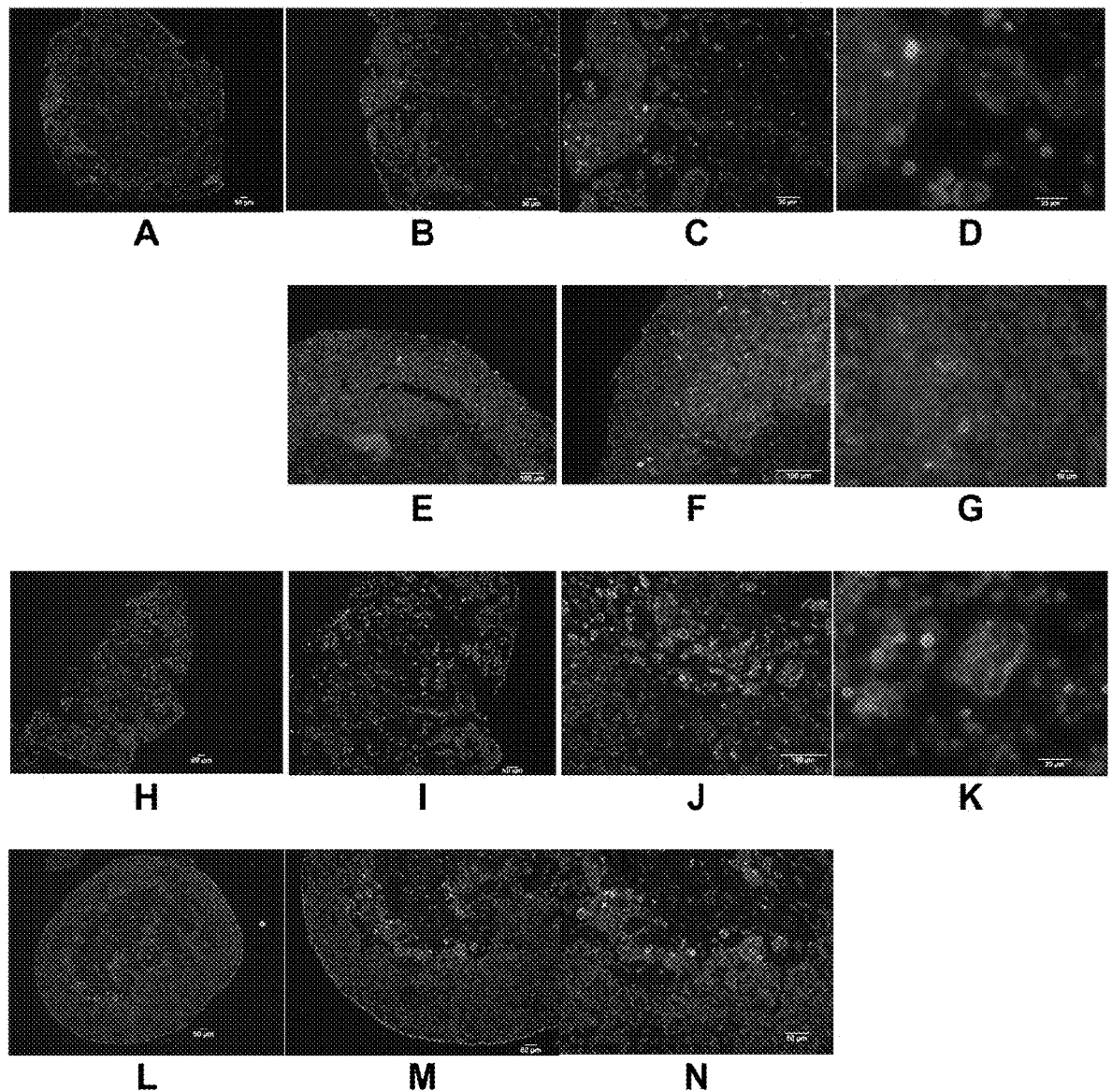
FIG. 4 shows a non-limiting series of representative photomicrographs of the construct of FIG. 1 (day 7 post-fabrication); in this case, photomicrographs depicting constructs stained to visualize the relative positions of normal human mammary fibroblasts and human mammary epithelial cells by antibodies against vimentin (red) and pan cytokeratin (green) as well as DAPI (blue). The first column (A, H, and L) shows 5× magnification, the second column (B, E, I, and M) shows 10× magnification, the third column (C, F, J, and N) shows 20× magnification, and the last column (D, G, and K) shows 60× magnification. The constructs of the first row (A-D) include ECM, the constructs of the second row (E-G) include ECM and were treated with lyase, the constructs of the third row (H-K) include hydrogel, and the constructs of the last row (L-N) include hydrogel and were treated with lyase.

To visualize the relative positions of NHMF and HMEC cells in the construct, tissues were stained with antibodies against vimentin (red) and pan cytokeratin (green) in addition to DAPI (blue). See FIG. 4. As expected, the epithelial cells were concentrated towards the center of the construct. Referring to FIG. 4, the first column (A, H, and L) shows 5× magnification, the second column (B, E, I, and M) shows 10× magnification, the third column (C, F, J, and N) shows 20× magnification, and the last column (D, G, and K) shows 60× magnification; the constructs of the first row (A-D) include ECM, the constructs of the second row (E-G) include ECM and were treated with lyase, the constructs of the third row (H-K) include hydrogel, and the constructs of the last row (L-N) include hydrogel and were treated with lyase.

Figure 5:
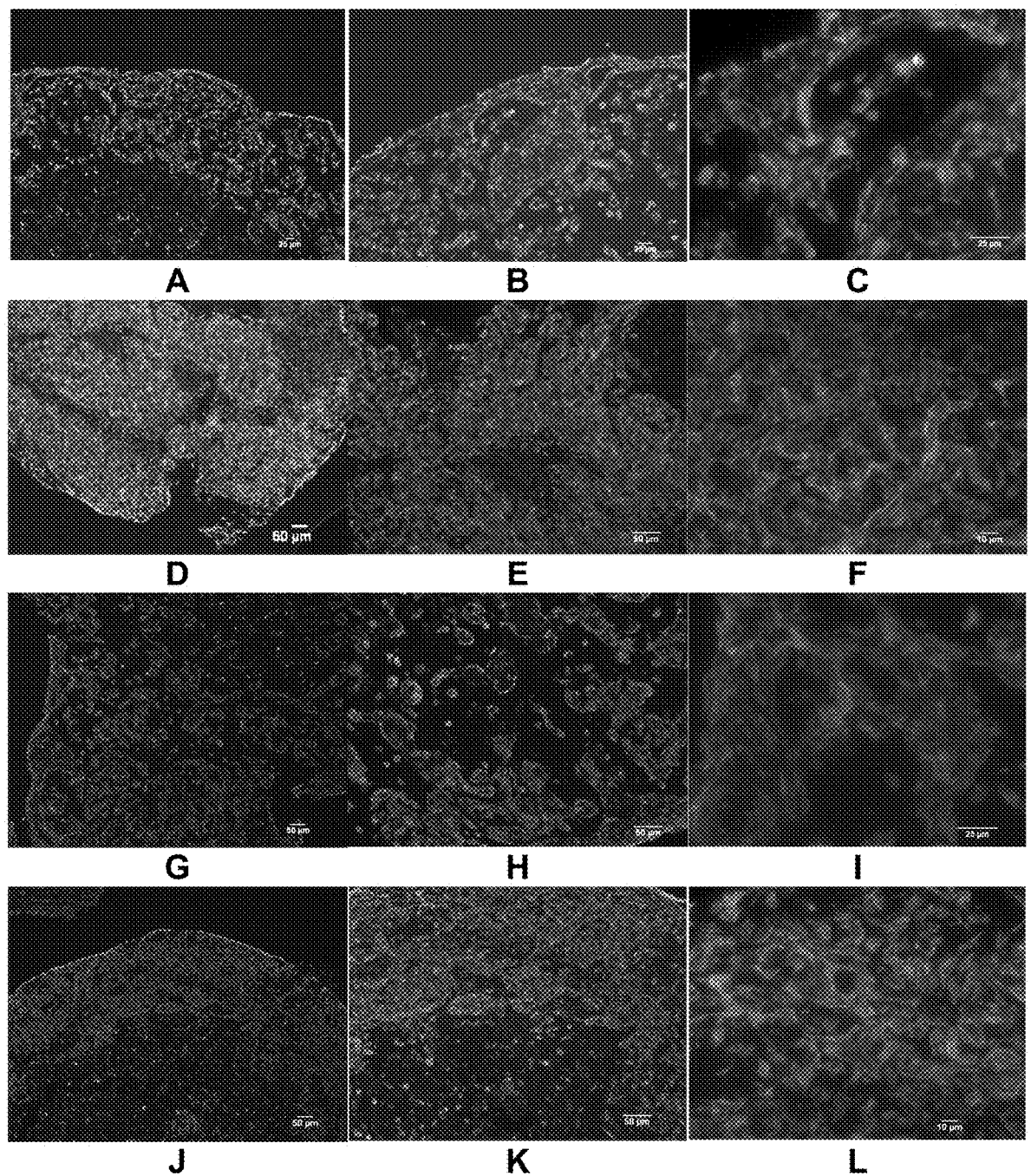
FIG. 5 shows a non-limiting series of representative photomicrographs of the construct of FIG. 1 (day 7 post-fabrication); in this case, photomicrographs depicting constructs stained to visualize the relative positions of normal human mammary fibroblasts and human umbilical vein endothelial cells by antibodies against vimentin (red) and CD31 (green) as well as DAPI (blue). The first column (A, D, G, and J) shows 10× magnification, the second column (B, E, H, and K) shows 20× magnification, and the last column (C, F, I, and L) shows 60× magnification; the constructs of the first row (A-C) include ECM, the constructs of the second row (D-F) include ECM and were treated with lyase, the constructs of the third row (G-I) include hydrogel, and the constructs of the last row (J-L) include hydrogel and were treated with lyase.

To visualize the relative positions of NHMF and HUVEC cells in the construct, tissues were stained with antibodies against vimentin (red) and CD31 (green) as well as DAPI (blue). See FIG. 5. Referring to FIG. 5, the first column (A, D, G, and J) shows 10× magnification, the second column (B, E, H, and K) shows 20× magnification, and the last column (C, F, I, and L) shows 60× magnification; the constructs of the first row (A-C) include ECM, the constructs of the second row (D-F) include ECM and were treated with lyase, the constructs of the third row (G-I) include hydrogel, and the constructs of the last row (J-L) include hydrogel and were treated with lyase.

Figure 6:
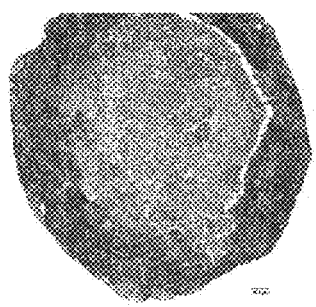
FIG. 6 shows a non-limiting series of representative photomicrographs of the construct of FIG. 1; in this case, photomicrographs depicting constructs stained by Masson's trichrome stain. The first column (A and D) shows 5× magnification, the second column (B and E) shows 10× magnification, and the last column (C and F) shows 20× magnification; the constructs of the first row (A-C) include ECM and were treated with lyase, the constructs of the second row (D-F) include hydrogel and were treated with lyase.
Figure 6:
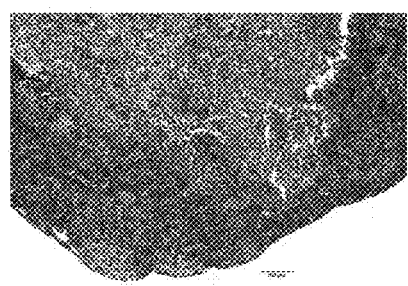
Figure 6:
Figure 6:
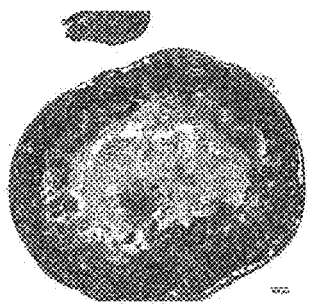
Figure 6:
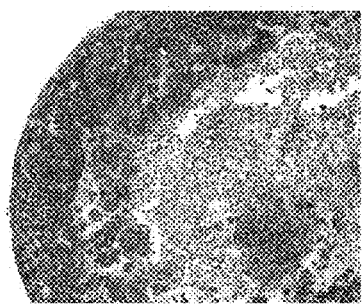
Figure 6:

A robust network of CD31+ cells was found in all analyzed constructs, with some areas demonstrating evidence of microvasculature formation. While the CD31+ cells were found mainly toward the outer surface of the construct, cells were found to be about 1-2 mm to the interior of the construct. To evaluate overall ECM deposition, Masson's trichrome stain was performed. See FIG. 6. Significant ECM deposition was observed in tissues treated with lyase. Referring to FIG. 6, the first column (A and D) shows 5× magnification, the second column (B and E) shows 10× magnification, and the last column (C and F) shows 20× magnification; the constructs of the first row (A-C) include ECM and were treated with lyase, the constructs of the second row (D-F) include hydrogel and were treated with lyase.

Example 2—Engineered Human Breast Tissue Model with Adipose Tissue

Fabrication

Figure 7:
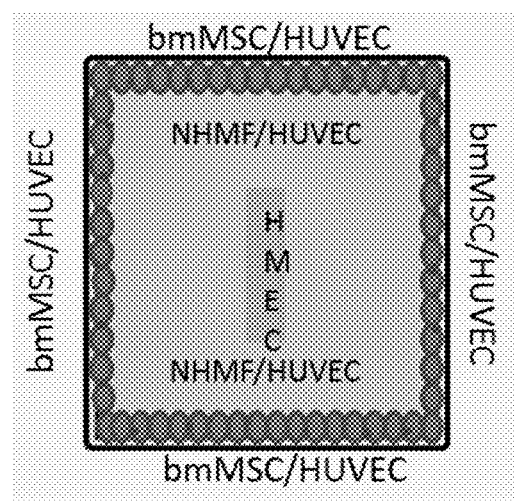
FIG. 7 shows non-limiting examples of a bioprinted breast tissue construct (schematic (A) and photographic (B-D)); in this case, a construct with a border of bone marrow-derived mesenchymal stem cells (differentiated to adipocytes post-fabrication) and human umbilical vein endothelial cells surrounding a strip of human mammary epithelial cells wherein the space between the border and the strip is filled with normal human mammary fibroblasts and human umbilical vein endothelial cells. The constructs are shown directly post printing (B), and at day 10 post-fabrication (C and D).
Figure 7:
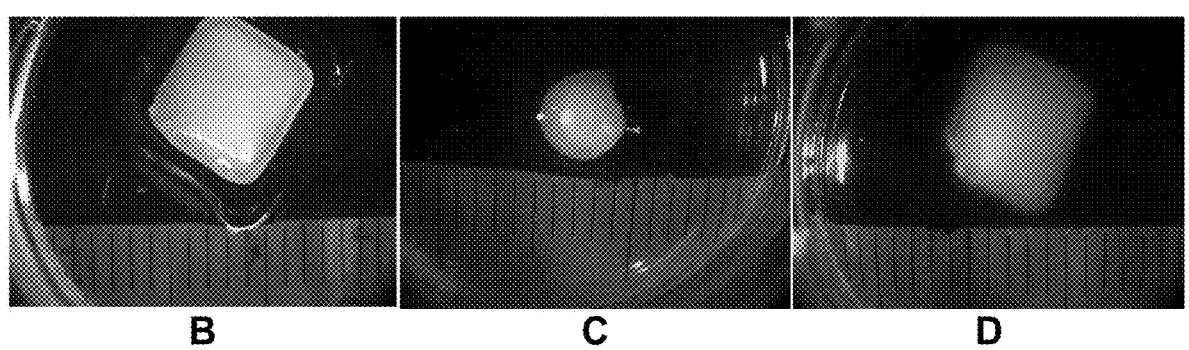

A box with dimensions 5 mm×5 mm×500 μm was bioprinted onto a Transwell membrane in a 6-well tissue culture plate as shown in FIG. 7A (Structure 2). First, a 500 μm stromal bio-ink cylinder composed of 90% bone marrow-derived mesenchymal stem cells (bmMSC) and 10% HUVEC was bioprinted to form a box shape. HMEC cells were mixed with 10% gelatin hydrogel to form an epithelial bio-ink and bioprinted into the middle of the stromal bio-ink box, wherein the HMEC bio-ink did not touch the stromal bio-ink border. A third bio-ink composed of 75% NHMF and 25% HUVEC was used to fill the space between the stromal bio-ink border and the HMEC bio-ink in the middle. Constructs were incubated for 10 days. FIG. 7B depicts Structure 2 immediately post-fabrication and FIGS. 7C and 7D depict Structure 2 at day 10 post-fabrication. The bmMSC were provided with an adipocyte differentiation signal during incubation to generate viable, differentiated human adipocytes.

Results

Figure 8:
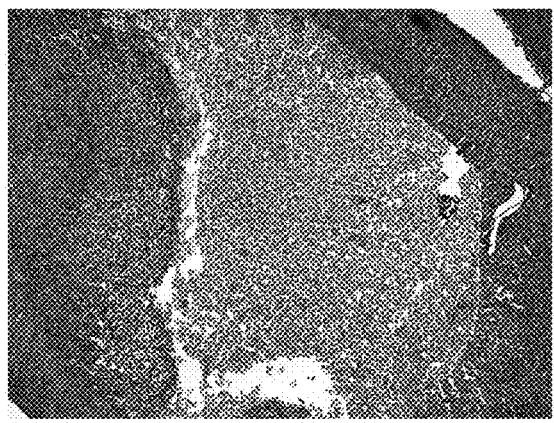
FIG. 8 shows a non-limiting series of representative photomicrographs of the construct of FIG. 7; in this case, photomicrographs depicting Hematoxylin & Eosin (H&E) stained specimens. The first row (A and B) shows 5× magnification, the second row (C and D) shows 10× magnification, and the last row (E and F) shows 20× magnification.
Figure 8:
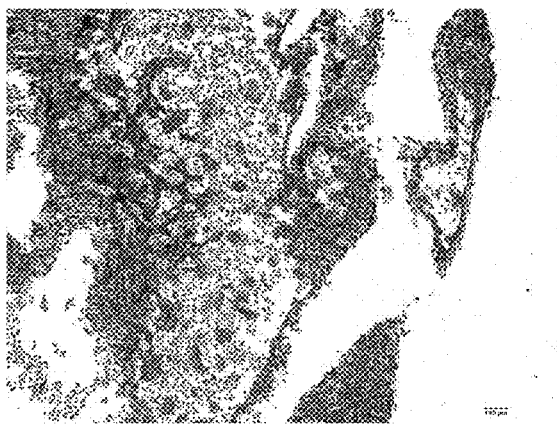
Figure 8:
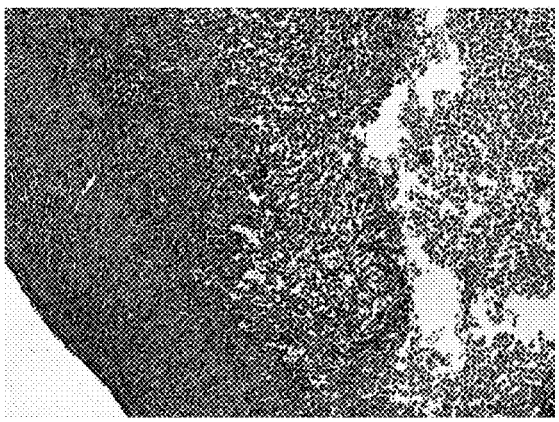
Figure 8:
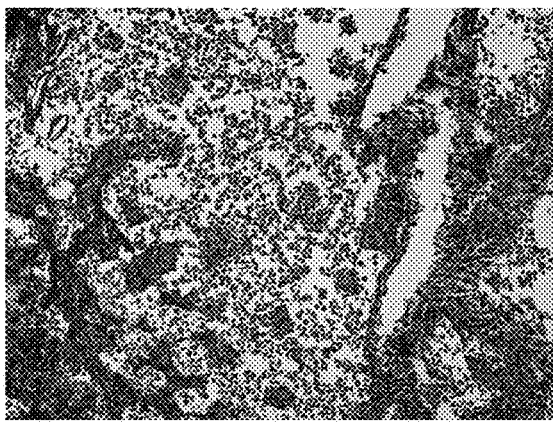
Figure 8:
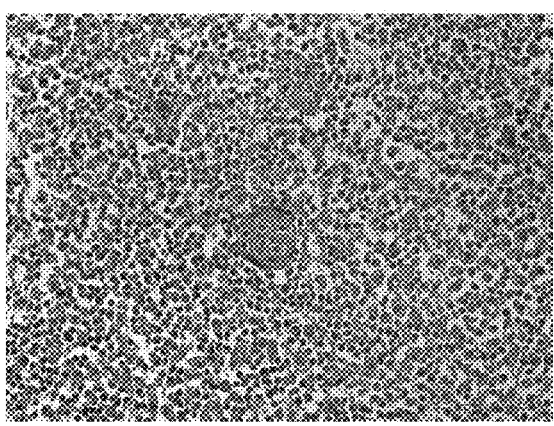
Figure 8:
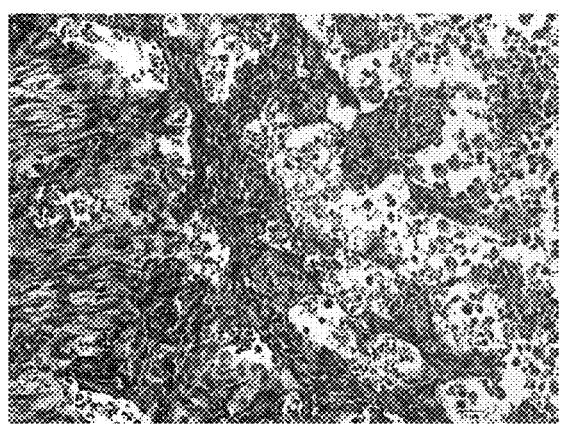

Assessment of Structure 2 was performed by histological staining for cell-type specific markers. A representative H&E stain of Structure 2 is shown in FIG. 8. Referring to FIG. 8, the H&E stained specimens were prepared at day 10 post-fabrication; the first row (A and B) shows 5× magnification, the second row (C and D) shows 10× magnification, and the last row (E and F) shows 20× magnification.

Figure 9:
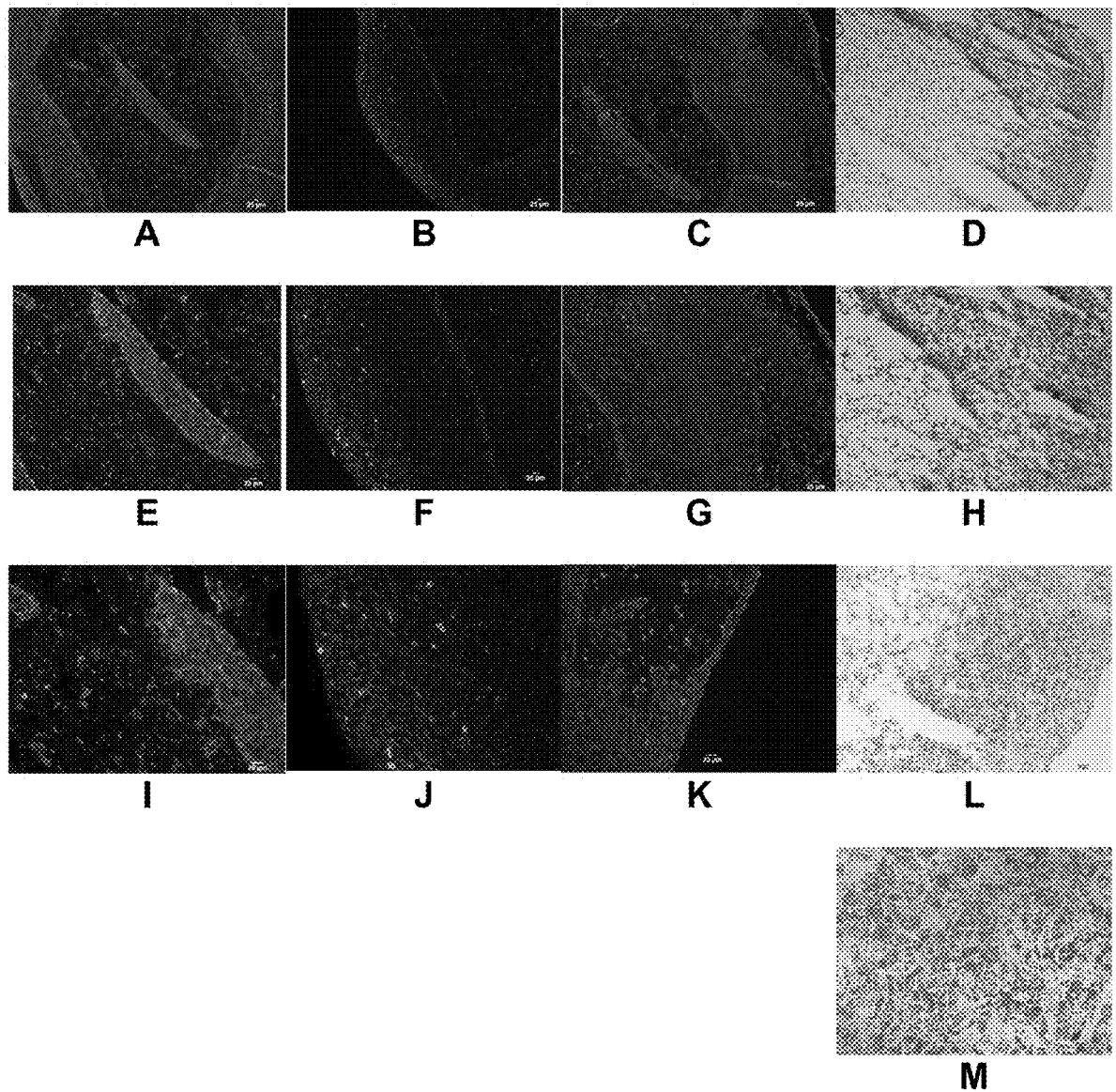
FIG. 9 shows a non-limiting series of representative photomicrographs of the construct of FIG. 7; in this case, photomicrographs depicting constructs stained to visualize endothelial cells, fibroblasts, adipocytes, and epithelial cells by antibodies against CD31, vimentin, FABP4, and pan cytokeratin as well as DAPI. The first row (A-D) shows 5× magnification, the second row (E-H) shows 10× magnification, the third row (I-L) shows 20× magnification, and the last row (M) shows 60× magnification; the constructs of the first column (A, E, and I) were stained for CD31 (green) vimentin (red) as well as treated with DAPI (blue), the constructs of the second column (B, F, and J) were stained for FABP4 (green) as well as treated with DAPI (blue), the constructs of the third column (C, G, and K) were stained for pan cytokeratin (green) vimentin (red) as well as treated with DAPI (blue), and the constructs of the last column (D, H, L, and M) were stained using Oil Red O (cryosectioned).

Staining for several different cell markers is shown in FIG. 9 (CD31, endothelial cells; vimentin, fibroblasts; FABP4, adipocytes; pan cytokeratin, epithelium). Oil Red O staining was used to demonstrate the presence of lipid droplets in adipocytes differentiated from bmMSC on the exterior of the construct.

Referring to FIG. 9, the first row (A-D) shows 5× magnification, the second row (E-H) shows 10× magnification, the third row (I-L) shows 20× magnification, and the last row (M) shows 60× magnification; the constructs of the first column (A, E, and I) were stained for CD31 (green) vimentin (red) as well as treated with DAPI (blue), the constructs of the second column (B, F, and J) were stained for FABP4 (green) as well as treated with DAPI (blue), the constructs of the third column (C, G, and K) were stained for pan cytokeratin (green) vimentin (red) as well as treated with DAPI (blue), and the constructs of the last column (D, H, L, and M) were stained using Oil Red O (cryo-sectioned).

All cell types were present in the structure, with a network of CD31+ endothelial cells forming throughout the construct. Epithelia were confined to the interior of the construct. Markers of adipocyte differentiation (Oil Red O and FABP4) were found toward the outside of the construct, coincident with the presence of bmMSC-derived adipocytes in bio-ink.

Example 3—Engineered Human Breast Cancer Tumor Model

Bioprinted breast cancer constructs were generated in which a cancer cell node, composed of MCF7 breast cancer cells and human umbilical vein endothelial (HUVEC) cells, is surrounded on all sides by a stromal compartment composed of normal human mammary fibroblasts (NHMF), HUVEC cells, and subcutaneous preadipocytes (SPA). Bio-inks were produced by combining cells with a reversibly cross-linkable, alginate-containing hydrogel (Novogel® 3.0 System; Organovo, Calif.).

Figure 10:
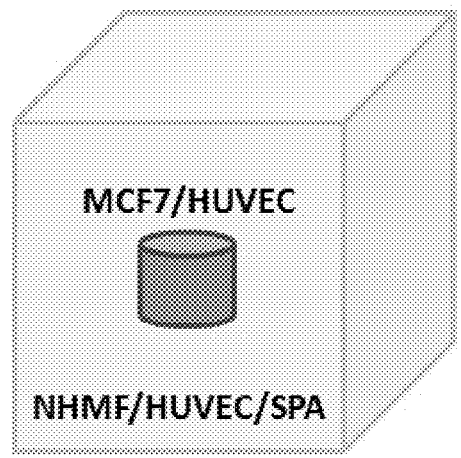
FIG. 10 shows non-limiting examples of a bioprinted breast cancer tumor model (schematic (A) and photographic (B and C)); in this case, a tumor model with a tumor tissue core including breast cancer cells and human umbilical vein endothelial cells surrounded on all sides by stromal tissue including normal human mammary fibroblasts, human umbilical vein endothelial cells, and subcutaneous preadipocytes, which were differentiated to form viable adipocytes.
Figure 10:
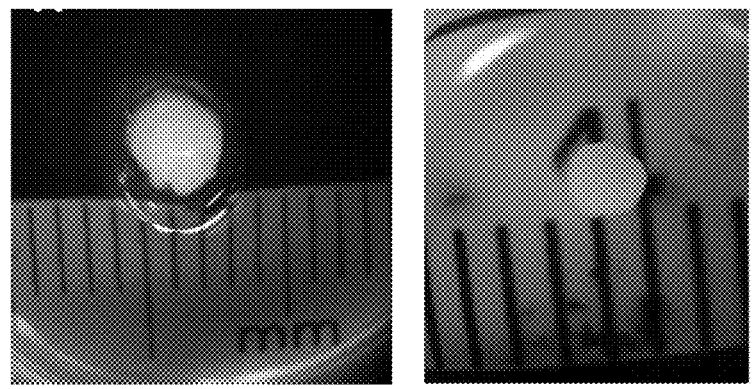

FIG. 10A shows a schematic diagram depicting the construction of the construct (Structure 3). FIG. 10B shows a photograph of the construct immediately after bioprinting and crosslinking of the hydrogel. FIG. 10C shows the construct 2 days after enzymatic treatment to remove the hydrogel, wherein the construct demonstrates condensation of tissue and generation of a smooth, solid nodule.

Cell Culture

Normal human mammary fibroblasts (NHMF) were acquired from ScienCell (Carlsbad, Calif.) and cultured according to the manufacturer's instructions. Human umbilical vein endothelial cells (HUVEC) were acquired from BD Biosciences (San Jose, Calif.) and cultured in EGM-2 endothelial cell media (Lonza, Allendale, N.J.).

Figure 11:
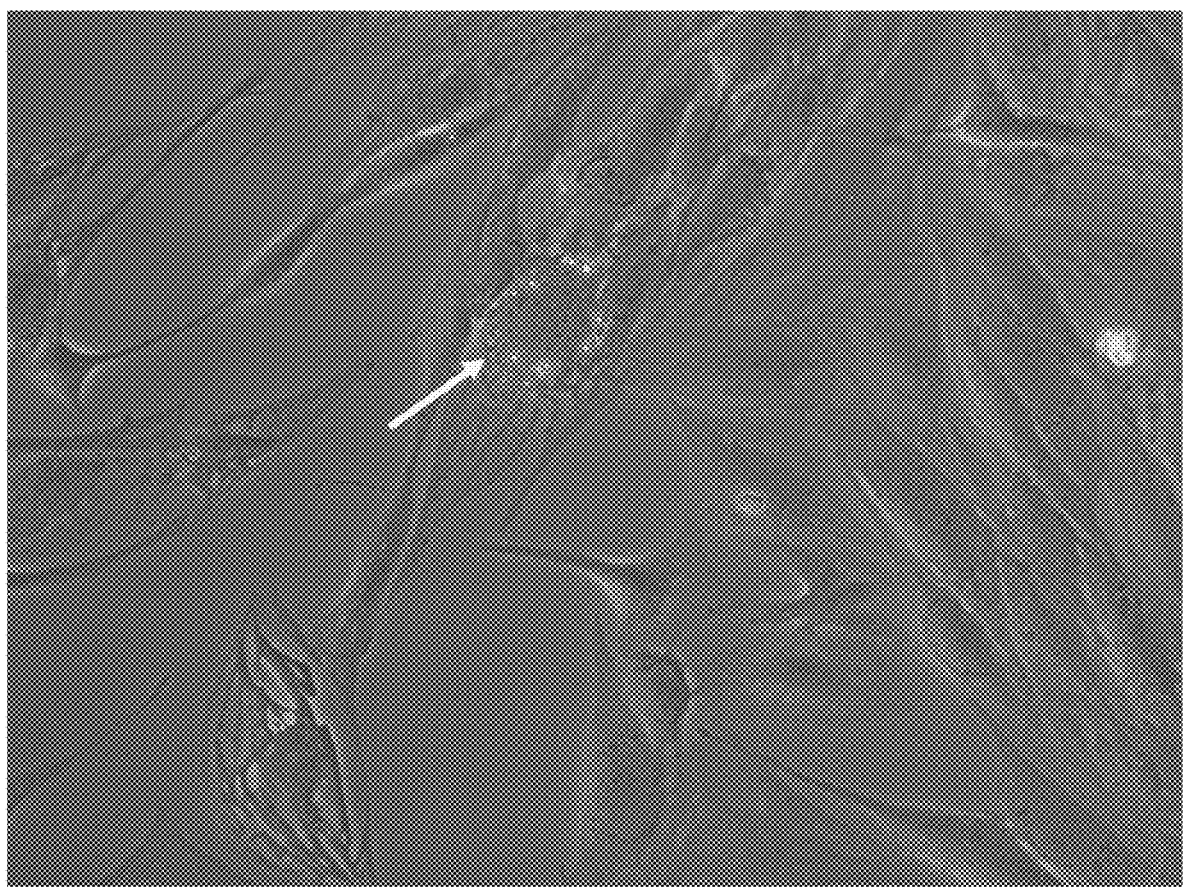
FIG. 11 shows a non-limiting example of pre-differentiated subcutaneous preadipocytes; in this case, subcutaneous preadipocytes exposed to an adipocyte differentiation medium three days prior to fabrication of the tumor model of FIG. 10 and demonstrating early formation of lipid droplets.

Subcutaneous preadipocytes (SPA) were acquired from Zen-Bio (Research Triangle Park, N.C.) and cultured in subcutaneous preadipocyte medium for expansion. Three days prior to bioprinting, cells were cultured in adipocyte differentiation medium (Zen-Bio). FIG. 11 shows early lipid droplets seen accumulating within cells (arrow) by the day of bioprinting.

MCF7 cells were acquired from Sigma-Aldrich (St. Louis, Mo.) or the American Type Culture Collection (Manassas, Va.) and cultured according to the manufacturer's instructions.

Bioprinting

The stromal compartment of the constructs was comprised of 65% NHMF, 25% HUVEC, and 10% SPA (partially pre-differentiated). The cancer compartment of the constructs was comprised of 75% MCF7, 25% HUVEC. For each compartment, cells were mixed together at the indicated ratio and resuspended in Novogel® 3.0 at a concentration of 150 million cells/ml. Constructs were printed as 3 layered structures with a dimension of 3 mm×3 mm×0.75 mm. Immediately following bioprinting, constructs were stabilized via crosslinking. After 2 minutes, the calcium crosslinking solution was aspirated and replaced with culture media. After 2 days in culture, constructs were treated overnight with enzyme dissolved in culture media to remove the Novogel® 3.0. Constructs were then incubated for up to 9 additional days.

Treatment of Constructs with Chemotherapy Compounds

All compounds were acquired from Sigma-Aldrich and were dissolved in DMSO. Compounds were diluted to a final concentration of 10 μM or 100 μM in media. The final DMSO concentration was 0.1%, which was used for vehicle treatment. Constructs were assessed for metabolic activity by alamarBlue assay (Life Technologies, Carlsbad, Calif.) or CellTiter Glo assay (Promega, Madison, Wis.). Constructs were treated for 24 hours for labeled compound uptake studies, or for 4 days for assessment of metabolic activity.

Leptin ELISA

Conditioned medium from constructs was collected daily for 9 days. Media was diluted 1:2 and assessed for leptin secretion according to the manufacturer's instructions (Life Technologies).

Histology

Constructs were fixed in situ in 2% paraformaldehyde solution (2% paraformaldehyde, 10 mM calcium chloride, 50 mM sucrose in PBS) for 24 hours at room temperature. After 24 hours, the fixation solution was removed and replaced with 70% ethanol. Constructs were processed for paraffin embedding using an automated tissue processor (Tissue-Tek, Sakura Finetek Europe BV, the Netherlands). Following infiltration with paraffin, constructs were embedded in paraffin molds and 5 μm sections were generated using a rotary microtome (Jung Biocut 2035, Leica Microsystems, Buffalo Grove, Ill.). For hematoxylin and eosin staining, slides were dewaxed in xylene and rehydrated through 100%, 95%, 70%, and 50% ethanol and rinsed in distilled water. Slides were immersed in Gill's hematoxylin (Fisher Scientific, Pittsburgh, Pa.). Following rinsing with distilled water, slides were briefly immersed in 0.2% v/v ammonium hydroxide. After rinsing with distilled water, slides were immersed in aqueous eosin solution (American MasterTech). Slides were then dehydrated through an ethanol gradient, cleared in xylene, and mounted with resinous mounting media (CytoSeal, Fisher Scientific). Masson's trichrome stain was performed according to the manufacturer's instructions (American MasterTech).

For immunohistochemical analysis, slides were dewaxed in xylene and rehydrated by sequentially immersing them in 100, 95, 70, and 50% ethanol before finally washing in distilled water. Rehydrated sections were subjected to heat-mediated antigen retrieval in 10 mM sodium citrate pH 6.0 using a standard microwave oven to heat the solution and slides to a subboil followed by slow cooling for 30 minutes. Slides were then blocked with 10% goat serum in Tris-buffered saline (TBS) for 1 hour, followed by incubation with primary antibodies overnight at 4° C. The following primary antibodies were utilized: mouse anti-cytokeratin 8 (1:100; Abcam, Cambridge, Mass.); rabbit anti-CD31 (1:100; Abcam); mouse anti-TE7 (1:250; EMD Millipore, Billerica, Mass.); mouse anti-collagen 4 (1:250; Abcam). Sections were then washed three times in TBS with 0.1% Tween 20 and incubated with AlexaFluor 488 or AlexaFluor 568-conjugated secondary antibodies (Life Technologies, Carlsbad, Calif.) diluted 1:200 in TBS. Sections were then washed three times in TBS-0.1% Tween 20, rinsed with distilled water, and mounted with DAPI-containing mounting media (Vector Labs, Burlingame, Calif.).

Preparation of Constructs for Cryo-Sectioning

Constructs were rinsed once with DPBS, immersed in Tissue-Tek OCT compound (Sakura Finetek Europe B.V., The Netherlands), and flash frozen. Frozen blocks were then sectioned at 5 µm on a cryostat (Leica Cryocut 1800, Leica Microsystems). Sectioned slides were snap fixed in −20° C. liquid acetone and allowed to air dry for 20 minutes at room temperature. For Oil Red O staining, slides were rehydrated in distilled water and immersed in 60% isopropanol for 2 minutes. Slides were stained with 0.3% w/v Oil Red O (Sigma-Aldrich) in 60% isopropanol for 15 minutes at room temperature, followed by rinsing with 60% isopropanol for 1 minute. Slides were immersed briefly in Gill's hematoxylin to counterstain. Slides were rinsed with distilled water and mounted with aqueous media (American MasterTech). For imaging of fluorescent compounds, slides were mounted with DAPI-containing mounting media.

Microscopy

H&E, Trichrome, and Oil Red O-stained slides were imaged using a Zeiss Axioskop microscope (Zeiss, Jena, Germany). Images were acquired with an Insight 2 camera and Spot 5.0 software (Diagnostic Instruments, Inc., Sterling Heights, Mich.). Fluorescently stained slides were imaged with a Zeiss Axiolmager microscope and images were acquired with a Zeiss ICM-1 camera and Zen Pro software.

Results

Figure 12:
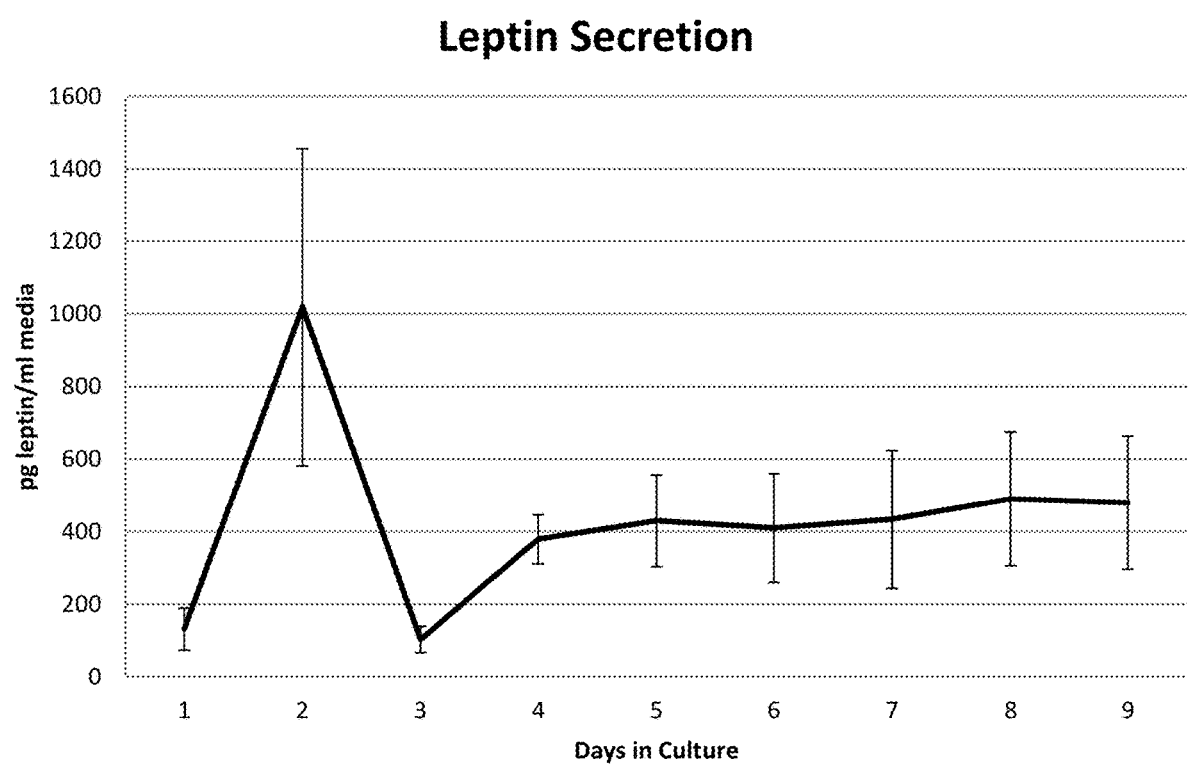
FIG. 12 shows a non-limiting example of a line graph depicting leptin secretion over time by the tumor model of FIG. 10, which suggests continued differentiation of adipocytes within the bioprinted construct.

The bioprinted breast cancer tumor models demonstrated leptin secretion over time. Conditioned medium from bioprinted breast cancer constructs was collected daily for 9 days and assessed for leptin secretion by ELISA assay. Leptin was produced throughout the 9 day culture period, which is reflective of continued differentiation of preadipocytes following bioprinting. See FIG. 12.

Figure 13:
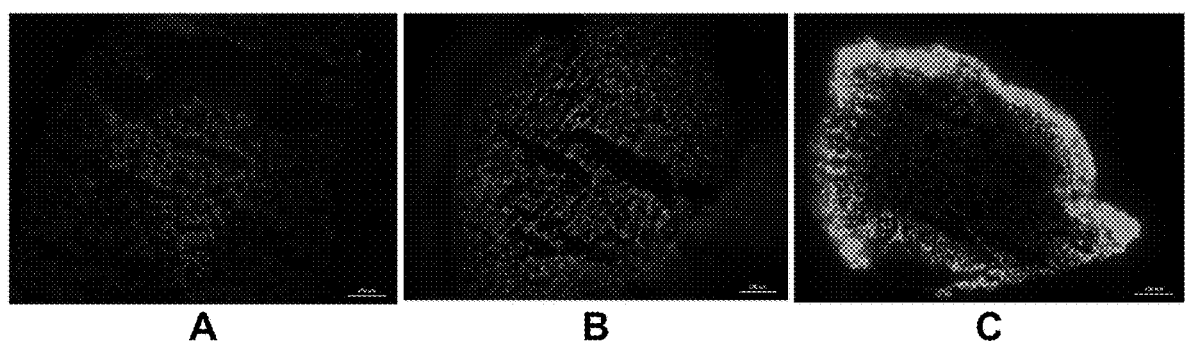
FIG. 13 shows non-limiting exemplary photomicrographs of the tumor model of FIG. 10; in this case, photomicrographs depicting retention of the bioprinted compartmentalized architecture and penetration of a drug compound that mimics observations in native tissue. (A) shows a tissue section stained for MCF7 marker cytokeratin 8; (B) shows a construct treated with OregonGreen 488 fluorphore alone; and (C) shows a construct treated with OregonGreen 488-Paclitaxel.

Treatment of the bioprinted cancer tumor models with labeled chemotherapy compounds demonstrated retention of the construct architecture and a native-like pattern of drug penetration. Constructs were treated with 100 µM compound for 24 hours and cryo-sectioned throughout to assess penetration of labeled drugs. FIG. 13A shows a tissue section stained for cytokeratin 8 as a marker of MCF7 breast cancer cells, indicating retention of cancer cells at the center of the construct. FIG. 13B shows a construct treated with Oregon-Green 488 fluorphore alone, and fluorescence was observed throughout the construct. FIG. 13C shows a construct treated with OregonGreen 488-Paclitaxel, and penetration of the compound was limited to the outer ~200 µm of the construct.

Figure 14:
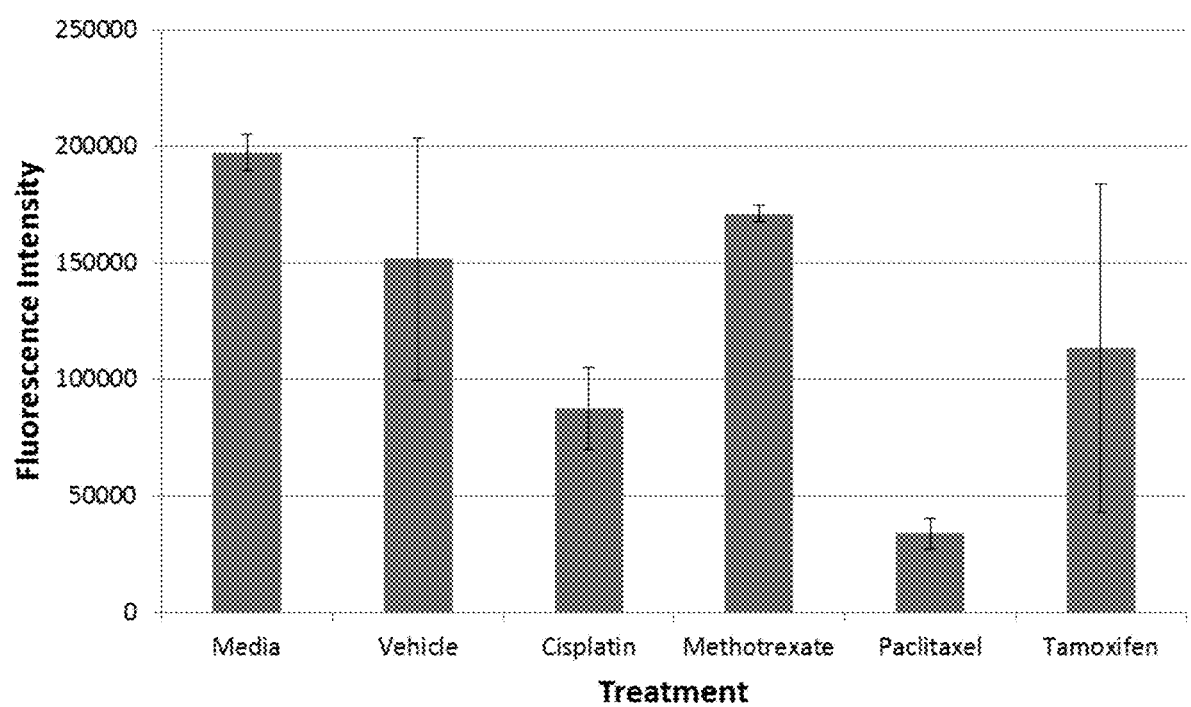
FIG. 14 shows a non-limiting example of a bar graph depicting construct viability of the tumor model of FIG. 10 subsequent to treatment with various drug compounds and controls.

Assessment of construct viability following drug treatment demonstrated native-like drug response. Constructs were treated with 10 µM compound for 3 days, followed by 100 compound for 24 hours. Referring to FIG. 14, viability was assessed by alamarBlue assay, with higher fluorescence intensity indicative of metabolically active cells. Cisplatin and paclitaxel decreased construct viability relative to media or vehicle controls.

Example 4—Engineered Human Breast Cancer Tumor Model

Fabrication

Figure 15:
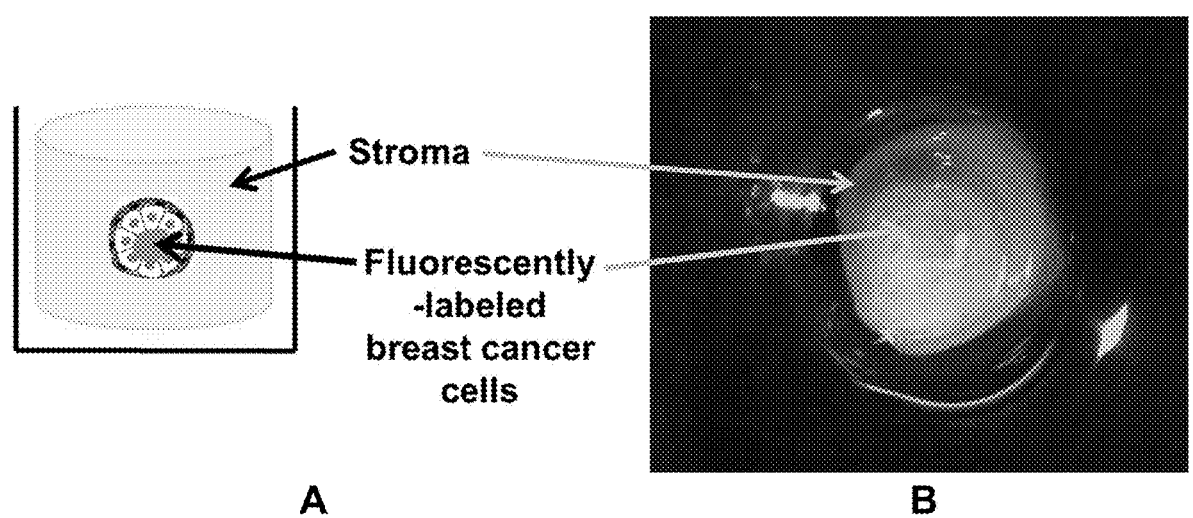
FIG. 15 shows non-limiting examples of a bioprinted breast cancer tumor model (schematic and photographic); in this case, a tumor model with a nodule of human breast cancer cells surrounded by a stromal compartment including endothelial cells, fibroblasts, and adipocytes.

Breast cancer tumor models were bioprinted according to the schematic diagram shown in FIG. 15A (Structure 4). The breast cancer tumor models included a nodule of human breast cancer cells surrounded by a physiologically-relevant stromal layer, which included human adipocytes differentiated from human mesenchymal stem cells, human mammary fibroblasts, and human endothelial cells. The adipocytes were derived from mesenchymal stem cells which were isolated an exposed to an adipocyte differentiation signal prior to preparation of the bio-ink and bioprinting. FIG. 15B shows a photograph of the construct immediately after bioprinting.

Results

Figure 16:
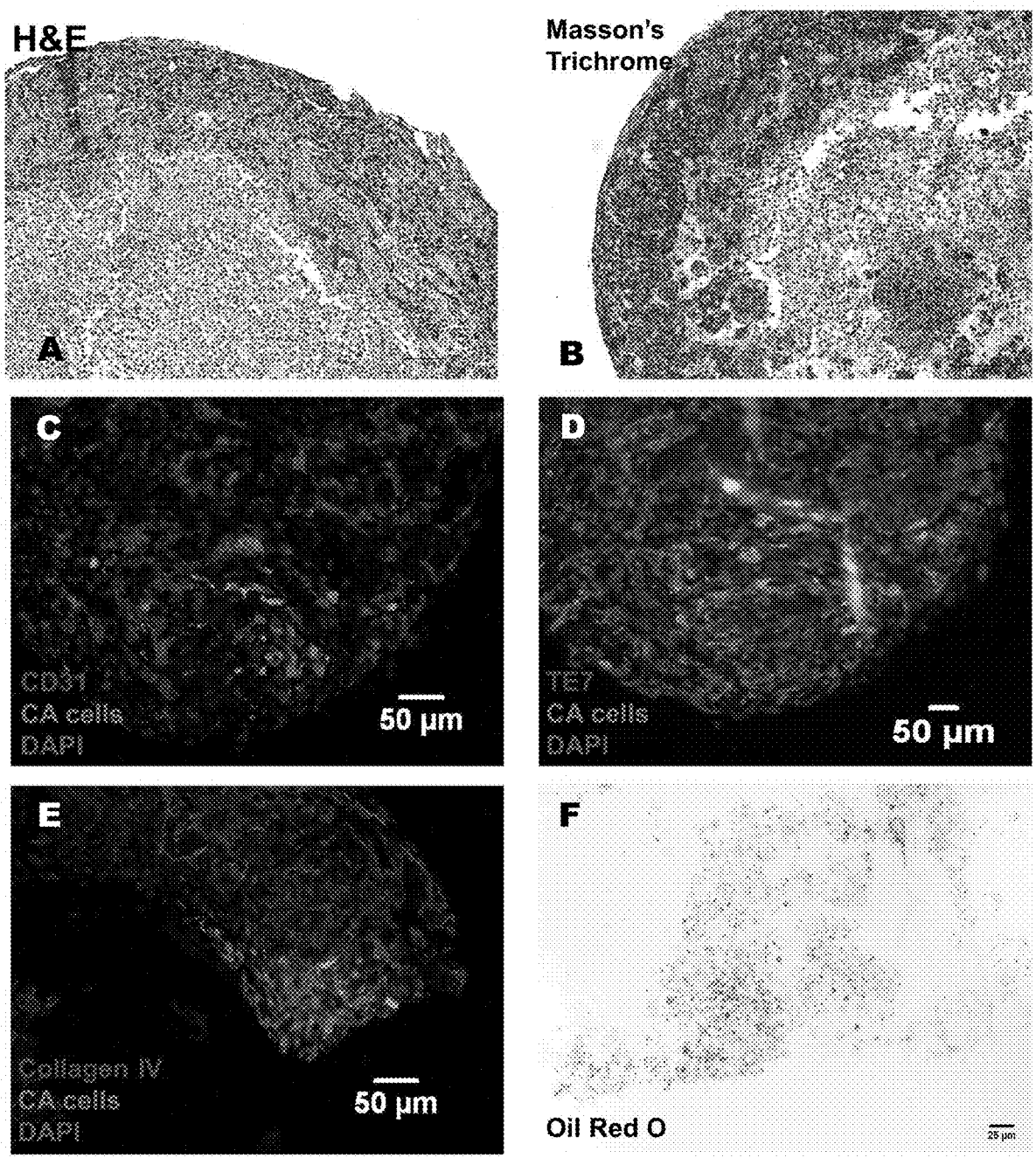
FIG. 16 shows non-limiting exemplary photomicrographs of the tumor model of FIG. 15; shown are photomicrographs depicting histological analysis of the tissue architecture and relative positions of various cell types, breast cancer cells are labeled with CellTracker Green CMFDA (C-E; green) and nuclei are labeled with DAPI (C-E; blue). Stainings shown are H&E (A), Masson's trichrome (B), endothelial cells (C; CD31, red), fibroblasts (D; TE7, red), collagen IV (E; red), and Oil Red O (F).
Figure 17:
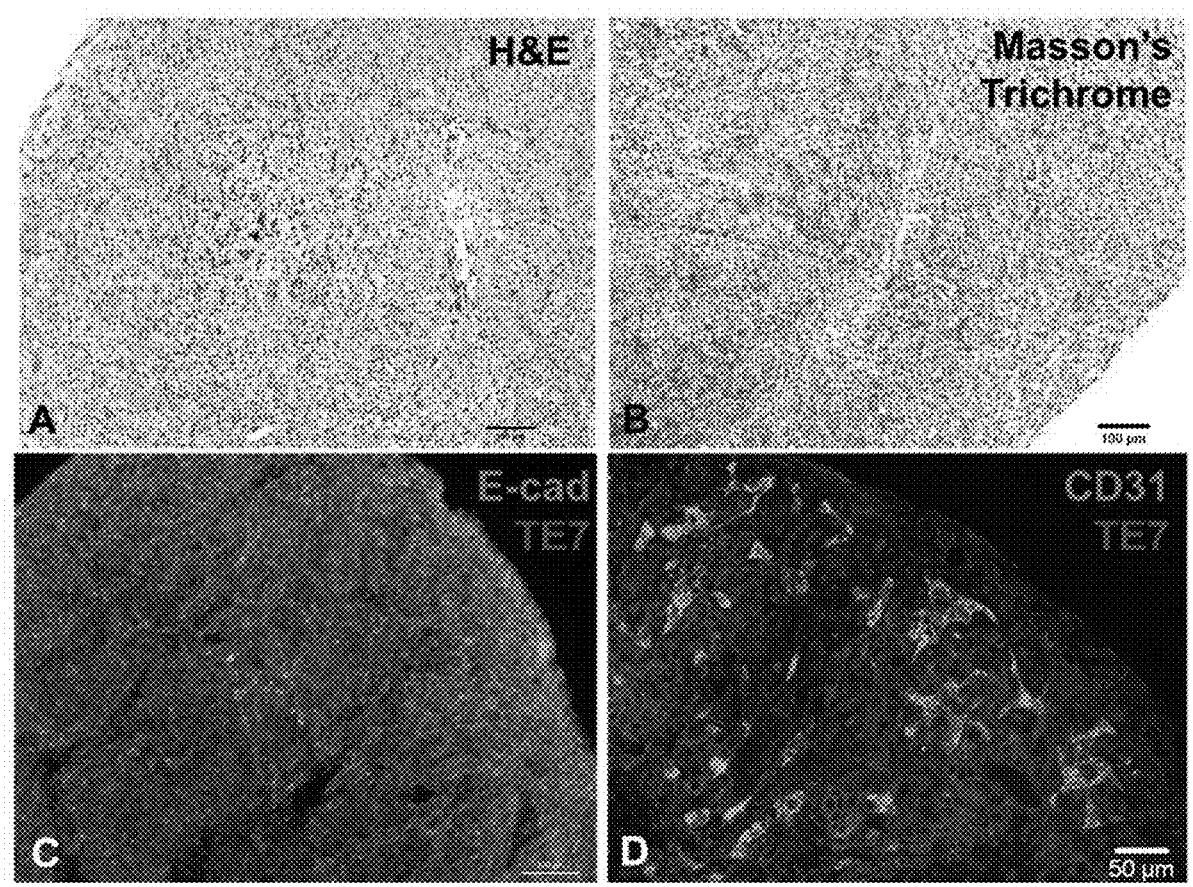
FIG. 17 shows non-limiting exemplary photomicrographs of the tumor model of FIG. 15; in this case, photomicrographs depicting histological analysis of the tissue architecture including, ECM, cell types, stromal compartment, and microvasculature. The top row depicts H&E staining (A) and Masson's trichrome staining (B). In the bottom row, E-cadherin (green) and TE7 (red) staining indicates cancer cells and fibroblasts, respectively (C) and CD31 (green) staining indicates areas of microvasculature formation in the stromal compartment containing fibroblasts (TE7, red) (D).

Histological analysis of Structure 4 was performed by staining for cell-type specific markers in order to assess tissue architecture and relative positions of cell types. Referring to FIG. 16, the top row depicts H&E staining (A) and Masson's trichrome staining (B) wherein breast cancer cells were labeled with CellTracker Green CMFDA. FIG. 16C shows a tissue stained for endothelial cells (CD31, red), cancer cells (green) and further treated with DAPI. FIG. 16D shows a tissue stained for fibroblasts (TE7, red), cancer cells (green) and further treated with DAPI. FIG. 16E shows a tissue stained for collagen IV (red), cancer cells (green) and further treated with DAPI. Referring to FIG. 17, the top row depicts H&E staining (A) and Masson's trichrome staining (B) wherein collagen is indicated by blue staining. In the bottom row, E-cadherin (green) and TE7 (red) staining indicates cancer cells and fibroblasts, respectively (C) and CD31 (green) staining indicates areas of microvasculature formation in the stromal compartment containing fibroblasts (TE7, red) (D).

Figure 18:
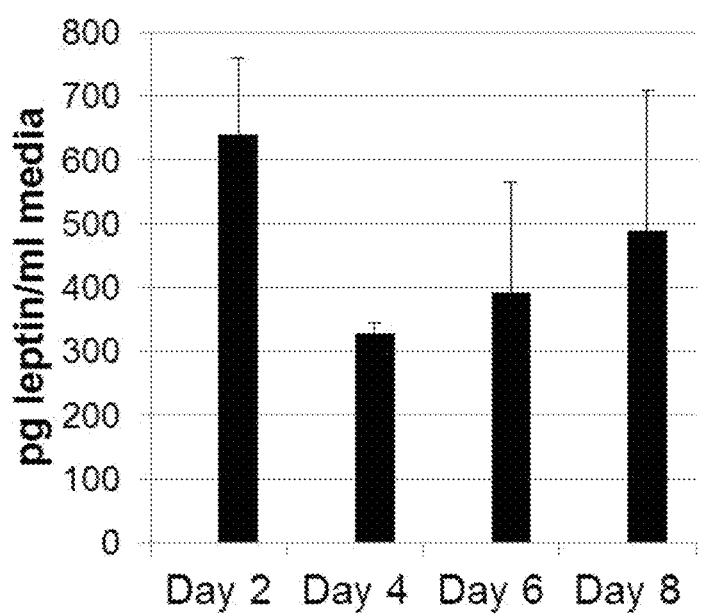
FIG. 18 shows a non-limiting example of a bar graph depicting leptin secretion over time (day 2 post-fabrication to day 8 post-fabrication) by the tumor model of FIG. 15, which suggests continued differentiation of adipocytes within the bioprinted construct.

The adipocytes in the construct secreted leptin, which suggests continued differentiation of adipocytes within bioprinted constructs. Referring to FIG. 18, conditioned media from constructs was collected every 24 hours and assessed for leptin secretion by ELISA. Data shown represents the mean±standard deviation.

Figure 19:
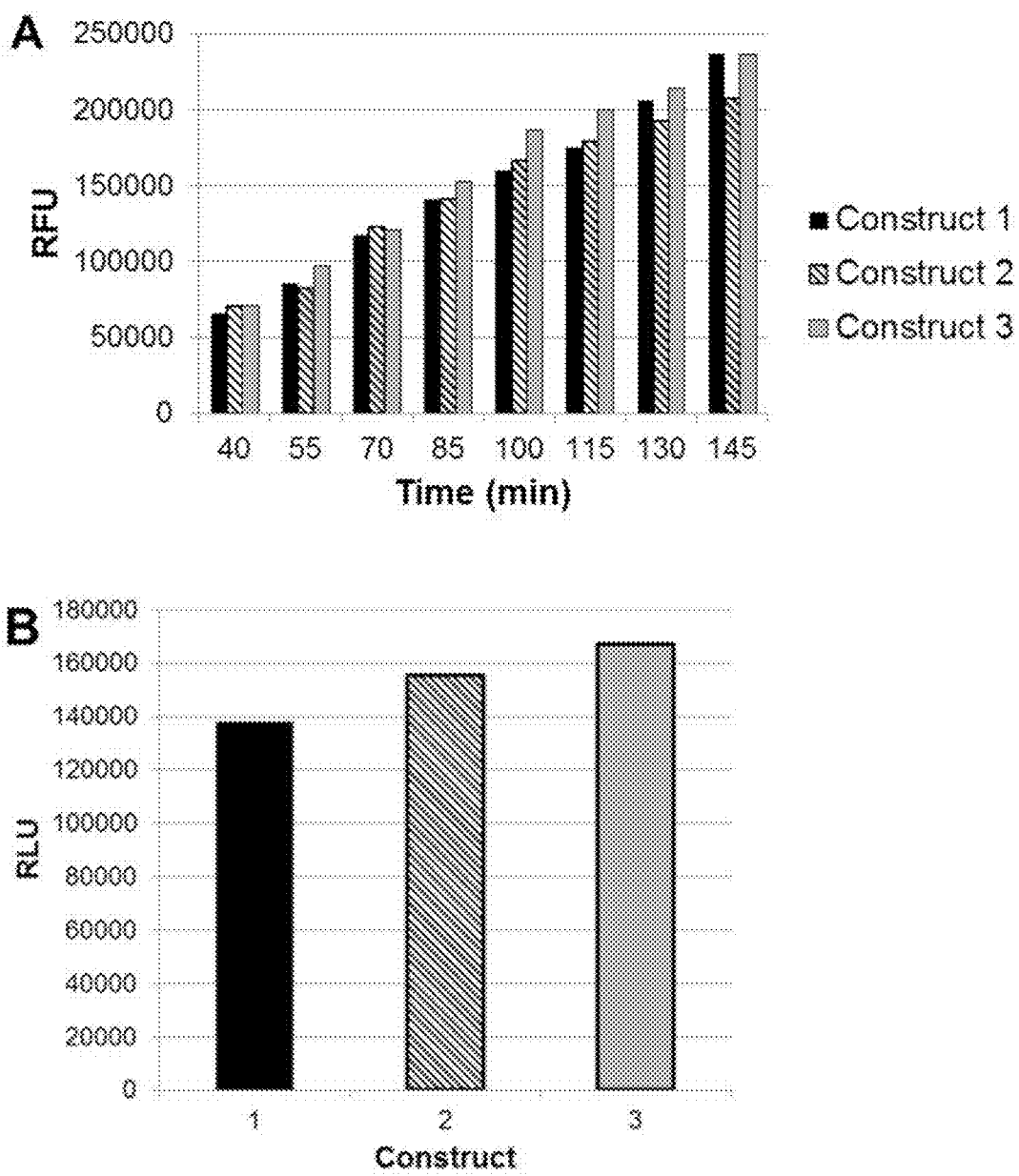
FIG. 19 shows non-limiting examples of bar graphs depicting two metabolism assays of three of the tumor models of FIG. 15, both metabolism assays demonstrate low construct to construct variability.

In order to assess construct to construct variability, metabolism assays were performed on three breast cancer tumor models. Referring to FIG. 19, three individual tumor models were evaluated for metabolism of alamarBlue substrate as a function of time (A) and three individual tumor models were solubilized in CellTiter Glo reagent and assessed for relative luciferase intensity (B). Low construct-to-construct variability was observed by cell metabolism assays.

Figure 20:
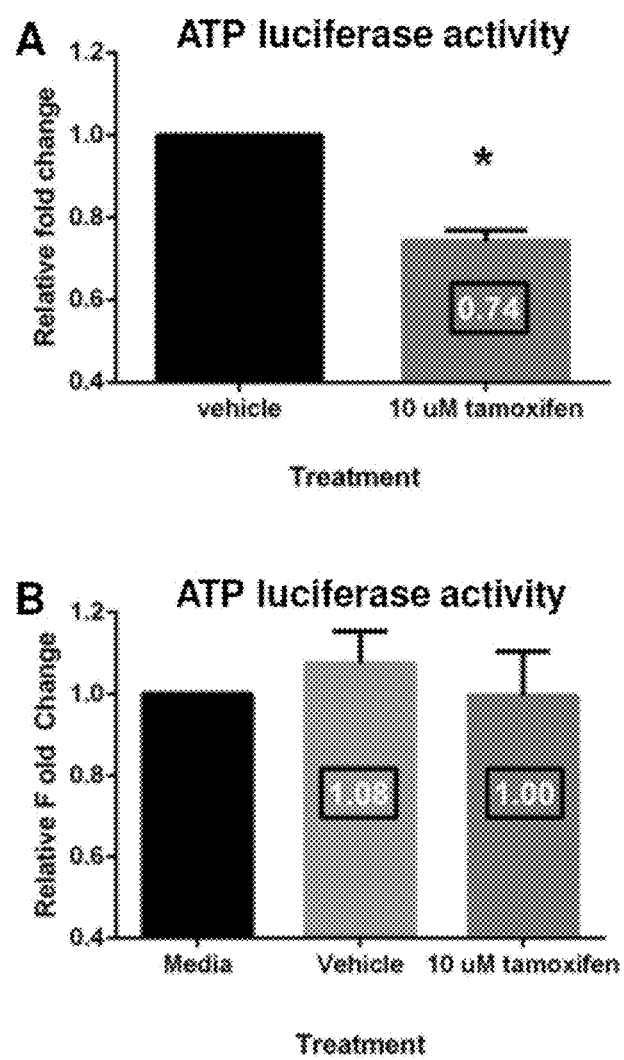
FIG. 20 shows non-limiting examples of bar graphs depicting a drug response assay (tamoxifen) of the tumor model of FIG. 15 compared to a two-dimensional breast cancer cell culture.

The breast cancer tumor models were exposed to chemotherapy compounds in order to access drug response. Referring to FIG. 20, breast cancer cells grown in two-dimensional cell culture (A) and the bioprinted breast cancer tumor models (B) were treated with media alone, DMSO, or 10 µM tamoxifen for 48 hours and assessed for viability by ATP luciferase assay. For each graph, * indicates p<0.05 for treatment compared to control. Isolated two-dimensional cancer cells were more susceptible to tamoxifen-induced toxicity than cells incorporated into three-dimensional bioprinted constructs when treated with the same dose of tamoxifen for the same duration.

Figure 21:
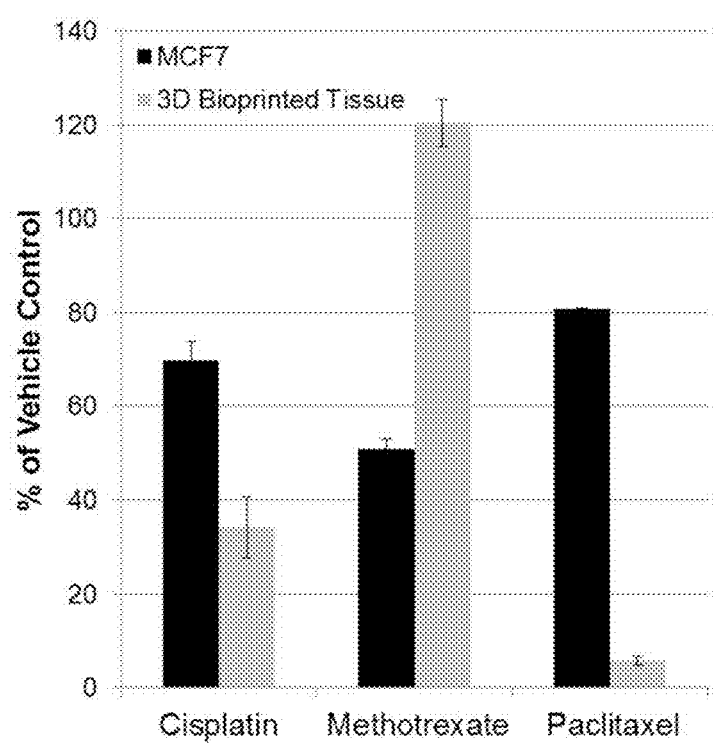
FIG. 21 shows a non-limiting example of a bar graph depicting metabolic activity of the tumor model of FIG. 15 following treatment with chemotherapeutic compounds compared to MCF7 cells alone.

Referring to FIG. 21, metabolic activity following treatment with 100 µM chemotherapeutic compounds was also assessed. MCF7 cells alone (black bars) or the breast cancer tumor models (gray bars) were treated with compounds for 48 hours (MCF7) or daily for 4 days (three-dimensional bioprinted breast cancer tumor models) and assessed for viability by CellTiter Glo ATP Luciferase assay. Data shown represent the average percent of vehicle control±standard deviation.

Figure 22:
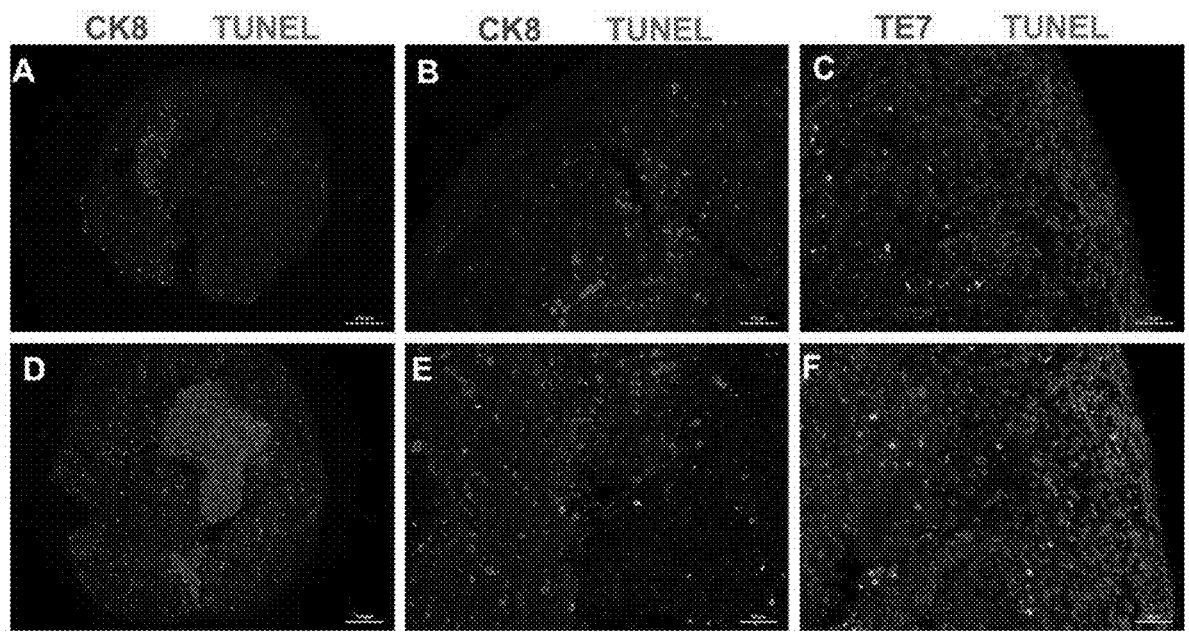
FIG. 22 shows non-limiting exemplary photomicrographs of the tumor model of FIG. 15; in this case, photomicrographs depicting assessment of apoptosis following treatment with cisplatin. Bioprinted tissues were treated with vehicle (A-C) or 100 µM cisplatin (D-F) for 4 days. The first (A and D) and second (B and E) columns depict tissues assessed for apoptosis by TUNEL staining (green) and markers for cancer cells (CK8, red). The last (C and F) column depicts tissues assessed for apoptosis by TUNEL staining (green) and markers for fibroblasts (TE7, red).

Referring to FIG. 22, bioprinted tissues were treated with vehicle (A-C) or 100 µM cisplatin (D-F) for 4 days. The first (A and D) and second (B and E) columns depict tissues assessed for apoptosis by TUNEL staining (green) and markers for cancer cells (CK8, red). The last (C and F) column depicts tissues assessed for apoptosis by TUNEL staining (green) and markers for fibroblasts (TE7, red). FIG. 22 demonstrates that cisplatin induces greater apoptosis in the stromal compartment of bioprinted tissues than in the cancer compartment.

Example 5—Engineered Adipose Tissue

Fabrication

Bio-ink composed of 90% bone marrow-derived mesenchymal stem cells (precursor to adipocytes) and 10% HUVEC was prepared. The ink was deposited with a Novogen Bioprinter® (Organovo; San Diego, Calif.) as a box with no other cell types present and allowed to mature for 10 days in adipogenic differentiation media.

Results

The matured adipose tissue was stained with Oil Red O, a marker of neutral lipids. FIG. 23 shows a photomicrograph of the stained tissue demonstrating significant lipid production.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Example 6—Engineered Human Breast Cancer Tumor Model with Stromal Components in the Tumor Tissue Compartment A three-dimensional breast cancer tumor model was constructed with stromal (65% NHMF, 25% HUVEC, 10% SPA in Novogel® 3.0, 150 million cells/ml) and tumor (75% MCF7, 25% HUVEC in Novogel® 3.0, 300 million cells/ml) tissue compartments. NHMF=normal human mammary fibroblasts, HUVEC=Human umbilical vein endothelial cells, SPA=normal human pre-adipocytes, and MCF7=breast cancer cell line.

Figure 24:
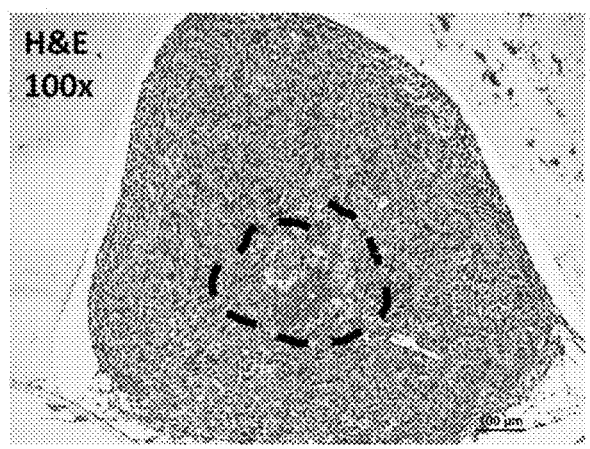
FIG. 24 shows non-limiting exemplary photomicrographs of a breast cancer tumor model; in this case, photomicrographs depicting histological characterization, by H&E (A and B) and Trichrome (C) staining, of a breast cancer tumor model featuring inclusion of stromal in the tumor portion of the tissue.
Figure 24:
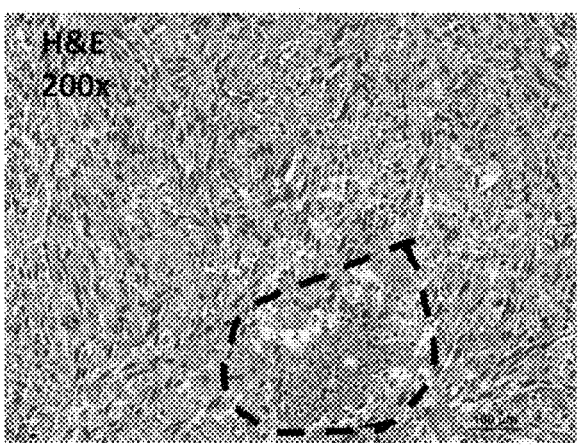
Figure 24:
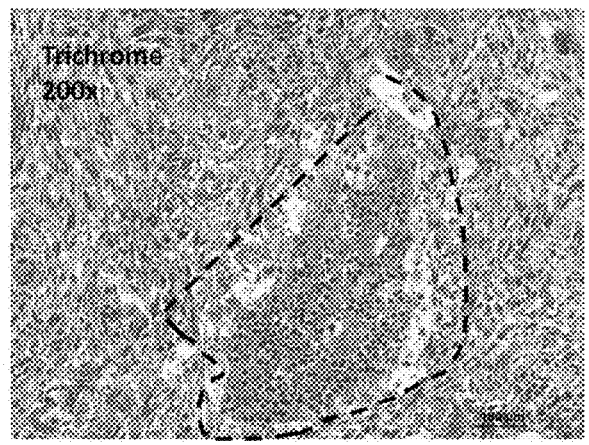

The breast cancer tumor model was histologically characterized. See FIG. 24 (tumor compartment=area within dashed lines). Note the inclusion of stromal components (namely HUVEC) in the tumor tissue compartment. The tissue was cellularly dense and viable (H&E; FIGS. 24A and B) and producing collagen (Trichrome FIG. 24C; blue color=collagen deposition).

Figure 25:
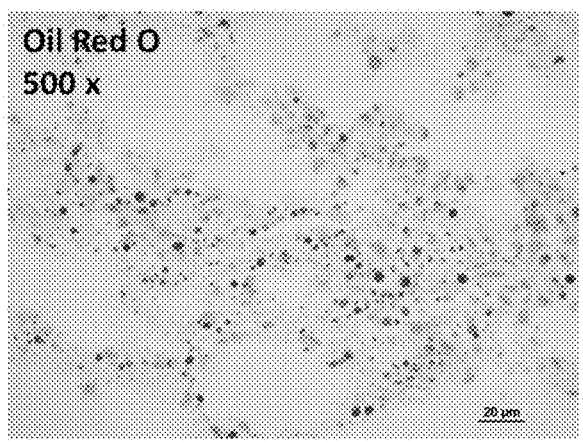
FIG. 25 shows non-limiting exemplary photomicrographs of a breast cancer tumor model; in this case, photomicrographs depicting histological characterization, by Oil Red O (A) staining, CK18/PCNA staining (B), and CD31/PCNA staining (C), of a breast cancer tumor model featuring inclusion of stromal cells in the tumor portion of the tissue.
Figure 25:
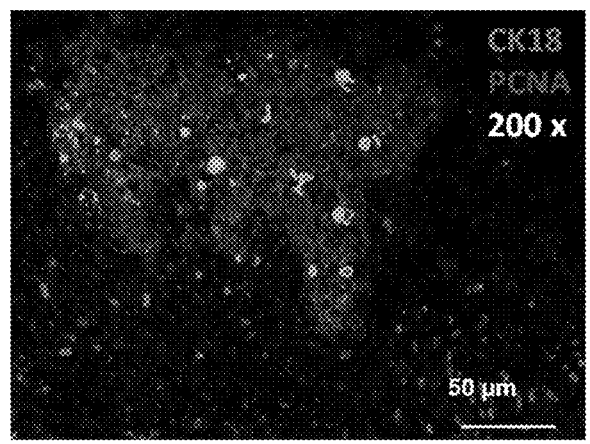
Figure 25:
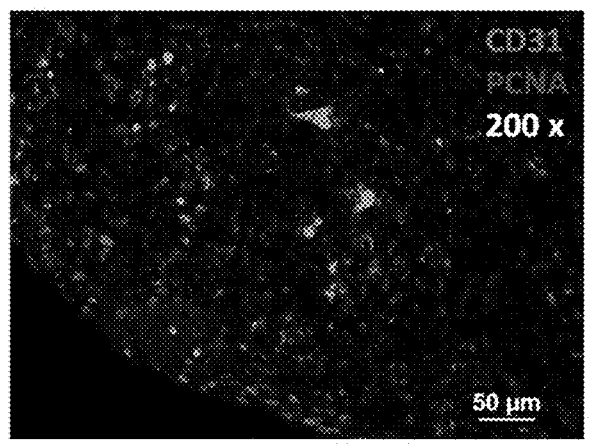

Example 7—Engineered Human Breast Cancer Tumor Model with Stromal Components in the Tumor Tissue Compartment Three-dimensional breast cancer tumor models were constructed with stromal (65% NHMF, 25% HUVEC, 10% SPA in Novogel® 3.0, 150 million cells/ml) and tumor (75% MCF7, 25% HUVEC in Novogel® 3.0, 300 million cells/ml) tissue compartments. See FIG. 25; (A) histological analysis of lipid levels indicates healthy viable adipocytes localized to the stroma (Oil Red O stain); (B) immunohistochemical analysis of the cancer cells in the tumor compartment (green=CK18) together with proliferation marker PCNA (red) shows the majority of proliferation in the tissue within the stromal compartment, with proliferation of the MCF7 cancer cells greatly reduced relative to 2D culture; and (b) immunohistochemical analysis of HUVEC cells (green=CD31) together with proliferation marker PCNA (red) shows localization of HUVEC throughout the tissue (stromal and tumor tissue compartments), with a reduced proliferation rate of the HUVEC as they organize into cellular networks.

Figure 26:
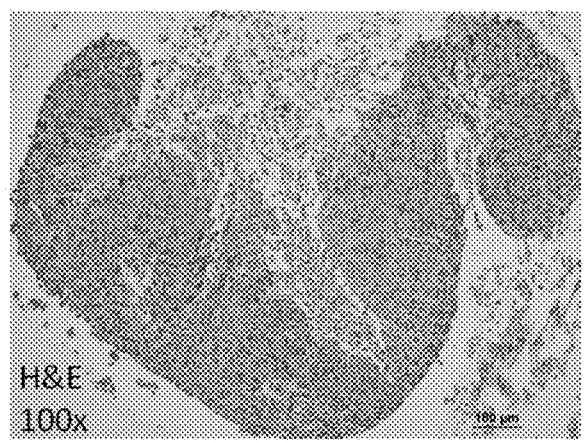
FIG. 26 shows non-limiting exemplary photomicrographs of breast cancer tumor models; in this case, photomicrographs depicting a breast cancer tumor model made with tumor bio-ink with lower firmness at time of bioprinting (H&E (A) and CK18/TE7 staining (B)) and a breast cancer tumor model made with tumor bio-ink with higher firmness at time of bioprinting (H&E (C) and CK18/TE7 staining (D)).
Figure 26:
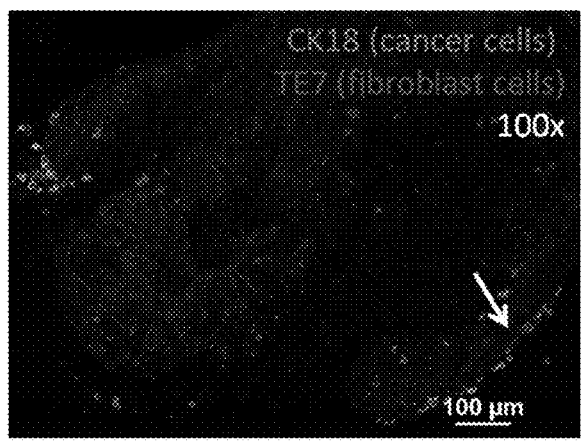
Figure 26:
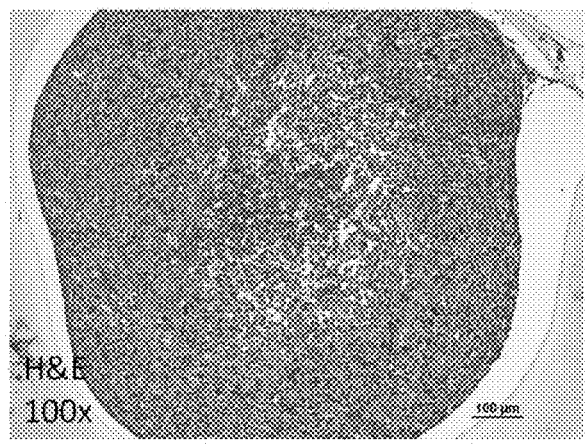
Figure 26:
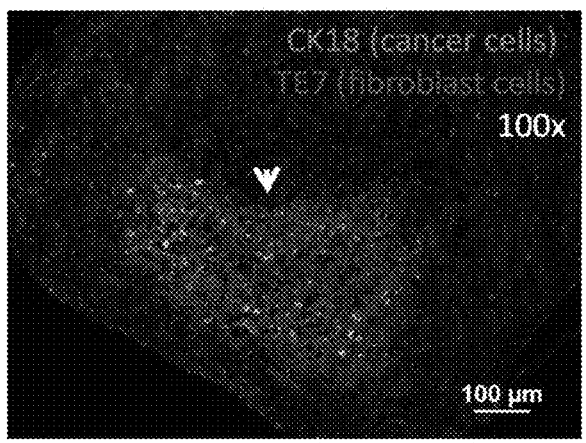

Example 8—Demonstration of Impact of Cellular Density and Resulting Tumor Bio-Ink Firmness at Time of Print Three-dimensional breast cancer tumor models were constructed with stromal (65% NHMF, 25% HUVEC, 10% SPA in Novogel® 3.0, 150 million cells/ml) and tumor (75% MCF7, 25% HUVEC) tissues. To optimize the cellular density of the tumor tissue compartment, tumor bio-ink with lower firmness (150 million cells/mL in liquid 2% alginate; FIGS. 26A and B) was compared to that with higher firmness (300 million cells/mL in Novogel® 3.0; FIGS. 26C and D).

It was hoped that the more liquid fill would allow for denser cellularity in the formed tissue. Unexpectedly, tissues with more liquid bio-ink did not hold together well, showing overall lower tissue cohesion and lack of retention of the cancer cells in the core of the tissue (panel B; green CK18 stain on the outside of the tissue, arrow). Tissues fabricated with the more rigid tumor bio-ink showed improved cellular density, with retention of cancer cells in the core of the tissue (panel D; green CK18 stain in the center of the tissue, arrowhead).

Figure 27:
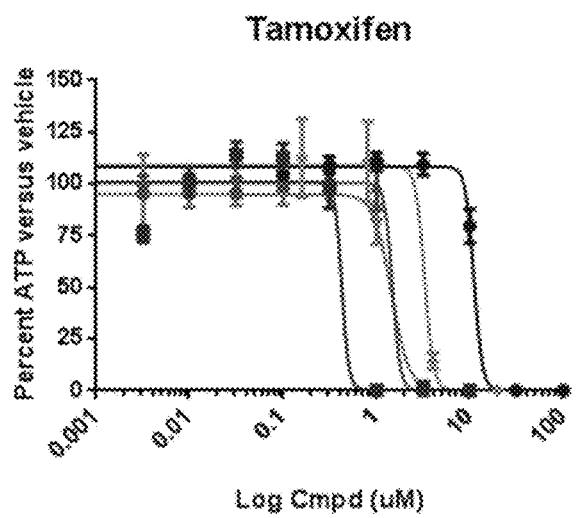
FIG. 27 shows non-limiting exemplary graphs demonstrating viability of component 2D cells versus 3D breast cancer tumor model tissues under exposure to Tamoxifen (A), Paclitaxel (B), and Doxorubicin (C) as well as associated IC50 and percent efficacy data (D).
Figure 27:
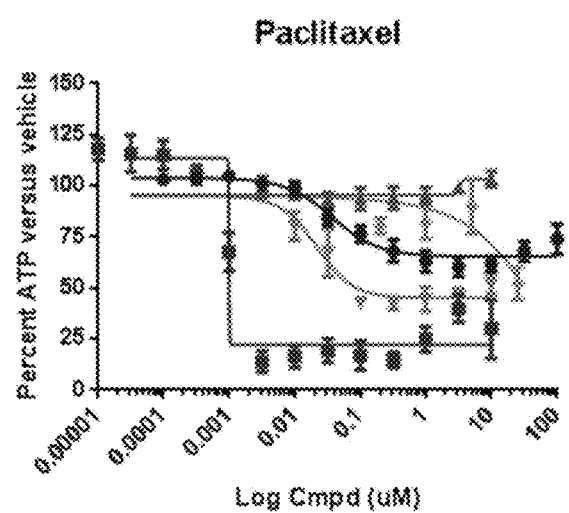
Figure 27:
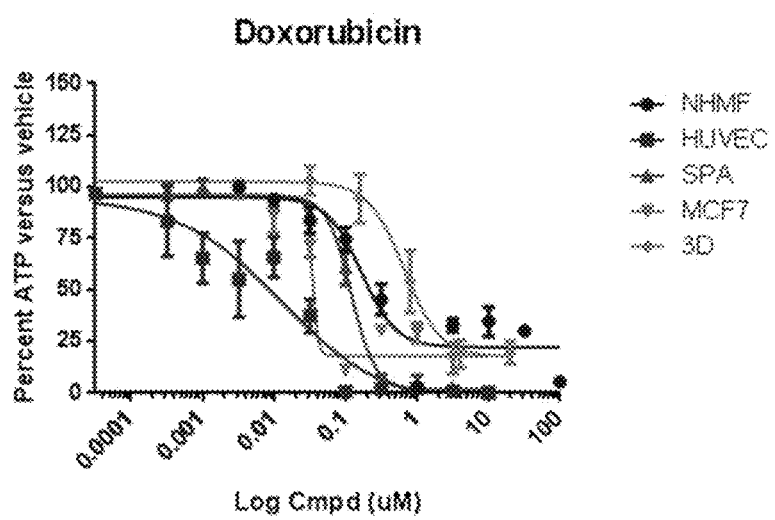

Example 9—Modeling Drug Responses in Human Breast Cancer Tumor Models with Stromal Components in the Tumor Tissue Compartment Component cell lines grown in standard two-dimensional monolayers or three-dimensional bioprinted breast cancer tumor models [constructed with stromal (65% NHMF, 25% HUVEC, 10% SPA in Novogel® 3.0, 150 million cells/ml) and tumor (75% MCF7, 25% HUVEC in Novogel® 3.0, 300 million cells/ml) tissue compartments] were exposed to increasing concentrations of Tamoxifen (see FIG. 27A), Paclitaxel (see FIG. 27B), or Doxorubicin (see FIG. 27C) for 3 days. Viability was measured using Cell Titer Glo. Data shown is the summary of a minimum of three technical replicates in three independent experiments. A table summarizing the IC50 and percent efficacy values (see FIG. 27D) is also shown.

Figure 28:
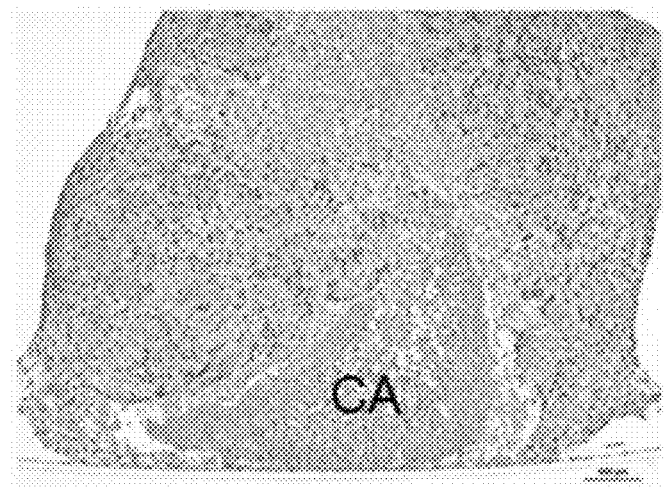
FIG. 28 shows non-limiting exemplary photomicrographs of a breast cancer tumor model; in this case, photomicrographs depicting histological analysis of a 3D breast cancer tumor model featuring inclusion of stromal cells in the tumor portion treated with tamoxifen (B) versus vehicle (A).
Figure 28:
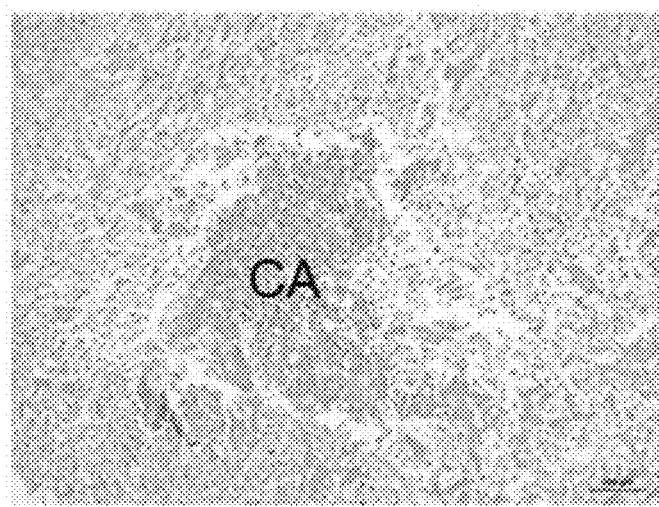

Example 10—Modeling Drug Responses in Human Breast Cancer Tumor Models with Stromal Components in the Tumor Tissue Compartment Three-dimensional bioprinted breast cancer tumor models were constructed with stromal (65% NHMF, 25% HUVEC, 10% SPA in Novogel® 3.0, 150 million cells/nil) and tumor (75% MCF7, 25% HUVEC in Novogel® 3.0, 300 million cells/nil) tissue compartments. Histological analysis of three-dimensional bioprinted breast cancer tumor models treated with tamoxifen was performed. FIG. 28 depicts a cross section of FFPE tissues treated with either vehicle (A) or 100 Tamoxifen (B) for three days and stained by H&E. CA=cancer cell core.

Figure 29:
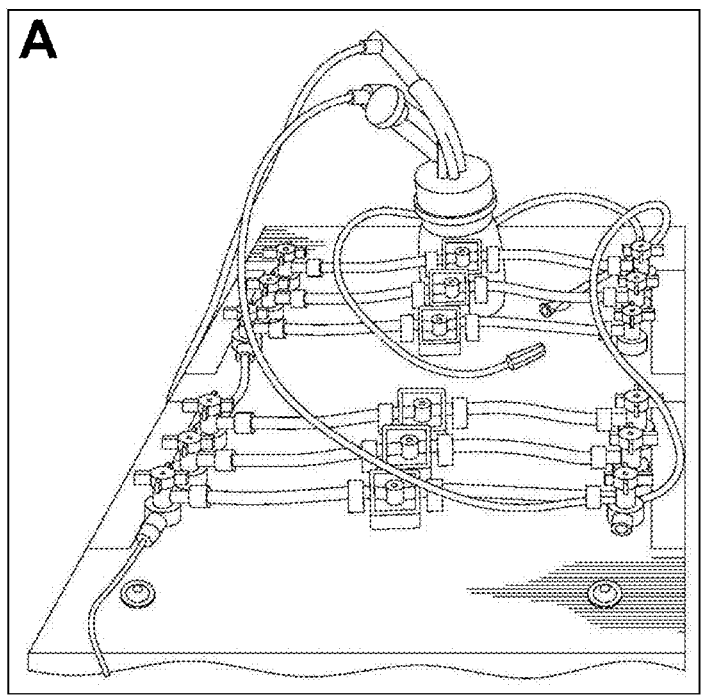
FIG. 29 shows a non-limiting exemplary drawing of a perfusion culture system for the breast cancer tumor models (A) and a photomicrograph of a breast cancer tumor model cultured for 7 days in the system (B).
Figure 29:
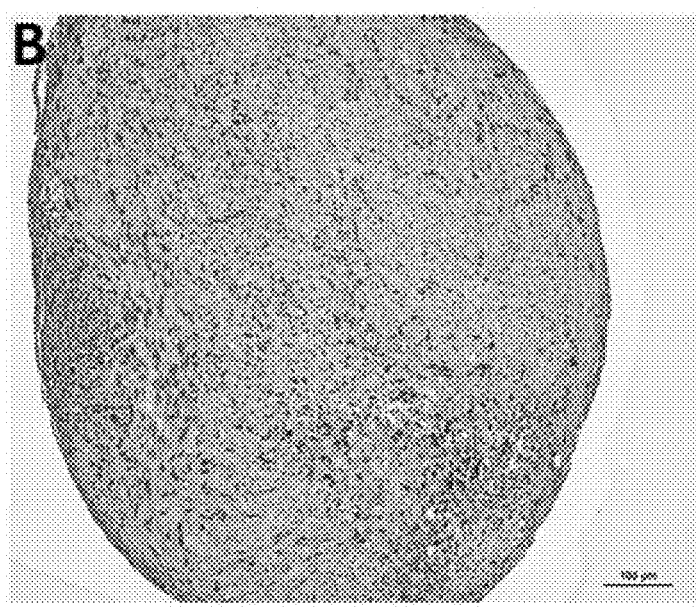

Example 11—Optimization of Perfusion Setup and Fabrication of Tissues Using Primary Patient Tumor Material FIG. 29 depicts (A) optimized perfusion setup utilizing the Kiyatec cube system (Kiyatec, Inc.; Greenville, S.C.) and (B) perfused three-dimensional bioprinted breast cancer tumor models fabricated using primary patient tumor material for the tumor bioink and cultured for 7 days.

What is claimed is:

1. A culture comprising a three-dimensional, engineered, biological breast cancer model and a cell culture media,
    wherein the breast cancer model comprises:
    a. breast stromal tissue comprising human mammary fibroblasts, human endothelial cells, and human mesenchymal stem cells; and
    b. breast cancer tumor tissue comprising breast cancer cells and human endothelial cells, the tumor tissue surrounded on all sides by the stromal tissue to form the three-dimensional, engineered, biological breast cancer model;
    wherein the cell culture media comprises an adipocyte differentiation signal for differentiation of the human mesenchymal stem cells in the breast cancer model into human adipocytes, and
    wherein the human mesenchymal stem cells in the breast cancer model that are exposed to the adipocyte differentiation signal are capable of differentiating into adipocytes in the culture.

2. The culture of claim 1, wherein the breast cancer model is free of pre-formed scaffold.

3. The culture of claim 1, wherein the breast cancer cells are derived from a breast cancer cell line or are primary cancer cells from a patient tumor.

4. The culture of claim 1, wherein the breast cancer model does not comprise a perfusable vascular network, does not comprise red blood cells, and lacks innervation and neural tissue.

5. The culture of claim 1, wherein the mesenchymal stem cells are bone marrow derived mesenchymal stem cells.

6. An array of cultures, wherein each culture in the array comprises a three-dimensional, engineered, biological breast cancer model and a cell culture media,
    wherein the breast cancer model comprises:
    a. breast stromal tissue comprising human mammary fibroblasts, human endothelial cells, and human mesenchymal stem cells; and
    b. breast cancer tumor tissue comprising breast cancer cells and human endothelial cells, the tumor tissue surrounded on all sides by the stromal tissue to form each three-dimensional, engineered, biological breast cancer model;
    wherein the cell culture media comprises an adipocyte differentiation signal for differentiation of the human mesenchymal stem cells in the breast cancer model into human adipocytes,
    wherein the human mesenchymal stem cells in the breast cancer model that are exposed to the adipocyte differentiation signal are capable of differentiating into adipocytes in each culture, and wherein the array is adapted for use in a high throughput assay.

7. The array of claim 6, wherein each breast cancer model is free of pre-formed scaffold.

8. The array of claim 6, wherein each breast cancer model is in a well of a multi-well plate.

9. The array of claim 6, wherein the breast cancer cells are derived from a breast cancer cell line or are primary cancer cells from a patient tumor.

10. The array of claim 6, wherein each breast cancer model does not comprise a perfusable vascular network, does not comprise red blood cells, and lacks innervation and neural tissue.

11. The array of claim 6, wherein the mesenchymal stem cells are bone marrow derived mesenchymal stem cells.

12. A method of producing the culture of claim 1, the method comprising:
    a. preparing a breast stromal bio-ink comprising: an extrusion compound, human mammary fibroblasts, human endothelial cells, and human mesenchymal stem cells;
    b. preparing a breast cancer tumor bio-ink comprising: an extrusion compound, a breast cancer cell type, and a human endothelial cell type;
    c. bioprinting the stromal bio-ink and the tumor bio-ink such that the tumor bio-ink is embedded in the stromal bio-ink and in contact with the stromal bio-ink on all sides; and
    d. maturing the bioprinted bio-inks in a culture comprising cell culture media to remove the extrusion compound and allow the cells to cohere to form a three-dimensional, engineered, biological breast cancer model comprising: breast stromal tissue comprising human mammary fibroblasts, human endothelial cells, and human mesenchymal stem cells, and breast cancer tumor tissue comprising breast cancer cells and human endothelial cells, the tumor tissue surrounded on all sides by the stromal tissue; and
    e. providing an adipocyte differentiation signal in the cell culture media for differentiation of the human mesenchymal stem cells in the breast cancer model into human adipocytes, wherein the human mesenchymal stem cells in the breast cancer model that are exposed to the adipocyte differentiation signal are capable of differentiating into human adipocytes in the culture.

13. The method of claim 12, wherein bioprinting the stromal bio-ink and the tumor bio-ink further comprises:
    a. bioprinting a first sheet of stromal bio-ink on a surface;
    b. bioprinting a continuous border of stromal bio-ink on the first sheet of stromal bio-ink to define a compartment, the compartment open on one side;
    c. bioprinting a node of tumor bio-ink in the compartment; and
    d. bioprinting a second sheet of stromal bio-ink to close the open side of the compartment.

14. The method of claim 12, wherein the model is free of pre-formed scaffold.

15. The method of claim 12, wherein the breast cancer cells are derived from a breast cancer cell line or are primary cancer cells from a patient tumor.

16. The method of claim 12, wherein the breast cancer model does not comprise a perfusable vascular network, does not comprise red blood cells, and lacks innervation and neural tissue.

17. The method of claim 12, wherein the mesenchymal stem cells are bone marrow derived mesenchymal stem cells.

18. The method of claim 12, therein the stromal bio-ink, the tumor bio-ink, or each bio-ink comprises about 50 million cells per milliliter to about 300 million cells per milliliter.

19. The method of claim 12, wherein the extrusion compound in the stromal bio-ink and the tumor bio-ink is a reversibly cross-linkable extrusion compound.

20. The method of claim 19, wherein the method further comprises crosslinking the extrusion compound to physically stabilize the breast cancer model architecture prior to cohesion of the cells.

21. The method of claim 20, wherein the method further comprises removing the crosslinked extrusion compound by enzymatic degradation subsequent to cell cohesion.

22. The method of claim 12, wherein the bioprinting is continuous bioprinting.

23. The method of claim 12, wherein the breast cancer model is 250 µm to 5 mm in its smallest dimension.

\* \* \* \* \*